United States Patent
de Roulet et al.

(10) Patent No.: US 10,851,109 B2
(45) Date of Patent: Dec. 1, 2020

(54) COMPOSITIONS AND METHODS OF USING THE SAME FOR TREATMENT OF NEURODEGENERATIVE AND MITOCHONDRIAL DISEASE

(71) Applicant: Mitokinin, Inc., New York, NY (US)

(72) Inventors: Daniel de Roulet, Old Westbury, NY (US); Robert Devita, Westfield, NJ (US)

(73) Assignee: Mitokinin LLC, New York, NY (US)

( * ) Notice: Subject to any disclaimer, the term of this patent is extended or adjusted under 35 U.S.C. 154(b) by 0 days.

(21) Appl. No.: 16/192,424

(22) Filed: Nov. 15, 2018

(65) Prior Publication Data

US 2019/0194207 A1    Jun. 27, 2019

Related U.S. Application Data

(63) Continuation of application No. 15/118,465, filed as application No. PCT/US2015/015513 on Feb. 11, 2015, now Pat. No. 10,167,286.

(60) Provisional application No. 61/938,691, filed on Feb. 11, 2014.

(51) Int. Cl.
| | |
|---|---|
| A61K 31/519 | (2006.01) |
| C07D 487/04 | (2006.01) |
| C07D 405/12 | (2006.01) |
| C07D 471/04 | (2006.01) |
| C07D 473/34 | (2006.01) |
| C07D 487/16 | (2006.01) |

(52) U.S. Cl.
CPC ......... C07D 487/04 (2013.01); C07D 405/12 (2013.01); C07D 471/04 (2013.01); C07D 473/34 (2013.01); C07D 487/16 (2013.01)

(58) Field of Classification Search
CPC .. A61K 31/497; A61K 31/501; A61K 31/519; C07D 487/04; C07D 473/34
USPC ....... 514/262.1, 263.2, 263.23; 544/262, 277
See application file for complete search history.

(56) References Cited

U.S. PATENT DOCUMENTS

| | | |
|---|---|---|
| 3,037,980 A | 6/1962 | Hitchings et al. |
| 3,863,633 A | 2/1975 | Ryde et al. |
| 3,867,519 A | 2/1975 | Michaels |
| 3,868,445 A | 2/1975 | Ryde et al. |
| 3,960,150 A | 6/1976 | Hussain et al. |
| 3,963,025 A | 6/1976 | Whitaker et al. |
| 4,115,538 A | 9/1978 | Satoh et al. |
| 4,186,184 A | 1/1980 | Zaffaroni |
| 4,303,637 A | 12/1981 | Shell et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,436,128 A | 7/1995 | Harpold et al. |
| 5,443,505 A | 8/1995 | Wong et al. |
| 5,869,079 A | 2/1999 | Wong et al. |
| 10,167,286 B2 | 1/2019 | Roulet et al. |
| 2007/0270362 A1 | 11/2007 | Harlan et al. |
| 2009/0247557 A1 | 10/2009 | Dhalla et al. |
| 2009/0253718 A1 | 10/2009 | Davies et al. |
| 2011/0092583 A1 | 4/2011 | Murty et al. |
| 2013/0045942 A1 | 2/2013 | Shi et al. |
| 2016/0108044 A1 | 4/2016 | Hertz et al. |
| 2017/0190704 A1 | 7/2017 | Roulet et al. |

FOREIGN PATENT DOCUMENTS

| | | |
|---|---|---|
| AU | 201902922 | 2/2015 |
| AU | 2015217152 | 2/2015 |
| AU | 2014214561 | 7/2015 |
| AU | 2018202438 | 4/2018 |
| AU | 2018290225 | 6/2018 |
| CA | 2939219 | 2/2015 |
| CA | 2900779 | 8/2015 |
| CA | 3067695 | 6/2018 |
| CN | 101066268 A | 11/2007 |
| CN | 101066272 A | 11/2007 |
| CN | 102727499 A | 10/2012 |
| EP | 2511283 A1 | 10/2012 |
| EP | 15748579.8 | 2/2015 |
| EP | 14749635.0 | 8/2015 |
| EP | 18821462.1 | 6/2018 |
| KR | 10-2020-7001944 | 6/2018 |
| NZ | 710444 | 7/2015 |
| NZ | 750581 | 2/2019 |
| WO | WO-1994/027583 A2 | 8/1994 |
| WO | WO-1998/004552 A1 | 2/1998 |
| WO | WO-2000/041531 A2 | 7/2000 |
| WO | WO-2001/0044260 A3 | 1/2002 |
| WO | WO-2002/018404 A2 | 3/2002 |

(Continued)

OTHER PUBLICATIONS

Hims, et. al., Journal of Molecular Medicine (Heidelberg, Germany) (2007), 85(2), 149-161.*

Henchcliffe, C. and Beal, M.F., Mitochondrial biology and oxidative stress in Parkinson disease pathogenesis. Nat Clin Pract Neurol. 2008; 4:600-9.

Hertz et al., A Neo-Substrate that Amplifies Catalytic Activity of Parkinson's—Disease Related Kinase PINK 1. Cell. 2013; 154:737-47.

Hertz, N.T. et al., Chemical Genetic Approach for Kinase-Substrate Mapping by Covalent Capture of Thiophosphopeptides and Analysis by Mass Spectrometry. Curr Prot Chem Biol. 2010; 2:15-36.

(Continued)

*Primary Examiner* — Jeffrey H Murray
(74) *Attorney, Agent, or Firm* — Ballard Spahr LLP

(57) ABSTRACT

The disclosure is directed to compounds and pharmaceutically acceptable salts thereof for the treatment and/or prevention of neurodegenerative and/or mitochondrial diseases, such as Parkinson's disease and Leigh's disease. The compounds and pharmaceutically acceptable salts thereof are of the class of nitrogenous bases, for example, pyrimidines, purines, pteridines, and pharmaceutically acceptable salts thereof.

20 Claims, 4 Drawing Sheets

Specification includes a Sequence Listing.

(56) References Cited

FOREIGN PATENT DOCUMENTS

| WO | WO-2005/020892 A2 | 3/2005 |
|---|---|---|
| WO | WO-2006/011130 A1 | 2/2006 |
| WO | WO-2006/084281 A1 | 8/2006 |
| WO | WO-2007/125315 A2 | 11/2007 |
| WO | WO-2009/086457 A2 | 7/2009 |
| WO | WO-2010/046710 A1 | 4/2010 |
| WO | WO-2010/066629 A2 | 6/2010 |
| WO | WO-2010/118367 A2 | 10/2010 |
| WO | WO-2011/006061 A1 | 1/2011 |
| WO | WO-2011/069294 A1 | 6/2011 |
| WO | WO-2011/109469 A1 | 9/2011 |
| WO | WO-2012/080727 A2 | 6/2012 |
| WO | WO-2012/167053 A1 | 12/2012 |
| WO | WO-2013/052699 A2 | 4/2013 |
| WO | PCT/US2014/015863 | 2/2014 |
| WO | WO-2014/124458 A1 | 8/2014 |
| WO | PCT/US2015/015513 | 2/2015 |
| WO | WO-2015/123365 A1 | 8/2015 |
| WO | PCT/US2018/038756 | 6/2018 |

OTHER PUBLICATIONS

Hims, M.M. et al., Therapeutic potential and mechanism of kinetin as a treatment for the human splicing disease familial dysautonomia. J Mol Med (Berl). 2007; 85(2):149-51.
Howard, M.A. 3rd et al., Intracerebral Drug Delivery in Rats with Lesion-Iduced Memory Deficits. J Neurosurg. 1989; 71(1):105-12.
Human PINK 1: Accession No. AY 358957.1; Homo sapiens clone DNA71277 PINK1 (UNQ740) mRNA, complete cds; date downloaded Sep 13, 2017.
Ishii, Y. et al., Cytokinin-Induced Differenetiation of Human Myeloid Leukemia HL-60 Cells is Associated with the Formation of Nucleotides, but Not with Incorporation into DNA or RNA. Biochim Biophys Acta. 2003; 1643(1-3):11-24.
Iwamura, H. et al., Effect of 4-Substituted Pyrrolo[2,3-d]Pyrimidines on the Tobacco Callus Growth. Agric Biol Chem. 1976; 40(9):1885-6.
Kaneti J. et al., Conformational analysis of cytokinins and analogs. Chem Biol Int. 43(1):73-85.
Kim et al., Rescue of PINK 1 Protein Null-specific Mitochondrial Complex IV Deficits by Ginsenoside Re Activation of Nitric Oxide Signaling. J Biol Chem. 2012; 287(53):44109-12.
Al-Muhammed, J., In-Vivo Studies on Dexamethasone Sodium Phosphate Liposomes. J Microencapsul. 1996; 13(3):293-306.
Arena, G. et al., PINK1 protects against cell death induced by mitochondrial depolarization, by phosphorylating Bcl-xL and impairing its proapoptotic cleavage. Cell Death Differ. 2013; 20(7):920-30.
Beilina, A. et al., Mutations in PTEN-induced putative kinase 1 associated with recessive parkinsonism have differential effects on protein stability. Proc Natl Acad Sci USA. 2005; 102:5703-8.
Berge, S.M. et al., Pharmaceutical salts. J Pharm Sci. 1977; 66:1-19.
Billia, F. et al., PTEN-inducible kinase 1 (PINK1)/Park6 is indispensable for normal heart function. Proc Natl Acad Sci USA. 2011; 108(23):9572-7.
Blethrow, J.D. et al., Covalent Capture of Kinase-Specific Phosphopeptides Reveals Cdk1-Cyclin B Substrates. Proc Natl Acad Sci USA. 2008; 105(5):1442-7.
Chang et al., Discovery of PSI-353661, a Novel Purine Nucleotide Prodrug for the Treatment of HCV Infection. ACS Med Chem Lett. 2011; 2:130.
Chen, Y. and Dorn, G., PINK 1-Phosphorylated Mitofusin-2 Is a Parkin Receptor for Culling Damaged Mitochondria. Science. 2013; 340:471-5.
Cheng, C. et al., Potential Purine Antagonists VII. Synthesis of 6-Alkylpyrazolo[3,4-d]Pyrimidines. J Org chem. 1958; 23:191-200.
Chonn, A. and Cullis, P.R., Recent Advances in Liposomal Drug-Delivery Systems. Curr Opin . Biotechnol. 1995; 6(6):698-708.

Clark, I. E. et al., Drosophila pink1 is required for mitochondrial function and interacts genetically with parkin. Nature. 2006; 441(7097):1162-6.
Deng, H. et al., The Parkinson's disease genes pink1 and parkin promote mitochondrial fission and/or inhibit fusion in Drosophila. Proc Natl Acad Sci USA. 2008; 105(38):14503-8.
Devarakonda, M. et al., Synthesis of Novel 2-Alkyl-4-Substituted-Amino-Pyrazolo[3,4-d]pyrimidines as New Leads for Anti-Bacterial and Anti-Cancer Activity. Med Chem Res. 2013; 22:1090-101.
During, M.J. et al., Controlled Release of Dopamine from a Polymeric Brain Implant: in Vivio Characterization. Ann Neurol. 1989; 25(4):351-6.
Edwards, A.M. et al., Too Many Roads Not Taken. Nature. 2011; 470(7333):163-5.
El-Bayouki, K. et al., New Purine Derivatives of Potential Plant-Growth Regulating Properties. Egyp J Chem. 2010; 53(6):803-20.
Eyles, J.E., Oral Delivery and Fate of Poly(Lactic Acid) Microsphere-Encapsulated Interferon in Rats. J Pharm Pharmacol. 1997; 49(7):669-74.
Felley-Bosco et al., Constitutive expression of inducible nitric oxide synthase in human bronchial epithelial cells induces c-fos and stimulates the cGMP pathway. Am J Resp Cell Mol Biol. 1994; 11:159-64.
Furman et al., Activity and the metabolic activation pathway of the potent and selective hepatitis C virus pronucleotide inhibitor PSI-353661. Antiviral Res. 2011: 91:120.
Ganetzky and Wu, Indirect Suppression Involving Behavioral Mutants with Altered Nerve Exciteability in Drosophilia melanogaster. Genetics.1982; 100:4597-614.
Gao, Y. et al., LKB1 in Lung Cancerigenesis: a Serine/Threonine Kinase as Tumor Suppressor. Protein Cell. 2011; 2(2):99-107.
Gao, Z.-H. et al., Controlled Release of Contraceptive Steroids from Biodegradable and Injectable Gel Formulations: in Vivo Evaluation. Pharm Res. 1995; 12(6):864-8.
Gautier, C.A. et al., Loss of PINK 1 causes mitochondrial functional defects and increased sensitivity to oxidative stress. Proc Natl Acad Sci USA. 2008; 105:11364-9.
Geisler, S. et al., The PINK 1/Parkin-mediated mitophagy is compromised by PD-associated mutations. Autophagy. 2010; 6:871-8.
GPRR)9a: Accession No. NP 808219.1; hydroxycarboxylic acid receptor 2 [Homo sapiens]; date downloaded Sep. 13, 2017.
Groarke, D.A. et al., Visualizsation of Agonist-Induced Asociation and Trafficking of Green Fluorescent Protein-Tagged Forms of Both ?-Arrestin-1 and the Thyrotropin-Releasing Horomone Receptor-1. J Biol Chem. 1999; 274(33):23263-9.
Göransson, O. et al., Mechanism of Action of A-769662, a Valuable Tool for Activation of AMP-Activated Protein Kinase. J Biol Chem. 2007; 282(45):32549-60.
Haque, M. E. et al., Cytoplasmic Pink 1 activity protects neurons from dopaminergic neurotoxin MPTP. Proc Natl Acad Sci USA. 2008; 105:1716-21.
Hayashi, E. et al., Purines II. On 6-(Methysulfonyl)-9-Phenyl-9H-Purine. Yakugaku Zasshi. 1979; 99(2):201-4.
Hecker, S.J. et al., Prodrugs of Phosphates and Phosphonates. J Med Chem. 2008; 51(8):2328-45.
Kissil, J.L. et al., DAP-Kinase Loss of Expression in Various Carcinoma and B-Cell Lymphoma cell Lines: Possible Implications for Role as Tumor Suppressor Gene. Oncogene. 1997; 15(4):403-7.
Koh, H. and Chung, J., PINK 1 as a molecular checkpoint in the maintenance of mitochondrial function and integrity. Mol Cell. 2012; 34:7-13.
Kondapalli, C. et al., PINK1 is Activated by Mitochondrial Membrane Potential Depolarization and Stimulates Parkin E3 Ligase Activity by Phosphorylating Serine 65. Open Biol. 2012; 2(5):120080 (17 pages).
Kopencny, D. et al., Mechanism-Based Inhibitors of Cytokinin Oxidase/Dehydrogenase Attack FAD Cofactor. J Mol Biol. 2008; 380(5):886-99.
Kroeger, K.M. et al., Constitutive and Agonist-Dependent homo-Oligomerization of the Thyrotropin-Releasing Hormone Receptor. Detection in Living Cells Using Bioluminescence Resonance Energy Transfer. J Biol Chem. 2001; 276(16):12736-43.

(56) References Cited

OTHER PUBLICATIONS

Kruse, S.E. et al., Mice with mitochondrial complex I deficiency develop a fatal encephalomyopathy. Cell Metab. 2008; 7:312-20.
Kulkarni, R.N. et al., Tissue-Specific Knockout of the Insulin Receptor in Pancreatic Beta Cells Creates an Insulin Secretory Defect Similar to that in Type 2 Diabetes. Cell. 1999; 96(3):329-39.
Lam, A.M. et al., Hepatitis C Virus nucleotide Inhibitors PSI-352938 and PSI-353661 Exhibit a Novel Mechanism of Resistanec Requiring Multiple Mutations with Replicon RNA. J Virol. 2011; 85(23):12334-42.
Lam, A.M. et al., PSI-7851, a Pronucleotide of β-$_D$-2'-Deoxy-2'-Fluoro-2'-C-Methyluridine Monophosphate, is a Potent and Pan-Genotype Inhibitor of Hepatitis C Virus Replication. Antimicrob Agents Chemother. 2010; 54(8):3187-96.
Langer, R., New Methods of Drug Delivery. Science. 1990; 49(4976):1527-33.
Levy, R.J. et al., Inhibition of Calcification of Bioprosthetic Heart Valves by Local Controlled-Release Diphosphonate. Science. 1985; 228(4696):190-2.
Liu, Y. et al., A molecular gate which controls unnatural ATP analogue recognition by the tyrosine kinase v-Src. Bioorg Med Chem. 1998; 6(8):1219-26.
Lourido, S. et al., Calcium-Dependent Protein Kinase 1 is an Essential Regulator of Exocytosis in Toxoplasma. Nature. 2010; 465(7296):359-62.
Marquet, J.-P. et al., Sur une Nouvelle Serie d'Analoges Puriques a Action Antimitotique: Relations Structure-Activite. Chim Ther. 1971; 6(6):427-38 (Original in French—Abstract provided).
Martin, I. et al., Recent Advances in the Genetics of Parkinson's Disease. Annu Rev Genomics Hum Genet. 2011; 12:301-25.
Martins-Branco, D. et al., Ubiquitin Proteasome System in Parkinson's Disease: a Keeper or a Witness? Exp Neurol. 2012; 238(2):89-99.
Meissner, C. et al., The mitochondrial intramembrane protease PARL cleaves human Pink1 to regulate Pink1 trafficking. J Neurochem. 2011; 117(5):856-67.
Merrick, K.A. et al., Switching Cdk2 On or Off with Small Molecules to Reveal Requirements in Human Cell Proliferation. Mol Cell. 2011; 42(5):624-36.
Mills, R.D. et al., Biochemical aspects of the neuroprotective mechanism of PTEN induced kinase-1 (PiNK1). J Neurochem. 2008; 105:18-33.
Mistili, T. and Spector, D.L., Applications of the Green Fluorescent Protein in Cell Biology and Biotechnology. Nat Biotechnol. 1997; 15(10):961-4.
Murakami et al., Adenosine Deaminase-like Protein 1 (ADAL1): Characterization and Substrate Specificity in the Hydrolysis of N6- or 06-Substituted Purine or 2-Aminopurine Nucleoside Monophosphates. J Med Chem. 2011; 54:5902.
Narendra, D. et al., Parkin is recruited selectively to impaired mitochondria and promotes their autophagy. J Cell Biol. 2008; 183(5):795-803.
Narendra, D.P. et al., PINK 1 is selectively stabilized on impaired mitochondria to activate Parkin. PLoS Biol. 2010; 8:e1000298.
Novotna, R. et al., Structurally Varied Cu(II) Complexes Involving Kinetin and Its Derivatives: Synthesis, Characterization and Evaluation of SOD-Mimic Activity. Polyhedron. 2012; 34:56-66.
NP 115785.1; serine/threonine-protein kinase PINK1, mitochondrial precursor [*Homo sapiens*]; date downloaded Sep. 13, 2017.
Offermanns, S. and Simon, M.I., G?15 and G?16 couple a Wide Variety of Receptors to Phospholipase C. J Biol Chem. 1995; 270:15175-80.
Petit, A. et al., Wild-type PINK 1 prevents basal and induced neuronal apoptosis, a protective effect abrogated by Parkinson disease-related mutations. J Biol Chem. 2005; 280:34025-32.
Pridgeon, J.W. et al., PINK 1 Protects against Oxidative Stress by Phosphorylating Mitochondrial Chaperone TRAP 1. PLoS Biol. 2007; 5:e172.

Quintana, A. et al., Complex I Deficiency Due to Loss of Ndufs4 in the Brain Results in Progressive Encephalopathy Resembling Leigh Syndrome. Proc Natl Acad Sci USA. 2010; 107(24):10996-1001.
Rajewski, R.A. et al., Pharmaceutical Applications of Cyclodextrins. 2. in Vivo Drug Delivery. J Pharm Sci. 1996; 85(11):1142-69.
Rao, S. et al., In Vitro Propagation of Withania somnifera and Estimation of Withanolides for Neuological Disorder. 2012; 85-7.
Rautio, J. et al., Prodrugs: Design and Clinical Applications. Nat Rev Drug Discov. 2008; 7(3):255-70.
Reddy, P.G. et al., 2'-Deoxy-2'-?-Fluoro-2'-?-C-Methyl 3',5'-Cyclic Phosphate Nucleotide Prodrug Analogs as Inhibitors of HCV NS5B Polymerase: Discovery of PSI-352938. Bioorg Med Chem Lett. 2010; 20(24):7376-80.
Richardson, P. et al., Report of the 1995 World Health Organization/International Society and Federation of Cardiology Task Force on the Definition and Classification of Cardiomyopathies. Circulation. 1996; 93(5):841-2.
Sadowsky, J.D. et al., Turning a Protein Kinase On or Off from a Single Allosteric Site via Disulfide Trapping. Proc Natl Acad Sci USA. 2011; 108(15):6056-61.
Samaranch, L. et al., PINK 1-linked parkinsonism is associated with Lewy body pathology. Brain. 2010; 133:1128-42.
Shetty, R.S. et al., Specific correction of a splice defect in brain by nutritional supplementation. Hum Mol Genet. 2011; 20(21):4093-101.
Shin, J.H. et al., PARIS (ZNF746) Repression of PGC-1? Contributes to Neurodegeneration in Parkinson's Disease. Cell. 2011; 144(5):689-702.
Siddall, H.K. et al., Loss of PINK1 increases the heart's vulnerability to ischemia-reperfusion injury. PLoS One. 2013; 8(4):e62400.
Sofia et al., Discovery of a [3-d-2'-Deoxy-2'-a-fluoro-2'13-C-methyluridine Nucleotide Prodrug (PS17977) for the Treatment of Hepatitis C Virus. J Med Chem. 2010; 53:7202.
Sofia, M.J. et al., Nucleoside, Nucleotide, and Non-Nucleoside Inhibitors of Hepatitis C Virus NS5B RNA-Dependent RNA-Polymerase. J Med Chem. 2012; 55(6):2481-531.
Sue, M. et al., Specific Interaction of Cytokinins and Their Analogs with Rotenone-Sensitive Internal NADH Dehydrogenase in Potato Tuber Mtichondria. Biosci Biotechnol Agrochem. 1997; 61(11):1806-9.
Vernachio, J.H. et al., INX-08189, a Phosphoramidate Prodrug of 6-O-Methyl-2'-C-Methyl Guanosine, is a Potent Inhibitor of Hepatitis C Virus Replication with Excellent Pharmacokinetic and Pharmacodynamic Properties. Antimicrob Agents Chemother. 2011; 55(5):1843-51.
Wang, J. et al., A Simple and Fast Experimental Model of Myocardial Infarction in the Mouse. Tex Heart Inst J. 2006; 33(3):290-3.
Wang, X. et at., PINK 1 and Parkin target Miro for phosphorylation and degradation to arrest mitochondrial motility. Cell. 2011; 147:893-906.
Zhou et al., Clinical Carbapenem-Resistant Acinetobacter baylyi Strain Coharboring blaSIM-1 and blaOXA-23 from China. AAC. 2011; 44:76.
First Examination Report No. 1 dated Apr. 30, 2018 by the Intellectual Property Office of Autralia for Patent Application No. 2015217152, which was filed on Jul. 25, 2016 (Inventor—de Roulet et al.; Applicant—Mitokinin, LLC) (15 pages).
Choi, Zeatin Prevents Amyloid-Induced Neurotoxicity and Scopolamine-Induced Cognitive Deficits. J Med Food. 2009; 12 (2):271-7.
Okamoto, M. et al., Identification of Novel ASK1 Inhibitors Using Virtual Screening. Bioorg Md Chem. 2011; 19:486-9.
International Search Report and Written Opinion dated Apr. 29, 2015 by the International Searching Authority for Patent Application No. PCT/US2015/015513, which was filed on Feb. 11, 2015 and published as WO 2015/123365 on Aug. 20, 2015 (Inventor—de Roulet et al.; Applicant—Mitokinin, LLC) (10 pages).
International Preliminary Report on Patentability dated Aug. 16, 2016 by the International Searching Authority for Patent Application No. PCT/US2015/015513, which was filed on Feb. 11, 2015 and published as WO 2015/123365 on Aug. 20, 2015 (Inventor—de Roulet et al.; Applicant—Mitokinin, LLC) (7 pages).
Supplementary Search Report dated Jul. 5, 2017 by the European Patent Office for Patent Application No. 15748579.8, which was

(56) References Cited

OTHER PUBLICATIONS filed on Sep. 8, 2016 and published as EP 3104706 on Dec. 21, 2016 (Inventor—de Roulet et al.; Applicant—Mitokinin, LLC) (10 pages).
International Search Report and Written Opinion dated May 30, 2014 by the International Searching Authority for Patent Application No. PCT/US2014/015863, which was filed on Feb. 11, 2014 and published as WO 2014/124458 on Aug. 14, 2014 (Inventor—Hertz et al.; Applicant—Mitokinin, LLC et al.) (9 pages).
International Preliminary Report on Patentability dated Aug. 11, 2015 2014 by the International Searching Authority for Patent Application No. PCT/US2014/015863, which was filed on Feb. 11, 2014 and published as WO 2014/124458 on Aug. 14, 2014 (Inventor—Hertz et al.; Applicant—Mitokinin, LLC et al.) (6 pages).
Supplementary European Search Report dated Sep. 13, 2016 by the European Patent Office for Patent Application No. 14749635.0, which was filed on Feb. 11, 2014 and published as EP 2953950 on Dec. 16, 2015 (Inventor—Hertz et al.; Applicant—Mitokinin, LLC et al.) (7 pages).
International Search report and Written Opinion dated Oct. 30, 2018 by the International Searching Authority for Patent Application No. PCT/US2018/038756, which was filed on Jun. 21, 2018 and published as WO 2018/237145 on Dec. 27, 2018 (Inventor—de Roulet et al.; Applicant—Mitokinin, Inc.) (11 pages).
Examination Report was dated Nov. 29, 2019 by the Australian Patent Office for AU Application No. 2019202922, filed on Feb. 11, 2015 (Applicant—Mitokinin, Inc.) (9 pages).
Restriction Requirement was dated Apr. 18, 2017 by the USPTO for U.S. Appl. No. 15/118,465, filed Aug. 11, 2016 and now U.S. Pat. No. 10,167,286 on Jan. 1, 2019 (Inventor—Daniel de Roulet) (8 pages).
Response to Restriction Requirement was dated Jun. 19, 2017 to the USPTO for U.S. Appl. No. 15/118,465, filed Aug. 11, 2016 and now U.S. Pat. No. 10,167,286 on Jan. 1, 2019 (Inventor—Daniel de Roulet) (10 pages).
Non Final Rejection was dated Jul. 25, 2017 by the USPTO for U.S. Appl. No. 15/118,465, filed Aug. 11, 2016 and now U.S. Pat. No. 10,167,286 on Jan. 1, 2019 (Inventor—Daniel de Roulet) (13 pages).
Response to Non Final Rejection was dated Oct. 25, 2017 to the USPTO for U.S. Appl. No. 15/118,465, filed Aug. 11, 2016 and now U.S. Pat. No. 10,167,286 on Jan. 1, 2019 (Inventor—Daniel de Roulet) (13 pages).
Final Rejection was dated Dec. 7, 2017 by the USPTO for U.S. Appl. No. 15/118,465, filed Aug. 11, 2016 and now U.S. Pat. No. 10,167,286 on Jan. 1, 2019 (Inventor—Daniel de Roulet) (10 pages).
Response to Final Rejection was dated Mar. 7, 2018 tp the USPTO for U.S. Appl. No. 15/118,465, filed Aug. 11, 2016 and now U.S. Pat. No. 10,167,286 on Jan. 1, 2019 (Inventor—Daniel de Roulet) (11 pages).
Ex Parte Quayle Action was issued on Mar. 22, 2018 by the USPTO for U.S. Appl. No. 15/118,465, filed Aug. 11, 2016 and granted as U.S. Pat. No. 10,167,286 on Jan. 1, 2019 (Inventor—Daniel de Roulet) (5 pages).
Response to Ex Parte Quayle Action was mailed on Jun. 22, 2018 to the USPTO for U.S. Appl. No. 15/118,465, filed Aug. 11, 2016 and granted as U.S. Pat. No. 10,167,286 on Jan. 1, 2019 (Inventor—Daniel de Roulet) (336 pages).
Notice of Allowance was dated Aug. 10, 2018 by the USPTO for U.S. Appl. No. 15/118,465, filed Aug. 11, 2016 and now U.S. Pat. No. 10,167,286 on Jan. 1, 2019 (Inventor—Daniel de Roulet) (8 pages).
Issue Notification was dated Dec. 12, 2018 by the USPTO for U.S. Appl. No. 15/118,465, filed Aug. 11, 2016 and now U.S. Pat. No. 10,167,286 on Jan. 1, 2019 (Inventor—Daniel de Roulet) (1 page).
U.S. Appl. No. 61/938,691, filed Feb. 11, 2014, Daniel de Roulet (Mitokinin, LLC).
U.S. Appl. No. 15/118,465 (U.S. Pat. No. 10,167,286), filed Aug. 11, 2016 (Jan. 1, 2019), Daniel de Roulet (Mitokinin, LLC).
U.S. Appl. No. 61/763,444, filed Feb. 11, 2013, Nicholas T. Hertz (Mitokinin, LLC).
U.S. Appl. No. 14/823,934 (2016/0108044), filed Aug. 11, 2015 (Apr. 21, 2016), Nicholas T. Hertz (Mitokinin, LLC).
U.S. Appl. No. 15/438,496 (2018/0072731), filed Feb. 21, 2017 (Mar. 15, 2018), Nicholas T. Hertz (Mitokinin, LLC).
U.S. Appl. No. 62/522,840, filed Jun. 21, 2017, Daniel de Roulet (Mitokinin, LLC).
U.S. Appl. No. 16/624,980, filed Jun. 21, 2018, Daniel de Roulet (Mitokinin, LLC).
U.S. Appl. No. 62/828,995, filed Apr. 3, 2019, Daniel de Roulet (Mitokinin, LLC).
U.S. Appl. No. 62/879,794, filed Apr. 3, 2019, Daniel de Roulet (Mitokinin, LLC).
U.S. Appl. No. 62/933,632, filed Apr. 3, 2019, Daniel de Roulet (Mitokinin, LLC).

* cited by examiner

SEQUENCE LISTING

<160> NUMBER OF SEQ ID NOS: 3

<210> SEQ ID NO 1
<211> LENGTH: 109
<212> TYPE: PRT
<213> ORGANISM: Artificial Sequence
<220> FEATURE:
<223> OTHER INFORMATION: Synthetic Construct

<400> SEQUENCE: 1

```
Met Leu Trp Trp Leu Val Leu Leu Leu Pro Thr Leu Lys Ser Val
1               5                   10                  15

Phe Cys Ser Leu Val Thr Ser Leu Tyr Leu Pro Asn Thr Glu Asp Leu
            20                  25                  30

Ser Leu Trp Leu Trp Pro Lys Pro Asp Leu His Ser Gly Thr Arg Thr
        35                  40                  45

Glu Val Ser Thr His Thr Val Pro Ser Lys Pro Gly Thr Ala Ser Pro
    50                  55                  60

Cys Trp Pro Leu Ala Gly Ala Val Pro Ser Pro Thr Val Ser Arg Leu
65                  70                  75                  80

Glu Ala Leu Thr Arg Ala Val Gln Val Ala Glu Pro Leu Gly Ser Cys
```

-continued

```
                85                  90                  95
Gly Phe Gln Gly Gly Pro Cys Pro Gly Arg Arg Arg Asp
            100                 105

<210> SEQ ID NO 2
<211> LENGTH: 580
<212> TYPE: PRT
<213> ORGANISM: Artificial Sequence
<220> FEATURE:
<223> OTHER INFORMATION: Synthetic Construct

<400> SEQUENCE: 2

Met Ala Val Arg Gln Ala Leu Gly Arg Gly Leu Gln Leu Gly Arg Ala
1               5                   10                  15

Leu Leu Leu Arg Phe Ala Pro Lys Pro Gly Pro Leu Phe Gly Trp Gly
                20                  25                  30

Lys Pro Gly Pro Ala Ala Ala Trp Gly Arg Gly Glu Arg Pro Gly Gln
            35                  40                  45

Val Val Ser Pro Gly Ala Gln Pro Arg Pro Val Gly Leu Pro Leu Pro
        50                  55                  60

Asp Arg Tyr Arg Phe Phe Arg Gln Ser Val Ala Gly Leu Ala Ala Arg
65                  70                  75                  80

Ile Gln Arg Gln Phe Met Val Arg Ala Arg Gly Gly Ala Gly Pro Cys
                85                  90                  95

Gly Arg Ala Val Phe Leu Ala Phe Gly Leu Gly Leu Gly Leu Ile Glu
            100                 105                 110

Glu Lys Gln Ala Glu Gly Arg Arg Ala Ala Ser Ala Cys Gln Glu Ile
        115                 120                 125

Gln Ala Ile Phe Thr Gln Lys Thr Lys Arg Val Ser Asp Pro Leu Asp
    130                 135                 140

Thr Arg Cys Trp Gln Gly Phe Arg Leu Glu Asp Tyr Leu Ile Gly Gln
145                 150                 155                 160

Ala Ile Gly Lys Gly Cys Asn Ala Ala Val Tyr Glu Ala Thr Met Pro
                165                 170                 175

Thr Leu Pro Gln His Leu Glu Lys Ala Lys His Leu Gly Leu Ile Gly
            180                 185                 190

Lys Gly Pro Asp Val Val Leu Lys Gly Ala Asp Gly Glu Gln Ala Pro
        195                 200                 205

Gly Thr Pro Thr Phe Pro Phe Ala Ile Lys Met Met Trp Asn Ile Ser
    210                 215                 220

Ala Gly Ser Ser Glu Ala Ile Leu Ser Lys Met Ser Gln Glu Leu
225                 230                 235                 240

Val Pro Ala Ser Arg Val Ala Leu Ala Gly Glu Tyr Gly Ala Val Thr
                245                 250                 255

Tyr Arg Arg Ser Arg Asp Gly Pro Lys Gln Leu Ala Pro His Pro Asn
            260                 265                 270

Ile Ile Arg Val Phe Arg Ala Phe Thr Ser Ser Val Pro Leu Leu Pro
        275                 280                 285

Gly Ala Leu Ala Asp Tyr Pro Asp Met Leu Pro Pro His Tyr Tyr Pro
    290                 295                 300

Glu Gly Leu Gly His Gly Arg Thr Leu Phe Leu Val Met Lys Asn Tyr
305                 310                 315                 320

Pro Cys Thr Leu Arg Gln Tyr Leu Glu Glu Gln Thr Pro Ser Ser Arg
                325                 330                 335

Leu Ala Thr Met Met Thr Leu Gln Leu Leu Glu Gly Val Asp His Leu
```

```
                    340                 345                 350
Val Gln Gln Gly Ile Ala His Arg Asp Leu Lys Ser Asp Asn Ile Leu
            355                 360                 365
Val Glu Trp Asp Ser Asp Gly Cys Pro Trp Leu Val Ile Ser Asp Phe
        370                 375                 380
Gly Cys Cys Leu Ala Asp Gln His Val Gly Leu Arg Leu Pro Phe Asn
385                 390                 395                 400
Ser Ser Ser Val Glu Arg Gly Gly Asn Gly Ser Leu Met Ala Pro Glu
                405                 410                 415
Val Ser Thr Ala His Ser Gly Pro Ser Ala Val Ile Asp Tyr Ser Lys
            420                 425                 430
Ala Asp Thr Trp Ala Val Gly Ala Ile Ala Tyr Glu Ile Phe Gly Leu
        435                 440                 445
Ala Asn Pro Phe Tyr Gly Gln Gly Ser Ala His Leu Glu Ser Arg Ser
    450                 455                 460
Tyr Gln Glu Ala Gln Leu Pro Glu Met Pro Glu Ser Val Pro Pro Glu
465                 470                 475                 480
Ala Arg Arg Leu Val Arg Ser Leu Leu Gln Arg Glu Ala Ser Lys Arg
                485                 490                 495
Pro Ser Ala Arg Leu Ala Ala Asn Val Leu His Leu Ser Leu Trp Gly
            500                 505                 510
Glu His Leu Leu Ala Leu Lys Asn Leu Lys Leu Asp Lys Met Ile Ala
        515                 520                 525
Trp Leu Leu Gln Gln Ser Ala Ala Thr Leu Leu Ala Asp Arg Leu Arg
    530                 535                 540
Glu Lys Ser Cys Val Glu Thr Lys Leu Gln Met Leu Phe Leu Ala Asn
545                 550                 555                 560
Leu Glu Cys Glu Ala Leu Cys Gln Ala Ala Leu Leu Ser Ser Trp
                565                 570                 575
Arg Ala Ala Pro
            580

<210> SEQ ID NO 3
<211> LENGTH: 257
<212> TYPE: PRT
<213> ORGANISM: Artificial Sequence
<220> FEATURE:
<223> OTHER INFORMATION: Synthetic Construct

<400> SEQUENCE: 3

Met Ala Val Arg Gln Ala Leu Gly Arg Gly Leu Gln Leu Gly Arg Ala
1               5                   10                  15
Leu Leu Leu Arg Phe Ala Pro Lys Pro Gly Pro Val Ser Gly Trp Gly
            20                  25                  30
Lys Pro Gly Pro Gly Ala Ala Trp Gly Arg Gly Glu Arg Pro Gly Arg
        35                  40                  45
Val Ser Ser Pro Gly Ala Gln Pro Arg Pro Leu Gly Leu Pro Leu Pro
    50                  55                  60
Asp Arg Tyr Arg Phe Phe Arg Gln Ser Val Ala Gly Leu Ala Ala Arg
65                  70                  75                  80
Ile Gln Arg Gln Phe Val Val Arg Ala Arg Gly Ala Gly Ala Pro Cys
                85                  90                  95
Gly Arg Ala Val Phe Leu Ala Phe Gly Leu Gly Leu Gly Leu Ile Glu
            100                 105                 110
Glu Lys Gln Ala Glu Ser Arg Arg Ala Ala Ser Ala Cys Gln Glu Ile
```

```
            115                 120                 125
Gln Ala Ile Phe Thr Gln Lys Asn Lys Gln Val Ser Asp Pro Leu Asp
        130                 135                 140

Thr Arg Arg Trp Gln Gly Phe Arg Leu Glu Asp Tyr Leu Ile Gly Gln
145                 150                 155                 160

Ala Ile Gly Lys Gly Cys Asn Ala Ala Val Tyr Glu Ala Thr Met Pro
                165                 170                 175

Thr Leu Pro Gln His Leu Glu Lys Ala Lys His Leu Gly Leu Leu Gly
            180                 185                 190

Lys Gly Pro Asp Val Val Ser Lys Gly Ala Asp Gly Glu Gln Ala Pro
        195                 200                 205

Gly Ala Pro Ala Phe Pro Phe Ala Ile Lys Met Met Trp Asn Ile Ser
    210                 215                 220

Ala Gly Ser Ser Ser Glu Ala Ile Leu Ser Lys Met Ser Gln Glu Leu
225                 230                 235                 240

Glu Ala Leu Gly Ser Ala Asn Arg Lys Gly Thr Leu Gln Gln Phe Arg
                245                 250                 255

Arg
```

COMPOSITIONS AND METHODS OF USING THE SAME FOR TREATMENT OF NEURODEGENERATIVE AND MITOCHONDRIAL DISEASE

CROSS-REFERENCE TO RELATED APPLICATIONS

This Application is a continuation of U.S. application Ser. No. 15/118,465, filed on Aug. 11, 2016, which granted on Jan. 1, 2019 as U.S. Pat. No. 10,167,286, which is a U.S. National Stage filing under 35 U.S.C. § 371 of International Application No. PCT/US2015/015513, filed on Feb. 11, 2015, which claims priority to U.S. Provisional Application No. 61/938,691, filed on Feb. 11, 2014, the contents of which are incorporated herein by reference in their entireties.

REFERENCE TO SEQUENCE LISTING

The Sequence Listing submitted Mar. 11, 2019 as a text file named "37930_0001U3_ST25.txt," created on Mar. 1, 2019, and having a size of 12,288 bytes is hereby incorporated by reference pursuant to 37 C.F.R. § 1.52(e)(5).

FIELD OF THE DISCLOSURE

The present disclosure is directed, in part, to compounds, or pharmaceutically acceptable salts thereof, for modulating the activity of PINK 1 and/or methods for treating and or preventing Parkinson's disease and/or mitochondrial diseases.

BACKGROUND OF THE DISCLOSURE

Studies have correlated mitochondrial function with the disease of cardiomyopathy and for neuron health and survival. Specifically, aberrant mitochondrial quality control has been demonstrated to be an important factor in the development of neurodegenerative diseases and cardiomyopathy.[1,2] The mitochondrial kinase PTEN Induced Kinase 1 (PINK1) plays an important role in the mitochondrial quality control processes by responding to damage at the level of individual mitochondria. The PINK1 pathway has also been linked to the induction of mitochondrial biogenesis, and, critically, the reduction of mitochondrially induced apoptosis.[3,4,11]

Parkinson's Disease (PD) is one of the most common neurodegenerative disorders, however no disease modifying therapies are currently approved to treat PD. Both environmental and genetic factors lead to progressive apoptosis of dopaminergic neurons, lowered dopamine levels and ultimately PD. PINK1 kinase activity appears to mediate its neuroprotective activity. The regulation of mitochondrial movement, distribution and clearance is a key part of neuronal oxidative stress response. Disruptions to these regulatory pathways have been shown to contribute to chronic neurodegenerative disease.[1,2]

Cardiomyopathy refers to a disease of cardiac muscle tissue, and it is estimated that cardiomyopathy accounts for 5-10% of the 5-6 million patients already diagnosed with heart failure in the United States. Based on etiology and pathophysiology, the World Health Organization created a classification of cardiomyopathy types which includes dilated cardiomyopathy, hypertrophic cardiomyopathy, restrictive cardiomyopathy, arrhythmogenic right ventricular cardiomyopathy, and unclassified cardiomyopathy.[5] PINK1 kinase activity appears to mediate its cardioprotective activity. The regulation of mitochondrial movement, distribution and clearance is a part of cardiac cell oxidative stress response. Disruptions to these regulatory pathways have been shown to contribute to cardiomyopathy.[1,2]

Neural pathologies frequently result from dysfunctional mitochondria, and Leigh syndrome (LS, also known as Leigh's disease or Leigh disease) is a common clinical phenotype.[1] LS, or subacute necrotizing encephalopathy, is a progressive neurodegenerative disorder affecting 1 in 40,000 live births.[2,3] LS is regarded as the most common infantile mitochondrial disorder, and most patients exhibit symptoms before 1 mo of age.[4,5] Several cases of adult-onset LS have also been reported recently.[6-10] In vivo imaging techniques such as MRI reveal bilateral hyperintense lesions in the basal ganglia, thalamus, substantia nigra, brainstem, cerebellar white matter and cortex, cerebral white matter, or spinal cord of LS patients.[6,11-14] The lesions usually correlate with gliosis, demyelination, capillary proliferation, and/or necrosis.[10,15] Behavioral symptoms of LS patients can include (with a wide variety of clinical presentation) developmental retardation, hypotonia, ataxia, spasticity, dystonia, weakness, optic atrophy, defects in eye or eyelid movement, hearing impairment, breathing abnormalities, dysarthria, swallowing difficulties, failure to thrive, and gastrointestinal problems.[4-6,16,17] The cause of death in most LS cases is unclear, and the lack of a genetic model to study the disease progression and cause of death has impeded the development of adequate treatment. Prognosis for LS (and most diseases resulting from mitochondrial dysfunction) is very poor; there is no cure and treatment is often ineffective.

Thus, there is a need in the art for effective PTNK1 agonists and compounds for treating neurodegenerative diseases such as Parkinson's disease and cardiomyopathy and Leigh syndrome. Disclosed herein are solutions to these and other problems in the art.

SUMMARY OF THE DISCLOSURE

In some embodiments, the present disclosure provides a compound having Formula I or pharmaceutically acceptable salt thereof:

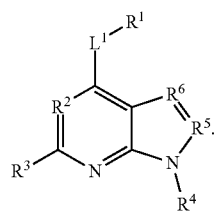

In some embodiments, the composition comprises at least one or a combination of the compounds, or their respective pharmaceutically acceptable salts thereof, chosen from:

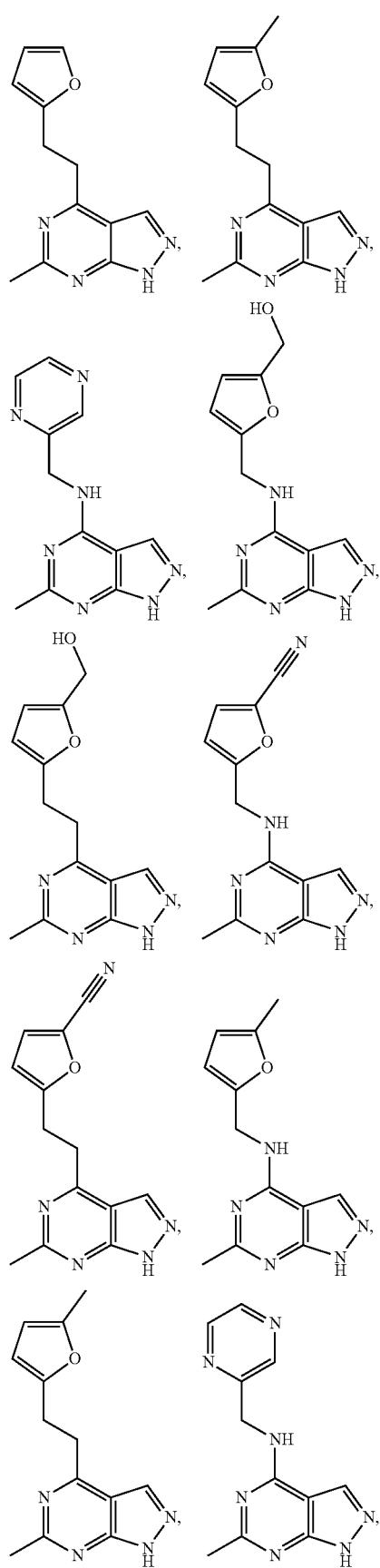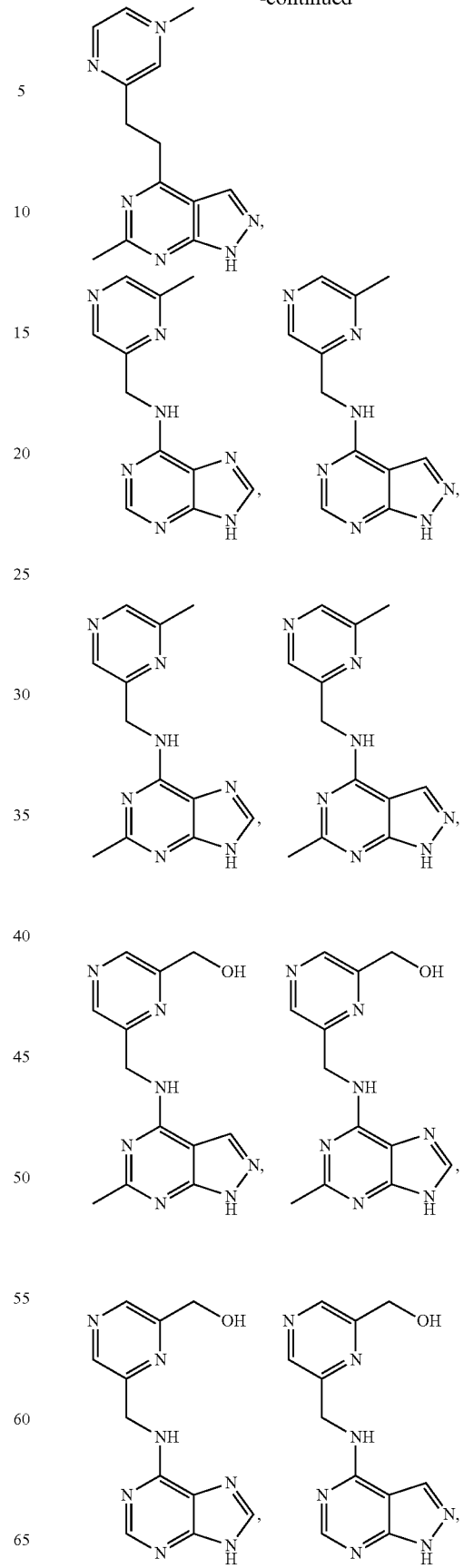

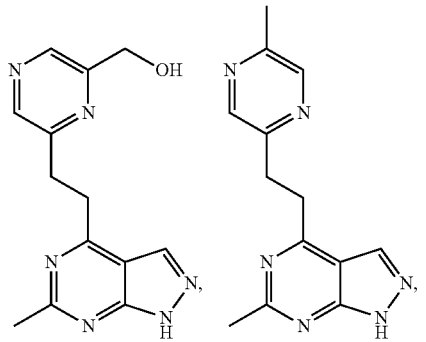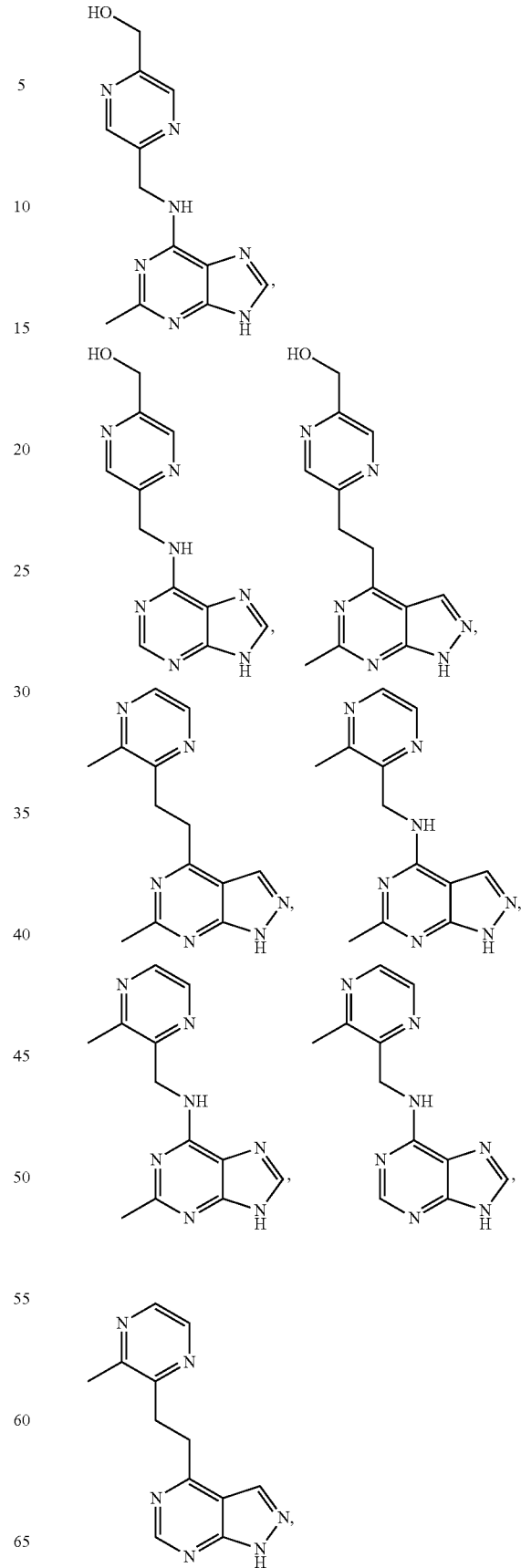

-continued

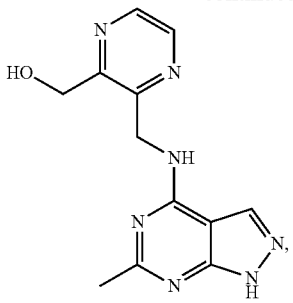

-continued

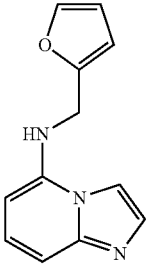

In some embodiments, a pharmaceutical composition comprising a compound or pharmaceutically acceptable salt thereof that is described herein is provided. In some embodiments, the pharmaceutical compositions disclosed herein comprises one or more active agents other than the compound having Formula I.

In some embodiments, a pharmaceutical composition comprising a compound or pharmaceutically acceptable salt thereof that is described herein is provided wherein one or more of the compounds disclosed herein is excluded. In some embodiments, a pharmaceutical composition comprising a compound or pharmaceutically acceptable salt thereof that is described herein is provided wherein compounds of Formula Ia as disclosed herein are excluded.

In some embodiments, the disclosure related to methods of treating or preventing neurodegenerative disease or mitochondrial disease in a subject in need thereof comprising administering to the subject one or more compounds, or a pharmaceutically acceptable salt thereof described herein or a pharmaceutical composition comprising one or more compounds described herein, or pharmaceutically acceptable salt thereof.

In some embodiments, a method of treating Parkinson's disease with a compound described herein or salt thereof is provided. In some embodiments, a method of preventing early onset of Parkinson's disease with a compound described herein or salt thereof is provided. In some embodiments, a method of reducing the number or severity of symptoms of Parkinson's disease with a compound described herein or salt thereof is provided.

In some embodiments, a method of treating mitochondrial disease with a compound described herein or salt thereof is provided. In some embodiments, a method of preventing early onset of mitochondrial disease with a compound described herein or salt thereof is provided. In some embodiments, a method of reducing the number or severity of symptoms of mitochondrial disease with a compound described herein or salt thereof is provided.

In some embodiments, a method of treating Leigh's Disease with a compound described herein or salt thereof is provided. In some embodiments, a method of preventing early onset of Leigh's Disease with a compound described herein or salt thereof is provided. In some embodiments, a method of reducing the number or severity of symptoms of Leigh's Disease with a compound described herein or salt thereof is provided.

In some aspects, the disclosure relates to a method of treating and/or preventing a neurodegenerative disease in a subject comprising administering to the subject a therapeutically effective amount of one or more compounds disclosed herein, or a pharmaceutically acceptable salt thereof, or any pharmaceutical compositions comprising any one or more compounds or pharmaceutically acceptable salts thereof disclosed herein. In some embodiments, the neurodegenerative disease is Parkinson's disease.

In some aspects, the disclosure relates to a method of treating and/or preventing a mitochondrial disease in a subject comprising administering to the subject a therapeutically effective amount of one or more compounds disclosed herein, or a pharmaceutically acceptable salt thereof, or any pharmaceutical compositions comprising any one or more compounds or pharmaceutically acceptable salts thereof disclosed herein. In some embodiments, the mitochondrial disease is Leigh disease or a complex I deficiency. In some embodiments, the compound is kinetin or a pharmaceutically acceptable salt thereof.

DESCRIPTION OF EMBODIMENTS

Figure 1:
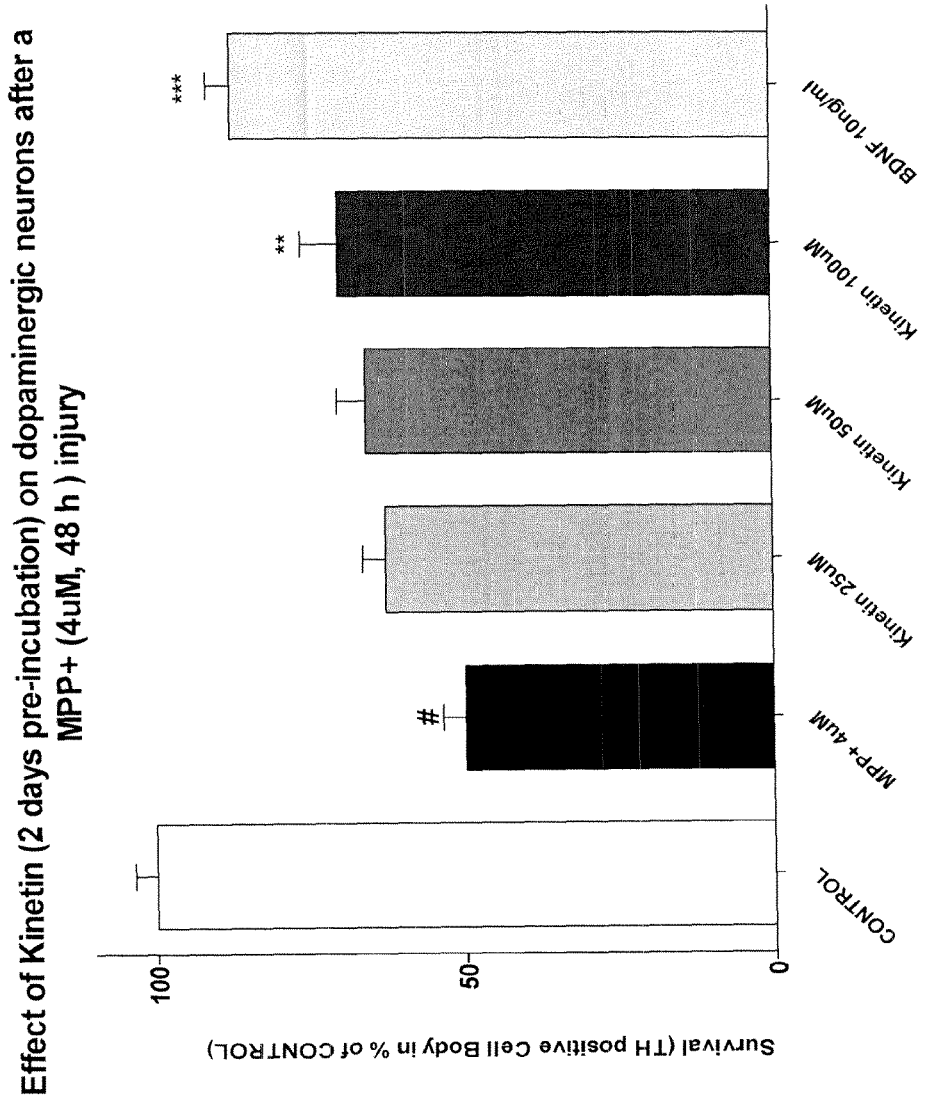
FIG. 1 depicts the effect of Kinetin pre-incubated during 2 days on survival of mouse primary dopaminergic neuron culture injured by MPP+ (4 µM) expressed in percentage of control. (mean+/−s.e.m; * p<0.05;  P<0.01; * P<0.005; MPP+vs control; one way Anova followed by Dunnett's test).

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2, 4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'-represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heterocycloalkyl are non-aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1, 2, 5, 6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2, 2, 2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5, 6-fused ring heteroarylene refers to two rings fused together, wherein one ring has 5 members and the other ring has 6 members, and wherein at least one ring is a heteroaryl ring. Likewise, a 6, 6-fused ring heteroarylene refers to two rings fused together, wherein one ring has 6 members and the other ring has 6 members, and wherein at least one ring is a heteroaryl ring. And a 6, 5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5 thiazolyl 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═, ═NR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R", —NR—C(NR'R"R'")═NR"", —NR—C(NR'R")═NR'", —S(O)R", —S($O)_2$R', —S($O)_2$NR'R", —NRS$O_2$R', —NR'NR"R'", —ONR'R", —NR'C═(O)NR"NR'"R"", —CN, —$NO_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the disclosure includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)K—C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR'", —S(O)R', —S(O)$_2$R', —S(O)$_2$NR'R", —NRSO$_2$R', —NR'NR"R'", —ONR'R'", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, monophosphate (or derivatives thereof), diphosphate (or derivatives thereof), triphosphate (or derivatives thereof), in a number ranging from zero to the total number of open valences on the aromatic ring system; and where R', R", R'", and R" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the disclosure includes more than one R group, for example, each of the R groups is independently selected as are each R', R", R'", and R" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH$_2$)r-B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties: (A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (B) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (ii) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(a) oxo, halogen, —CF$_3$, —CN, —OH, —NH$_2$, —COON, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (b) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from: oxo, halogen, —CF$_3$, —CN, OH, —NH$_2$, —COON, —CONH$_2$, —NO$_2$, —SH, —SO$_2$Cl, —SO$_3$H, —SO$_4$H— SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), and triphosphate (or derivatives thereof).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{100}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent. In embodiments, the prodrug form may include a phosphate derivative or a sugar (e.g. ribose) derivative. For example prodrugs moieties used in HCV nucleoside and nucleotide prodrugs may be added to the compounds described herein or the compounds used in methods described herein. In embodiments, prodrug moieties described in Murakami et al. J. Med Chem., 2011, 54, 5902; Sofia et al., J. Med Chem. 2010, 53, 7202; Lam et al. ACC, 2010, 54, 3187; Chang et al., ACS Med Chem Lett., 2011, 2, 130; Furman et al., Antiviral Res., 2011, 91, 120; Vernachio et al., ACC, 2011, 55, 1843; Zhou et al, AAC, 2011, 44, 76; Reddy et al., BMCL, 2010, 20, 7376; Lam et al., J. Virol., 2011, 85, 12334; Sofia et al., J. Med. Chem., 2012, 55, 2481, Hecker et al., J. Med. Chem., 2008, 51, 2328; or Rautio et al., Nature Rev. Drug. Discov., 2008, 7, 255, all of which are incorporated herein by reference in their entirety for all purposes, may be added to compounds described herein or used in methods described herein.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 (125I), or carbon-14 (14C). All isotopic variations of the compounds of the present disclosure, whether radioactive or not, are encompassed within the scope of the present disclosure.

The symbol "—" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental wellbeing. The treatment or amelioration of symptoms can be based on objective or subjective parameters; including the results of a physical examination, electrocardiogram, echocardiography, radio-imaging, nuclear scan, and/or stress testing, neuropsychiatric exams, and/or a psychiatric evaluation. For example, certain methods herein treat a neurodegenerative disease or a cardiomyopathy. In embodiments, certain methods herein treat Parkinson's disease by decreasing the production of Lewy bodies, decreasing the accumulation of alpha-synuclein, decreasing cell death, decreasing loss of dopamine-generating cells, decreasing loss of cells in the substantia nigra, decreasing loss of dopamine production, decreasing a symptom of Parkinson's disease, decreasing loss of motor function, decreasing shaking or slowing an increase in shaking (tremor), decreasing rigidity or an increase in rigidity, decreasing slowness (bradykinesia) of movement or a slowing of movement, decreasing sensory symptoms, decreasing insomnia, decreasing sleepiness, increasing mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival. In embodiments, certain methods herein treat cardiomyopathy by increasing cardiac performance, improving exercise tolerance, preventing heart failure, increasing blood oxygen content, or improving respiratory function. The term "treating" and conjugations thereof, include prevention of an injury, pathology, condition, or disease (e.g. preventing the development of one or more symptoms of a neurodegenerative disease such as Parkinson's disease, or of a cardiomyopathy).

A "complex I deficiency" refers to a disease chosen from Leigh Disease, Mitochondrial encephalomyopathy, lactic acidosis, and stroke-like episodes (MELAS), and Leber's Hereditary Optic Neuropathy.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "associated" or "associated with" in the context of a substance or substance activity or function associated with a disease (e.g. a protein associated disease, a symptom associated with a cardiomyopathy, neurodegenerative disease, or symptom associated with Parkinson's disease) means that the disease (e.g. cardiomyopathy, neurodegenerative disease or Parkinson's disease) is caused by (in whole or in part), or a symptom of the disease is caused by (in whole or in part) the substance or substance activity or function. For example, a symptom of a disease or condition associated with a reduction in the level of PINK1 activity may be a symptom that results (entirely or partially) from a reduction in the level of PINK1 activity (e.g. loss of function mutation or gene deletion or modulation of PINK1 signal transduction pathway). As used herein, what is described as being associated with a disease, if a causative agent, could be a target for treatment of the disease. For example, a disease associated with PINK1, may be treated with an agent (e.g. compound as described herein) effective for increasing the level of activity of PINK1.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. PINK1). In embodiments contacting includes allowing a compound described herein to interact with a protein or enzyme that is involved in a signaling pathway.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In embodiments inhibition refers to reduction of a disease or symptoms of disease. In embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The symbol "  " denotes the point of attachment of a chemical moiety to the remainder of a molecule or chemical formula.

As defined herein, the term "activation", "activate", "activating" and the like in reference to a protein-activator (e.g. agonist) interaction means positively affecting (e.g. increasing) the activity or function of the protein (e.g. PINK1) relative to the activity or function of the protein in the absence of the activator (e.g. compound described herein). In embodiments, activation refers to an increase in the activity of a signal transduction pathway or signaling pathway (e.g. PINK1 pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. reduction of the level of PINK1 activity or protein associated with a cardiomyopathy or a neurodegenerative disease such as Parkinson's disease). Activation may include, at least in part, partially or totally increasing stimulation, increasing or enabling activation, or activating, sensitizing, or up-regulating signal transduction or enzymatic activity or the amount of a protein (e.g. PINK1) that may modulate the level of another protein or increase cell survival (e.g. increase in PINK1 activity may increase cell survival in cells that may or may not have a reduction in PINK1 activity relative to a non-disease control).

The term "modulator" refers to a composition that increases or decreases the level of a target molecule or the function of a target molecule. In embodiments, the modulator is a modulator of PINK1. In embodiments, the modulator is a modulator of PINK1 and is a compound that reduces the severity of one or more symptoms of a disease associated with PINK1 (e.g. reduction of the level of PINK1 activity or protein associated with a cardiomyopathy, neurodegenerative disease such as Parkinson's disease). In embodiments, a modulator is a compound that reduces the severity of one or more symptoms of a cardiomyopathy or neurodegenerative disease that is not caused or characterized by PINK1 (e.g. loss of PINK1 function) but may benefit from modulation of PINK1 activity (e.g. increase in level of PINK1 or PINK1 activity).

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In embodiments, a patient is human.

"Disease" or "condition" refer to a state of being or health status of a patient or subject capable of being treated with a compound, pharmaceutical composition, or method provided herein. In embodiments, the disease is a disease related to (e.g. characterized by) a reduction in the level of PINK1. In embodiments, the disease is a disease characterized by loss of dopamine-producing cells (e.g. Parkinson's disease). In embodiments, the disease is a disease characterized by neurodegeneration. In embodiments, the disease is a disease characterized by neural cell death. In embodiments, the disease is a disease characterized by a reduction in the level of PINK1 activity. In embodiments, the disease is Parkinson's disease. In embodiments, the disease is a neurodegenerative disease. In embodiments, the disease is a cardiomyopathy.

As used herein, the term "cardiomyopathy" refers to a disease condition that adversely affects cardiac cell tissue leading to a measurable deterioration in myocardial function (e.g. systolic function, diastolic function). Dilated cardiomyopathy is characterized by ventricular chamber enlargement with systolic dysfunction and no hypertrophy. Hypertrophic cardiomyopathy, is a genetic disease transmitted as an autosomal dominant trait. Hypertrophic cardiomyopathy is morphologically characterized by a hypertrophied and non-dialated left ventricle. Restrictive cardiomyopathy is characterized by nondialated nonhypertrophied morphology with diminished ventricular volume leading to poor ventricular filling. Arrhythmogenic right ventricular cardiomyopathy is an inheritable heart disease characterized by myocardial electric instability. Unclassified cardiomyopathy is a category for cardiomyopathies that do not match the features of any one of the other types. Unclassified cardiomyopathies may have features of multiple types or, for example, have the features of fibroelastosis, noncompacted myocardium, or systolic dysfunction with minimal dilatation.

As used herein, the term "neurodegenerative disease" refers to a disease or condition in which the function of a subject's nervous system becomes impaired. Examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, epilepsy, Friedreich ataxia, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Shy-Drager syndrome, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), or Mitochondrial Parkinson's disease. In embodiments, dysautonomia is not a neurodegenerative disease.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. cardiomyopathy therapies including, for example, Angiotensin Converting Enzyme Inhibitors (e.g. Enalipril, Lisinopril), Angiotensin Receptor Blockers (e.g. Losartan, Valsartan), Beta Blockers (e.g. Lopressor, Toprol-XL), Digoxin, or Diuretics (e.g. Lasix; or Parkinson's disease therapies including, for example, levodopa, dopamine agonists (e.g. bromocriptine, pergolide, pramipexole, ropinirole, piribedil, cabergoline, apomorphine, lisuride), MAO-B inhibitors (e.g. selegiline or rasagiline), amantadine, anticholinergics, antipsychotics (e.g. clozapine), cholinesterase inhibitors, modafinil, or non-steroidal anti-inflammatory drugs.

The compound of the disclosure can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, J. Biomater Sci. Polym. Ed. 7:623¬645, 1995; as biodegradable and injectable gel formulations (see, e.g., Gao Pharm. Res. 12:857¬863, 1995); or, as microspheres for oral administration (see, e.g., Eyles, J. Pharm. Pharmacol. 49:669674, 1997). In embodiments, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions of the present disclosure can also be delivered as nanoparticles.

Pharmaceutical compositions provided by the present disclosure include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. PINK1), and/or reducing, eliminating, or slowing the progression of disease symptoms (e.g. symptoms of cardiomyopathy or a neurodegeneration such as symptoms of Parkinson's disease). Determination of a therapeutically effective amount of a compound of the disclosure is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cardiomyopathy or neurodegeneration such as Parkinson's disease and severity of such symptoms), kind of concurrent treatment, complications from the disease being treated or other health-related problems. Other therapeutic regimens or agents can be used in conjunction with the methods and compounds of Applicants' disclosure. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating a disease associated neurodegeneration (e.g. Parkinson's disease such as levodopa, dopamine agonists (e.g. bromocriptine, pergolide, pramipexole, ropinirole, piribedil, cabergoline, apomorphine, lisuride), MAO-B inhibitors (e.g. selegiline or rasagiline), amantadine, anticholinergics, antipsychotics (e.g. clozapine), cholinesterase inhibitors, modafinil, or non-steroidal anti-inflammatory drugs), or with adjunctive agents that may not be effective alone, but may contribute to the efficacy of the active agent.

The compounds described herein can be used in combination with one another, with other active agents known to be useful in treating a cardiomyopathy such as Angiotensin Converting Enzyme Inhibitors (e.g. Enalipril, Lisinopril), Angiotensin Receptor Blockers (e.g. Losartan, Valsartan), Beta Blockers (e.g. Lopressor, Toprol-XL), Digoxin, or Diuretics (e.g. Lasixdisease associated neurodegeneration (e.g. Parkinson's disease such as levodopa, dopamine agonists (e.g. bromocriptine, pergolide, pramipexole, ropinirole, piribedil, cabergoline, apomorphine, lisuride), MAO-B inhibitors (e.g. selegiline or rasagiline), amantadine, anticholinergics, antipsychotics (e.g. clozapine), cholinesterase inhibitors, modafinil, or non-steroidal anti-inflammatory drugs), or with adjunctive agents that may not be effective alone, but may contribute to the efficacy of the active agent.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In embodiments, the active and/or adjunctive agents may be linked or conjugated to one another. In embodiments, the compounds described herein may be combined with treatments for neurodegeneration such as surgery. In embodiments, the compounds described herein may be combined with treatments for cardiomyopathy such as surgery.

"PINK1" is used according to its common, ordinary meaning and refers to proteins of the same or similar names and functional fragments and homologs thereof. The term includes and recombinant or naturally occurring form of PINK1 (e.g. "PTEN induced putative kinase 1"; Entrez Gene 65018, OMTM 608309, UniProtKB Q9BXM7, and/or RefSeq (protein) NP_115785.1). The term includes PINK1 and variants thereof that maintain PINK1 activity (e.g. within at least 30%, 40%, 50%, 60%, 70%, 80%, 90%, 95%, or 100% activity compared to PINK1).

The term "neo-substrate" refers to a composition that is structurally similar to a composition that is a substrate for a protein or enzyme during the normal functioning of the protein or enzyme, but that is structurally distinct from the normal substrate of the protein or enzyme. In embodiments, the neo-substrate is a better substrate for the protein or enzyme than the normal substrate (e.g. the reaction kinetics are better (e.g. faster), binding is stronger, turnover rate is higher, reaction is more productive, equilibrium favors product formation). In embodiments, the neo-substrate is a derivative of adenine, adenosine, AMP, ADP, or ATP. In embodiments, the neo-substrate is a substrate for PINK1. In embodiments, the neo-substrate is an $N_6$ substituted adenine, adenosine, AMP, ADP, or ATP.

The term "derivative" as applied to a phosphate containing, monophosphate, diphosphate, or triphosphate group or moiety refers to a chemical modification of such group wherein the modification may include the addition, removal, or substitution of one or more atoms of the phosphate containing, monophosphate, diphosphate, or triphosphate group or moiety. In embodiments, such a derivative is a prodrug of the phosphate containing, monophosphate, diphosphate, or triphosphate group or moiety, which is converted to the phosphate containing, monophosphate, diphosphate, or triphosphate group or moiety from the derivative following administration to a subject, patient, cell, biological sample, or following contact with a subject, patient, cell, biological sample, or protein (e.g. enzyme). In an embodiment, a triphosphate derivative is a gamma-thio triphosphate. In an embodiment, a derivative is a phosphoramidate. In embodiments, the derivative of a phosphate containing, monophosphate, diphosphate, or triphosphate group or moiety is as described in Murakami et al. J. Med Chem., 2011, 54, 5902; Sofia et al., J. Med Chem. 2010, 53, 7202; Lam et al. ACC, 2010, 54, 3187; Chang et al., ACS Med Chem Lett., 2011, 2, 130; Furman et al., Antiviral Res., 2011, 91, 120; Vernachio et al., ACC, 2011, 55, 1843; Zhou et al, AAC, 2011, 44, 76; Reddy et al., BMCL, 2010, 20, 7376; Lam et al., J. Virol., 2011, 85, 12334; Sofia et al., J. Med. Chem., 2012, 55, 2481; Hecker et al., J. Med. Chem., 2008, 51, 2328; or Rautio et al., Nature Rev. Drug. Discov., 2008, 7, 255, all of which are incorporated herein by reference in their entirety for all purposes.

The term "mitochondrial dysfunction" is used in accordance with its ordinary meaning and refers to aberrant activity of function of the mitochondria, including for example aberrant respiratory chain activity, reactive oxygen species levels, calcium homeostasis, programmed cell death mediated by the mitochondria, mitochondrial fusion, mitochondrial fission, lipid concentrations in the mitochondrial membrane, and/or mitochondrial permeability transition. In some embodiments, mitochondrial dysfunction is responsible for the underlying cause of a complex I deficiency.

As used herein, the term "mitochondrial disease" refers to a disease, disorder, or condition in which the function of a subject's mitochondria becomes impaired or dysfunctional. Examples of mitochondrial diseases that may be treated with a compound or method described herein include Alzheimer's disease, amyotrophic lateral sclerosis, Asperger's Disorder, Autistic Disorder, bipolar disorder, cancer, Cardiomyopathy, Charcot Marie Tooth disease (CMT, including various subtypes such as CMT type 2b and 2b), Childhood Disintegrative Disorder (CDD), diabetes, epilepsy, Friedreich's Ataxia (FA), Hereditary motor and sensory neuropathy (HMSN), Huntington's Disease, Keams-Sayre Syndrome (KSS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, macular degeneration, Mitochondrial Myopathy, Lactacidosis, and Stroke (MELAS), mitochondrial neurogastrointestinal encephalomyopathy (MNGIE), motor neuron diseases, Myoclonic Epilepsy With Ragged Red Fibers (MERRF), Neuropathy, ataxia, retinitis pigmentosa, and ptosis (NARP), Parkinson's disease, Peroneal muscular atrophy (PMA), Pervasive Developmental Disorder Not Otherwise Specified (PDD-NOS), renal tubular acidosis, Rett's Disorder, Schizophrenia, and types of stroke.

The term "oxidative stress" is used in accordance with its ordinary meaning and refers to aberrant levels of reactive oxygen species.

As used herein, the term "animal" includes, but is not limited to, humans and non-human vertebrates such as wild, domestic, and farm animals.

As used herein, the term "antagonize" or "antagonizing" means reducing or completely eliminating an effect, such as an activity of GPR109a.

As used herein, the phrase "anti-receptor effective amount" of a compound can be measured by the anti-receptor effectiveness of the compound. In some embodiments, an anti-receptor effective amount inhibits an activity of the receptor by at least 10%, by at least 20%, by at least 30%, by at least 40%, by at least 50%, by at least 60%, by at least 70%, by at least 80%, by at least 90%, or by at least 95%. In some embodiments, an "anti-receptor effective amount" is also a "therapeutically effective amount" whereby the compound reduces or eliminates at least one effect of GPRI09a. In some embodiments, the effect is the B-arrestin effect. In some embodiments, the effect is the G-protein mediated effect.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system. For example, "contacting" a compound disclosed herein with an individual or patient or cell includes the administration of the compound to an individual or patient, such as a human, as well as, for example, introducing a compound into a sample containing a cellular or purified preparation containing the compounds or pharmaceutical compositions disclosed herein.

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "inhibiting activity," such as enzymatic or receptor activity means reducing by any measurable amount the activity of PINK1.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the phrase "integer from X to Y" means any integer that includes the endpoints. For example, the phrase "integer from 1 to 5" means 1, 2, 3, 4, or 5.

As used herein, the term "isolated" means that the compounds described herein are separated from other components of either (a) a natural source, such as a plant or cell, or (b) a synthetic organic chemical reaction mixture, such as by conventional techniques.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfate, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present disclosure also includes quaternary ammonium salts of the compounds described herein, where the compounds have one or more tertiary amine moiety.

As used herein, the terms "prevention" or "preventing" mean a reduction of the risk of acquiring a particular disease, condition, or disorder.

As used herein, the term "prodrug" means a derivative of a known direct acting drug, which derivative has enhanced delivery characteristics and therapeutic value as compared to the drug, and is transformed into the active drug by an enzymatic or chemical process. The compounds described herein also include derivatives referred to as prodrugs, which can be prepared by modifying functional groups present in the compounds in such a way that the modifications are cleaved, either in routine manipulation or in vivo, to the parent compounds. Examples of prodrugs include compounds of the disclosure as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the disclosure. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

As used herein, the term "purified" means that when isolated, the isolate contains at least 90%, at least 95%, at least 98%, or at least 99% of a compound described herein by weight of the isolate.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. For purposes of this disclosure, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of flushing" or "treating flushing" means an activity that prevents, alleviates or ameliorates any of the primary phenomena or secondary symptoms associated with the flushing.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

It is understood that the present disclosure encompasses the use, where applicable, of stereoisomers, diastereomers and optical stereoisomers of the compounds of the disclosure, as well as mixtures thereof. Additionally, it is understood that stereoisomers, diastereomers, and optical stereoisomers of the compounds of the disclosure, and mixtures thereof, are within the scope of the disclosure. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

It should be noted that any embodiment of the disclosure can optionally exclude one or more embodiment for purposes of claiming the subject matter. For instance, the disclosure relates to those compounds having formula The compounds described herein can be asymmetric (e.g., having one or more stereocenters). All stereoisomers, such as enantiomers and diastereomers, are intended to be included within the scope of the disclosure unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds are also included within the scope of the disclosure and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of a-methylbenzylamine (e.g., S and R forms, or diastereomerically pure forms), 2-phenylglycinol, norephedrine, ephedrine, N-methylephedrine, cyclohexylethylamine, 1, 2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1, 2, 4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

In some embodiments, the compounds, or salts thereof or compositions comprising the same do not comprise one or a combination of any of the embodiments listed herein.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

Embodiments of various compounds and salts thereof are provided. Where a variable is not specifically recited, the variable can be any option described herein, except as otherwise noted or dictated by context.

In some embodiments, the disclosure relates to a compound having the following formula or pharmaceutically acceptable salt thereof:

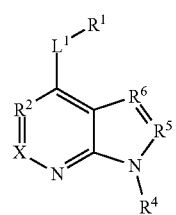

wherein X is independently selected from a carbon with a —CH, —CHCH$_3$, substituted or unsubstituted cycloalkyl, substituted or unsubstituted heterocycloalkyl, substituted or unsubstituted aryl, or substituted or unsubstituted heteroaryl; L$^1$ is a bond, substituted or unsubstituted alkylene, or substituted or unsubstituted heteroalkylene;

R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R⁴ is hydrogen, substituted or unsubstituted cycloalkyl, substituted or unsubstituted heterocycloalkyl, substituted or unsubstituted aryl, or substituted or unsubstituted heteroaryl; and wherein if $R^4$ is hydrogen, then -$L^1$-$R^1$ is not hydrogen,

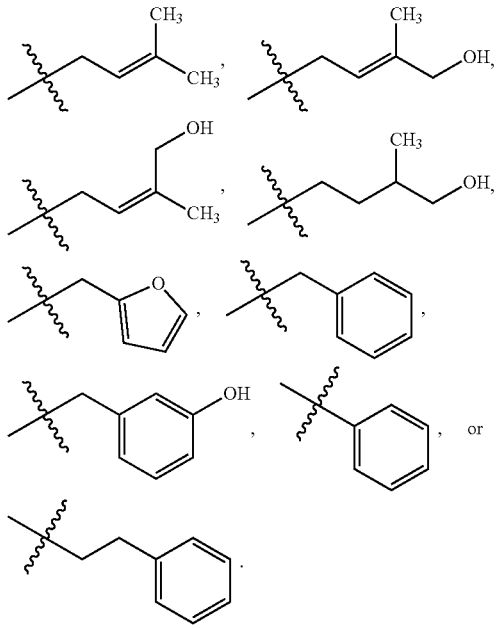

In some embodiments, X independently selected from a carbon with a methyl, ethyl, or butyl group. In some embodiments, X is independently selected from

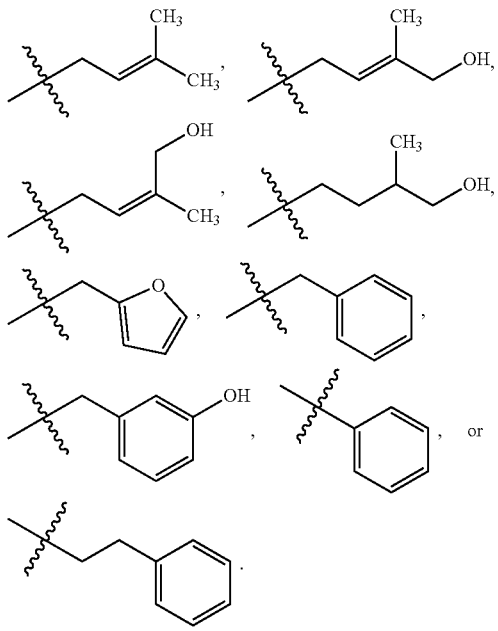

In some embodiments, X is a carbon with a methyl group. In some embodiments, X is independently a carbon with a hydrogen, oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, X is independently selected from a substituted or unsubstituted tetrahydrofuranyl, substituted or unsubstituted 2, 5-dihydrofuranyl, substituted or unsubstituted tetrahydrothienyl, substituted or unsubstituted 2, 5-dihydrothienyl, substituted or unsubstituted pyrrolidinyl, substituted or unsubstituted 2, 5-dihydro-1H-pyrrolyl, substituted or unsubstituted cyclopentyl, substituted or unsubstituted cyclopentenyl, or substituted or unsubstituted 1, 3-oxathiolanyl. In some embodiments, R⁴ is independently hydrogen, substituted or unsubstituted cycloalkyl, substituted or unsubstituted heterocycloalkyl, substituted or unsubstituted aryl, or substituted or unsubstituted heteroaryl.

In some embodiments, R⁴ is independently substituted with at least one oxo; halogen; —OH; —CH₂OH; —N₃; or monophosphate, diphosphate, triphosphate, or a derivative thereof.

In some embodiments, R⁴ has the formula:

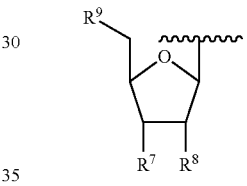

wherein,
$R^7$ and $R^8$ are independently be hydrogen, oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^9$ is hydrogen, oxo, halogen, —CF₃, —CN, —OH, —NH₂, —COOH, —CONH₂, —NO₂, —SH, —SO₂C₁, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted phosphate, substituted or unsubstituted monophosphate, substituted or unsubstituted diphosphate, or substituted or unsubstituted triphosphate.

In some embodiments, $R^7$ and $R^8$ are independently hydrogen or —OH; and $R^9$ is a —OH, monophosphate, diphosphate, triphosphate, or a derivative thereof.

In some embodiments, the compounds of the present disclosure does not comprise kinetin or any molecule comprising the monophosphate, diphosphate, triphosphate, or a derivative thereof based upon its position at the R⁴ position. Kinetin has the following formula:

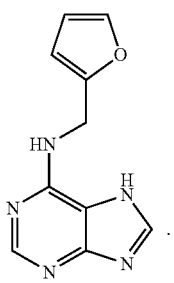

In some embodiments, the disclosure relates to a compound having formula:

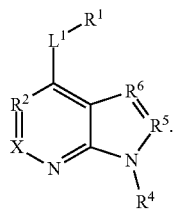

wherein X is independently selected from a carbon with a —CH, —CHCH$_3$, substituted or unsubstituted cycloalkyl, substituted or unsubstituted heterocycloalkyl, substituted or unsubstituted aryl, or substituted or unsubstituted heteroaryl; L$^1$ is a bond, substituted or unsubstituted alkylene, or substituted or unsubstituted heteroalkylene;

R$^{1-}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^4$ is hydrogen, substituted or unsubstituted cycloalkyl, substituted or unsubstituted heterocycloalkyl, substituted or unsubstituted aryl, or substituted or unsubstituted heteroaryl; R$^2$ is an amino group;
R$^5$ is a saturated carbon atom; and
R$^6$ is an amino group.

In some embodiments, the disclosure relates to a compound having formula:

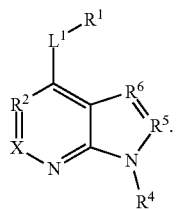

wherein X is independently selected from a carbon with a —CH, —CHCH$_3$, substituted or unsubstituted cycloalkyl, substituted or unsubstituted heterocycloalkyl, substituted or unsubstituted aryl, or substituted or unsubstituted heteroaryl; L$^1$ is a bond, substituted or unsubstituted alkylene, or substituted or unsubstituted heteroalkylene;

R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^4$ is hydrogen, substituted or unsubstituted cycloalkyl, substituted or unsubstituted heterocycloalkyl, substituted or unsubstituted aryl, or substituted or unsubstituted heteroaryl;
R$^2$ is an amino group;
R$^5$ is a saturated carbon atom; and
R$^6$ is an amino group; and wherein if R$^4$ is hydrogen, then -L$^1$-R$^1$ is not hydrogen,

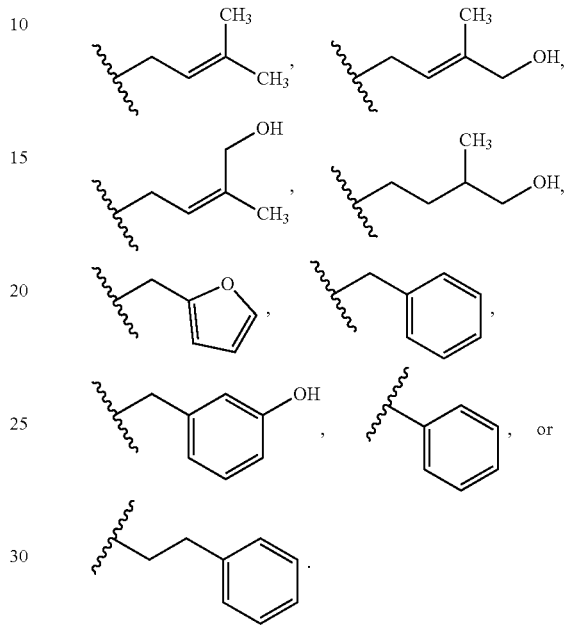

In some embodiments, the disclosure relates to a compound having formula:

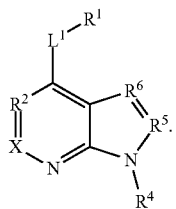

wherein X is independently selected from a carbon with a —CH, —CHCH$^3$, substituted or unsubstituted cycloalkyl, substituted or unsubstituted heterocycloalkyl, substituted or unsubstituted aryl, or substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, unsubstituted pyrrolidinyl, substituted or unsubstituted 2,5-dihydro-1H-pyrrolyl, substituted or unsubstituted cyclopentyl, substituted or unsubstituted cyclopentenyl, substituted or unsubstituted 1,3-oxathiolanyl, independently be R$^{99}$-substituted, where R$^{99}$ is as described herein, including embodiments thereof.

$L^1$ is a bond, substituted or unsubstituted alkylene, or substituted or unsubstituted heteroalkylene;

$R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is hydrogen, substituted or unsubstituted cycloalkyl, substituted or unsubstituted heterocycloalkyl, substituted or unsubstituted aryl, or substituted or unsubstituted heteroaryl;

$R^2$ is an amine group;

$R^5$ is a saturated carbon atom; and $R^6$ is an amine group; and wherein the compound is not a compound disclosed in U.S. Patent Application No. 61/763,444, filed Feb. 11, 2013, U.S. Patent Application No. 61/845,529, filed Jul. 12, 2103, or PCT Application No. PCT/US2014/015863, filed Feb. 11, 2014, or any non-provisional application, filed Feb. 11, 2014, claiming priority to thereto.

Provided herein are compositions having the formula:

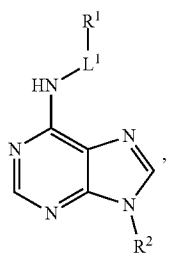
(I)

wherein $L^1$ is a bond, substituted or unsubstituted alkylene, or substituted or unsubstituted heteroalkylene. $R^{1-}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, substituted or unsubstituted cycloalkyl, substituted or unsubstituted heterocycloalkyl, substituted or unsubstituted aryl, or substituted or unsubstituted heteroaryl. In some embodiments, if $R^4$ is hydrogen, then $-L^1-R^1$ is not hydrogen,

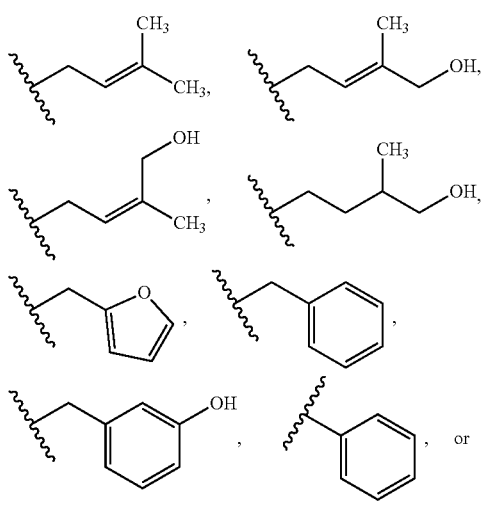

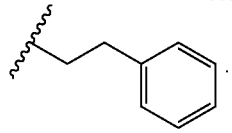

In some embodiments, the disclosure relates to a compound having formula:

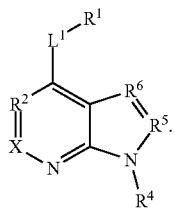

wherein X is independently selected from a carbon with a —CH, —CHCH$_3$, substituted or unsubstituted cycloalkyl, substituted or unsubstituted heterocycloalkyl, substituted or unsubstituted aryl, or substituted or unsubstituted heteroaryl;

$L^1$ is a bond, substituted or unsubstituted alkylene, or substituted or unsubstituted heteroalkylene;

$R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is hydrogen, substituted or unsubstituted cycloalkyl, substituted or unsubstituted heterocycloalkyl, substituted or unsubstituted aryl, or substituted or unsubstituted heteroaryl;

$R^2$ is an amine group;

$R^5$ is a saturated carbon atom; and $R^6$ is an amino group; and wherein if $R^4$ is hydrogen, then $-L^1-R^1$ is not hydrogen,

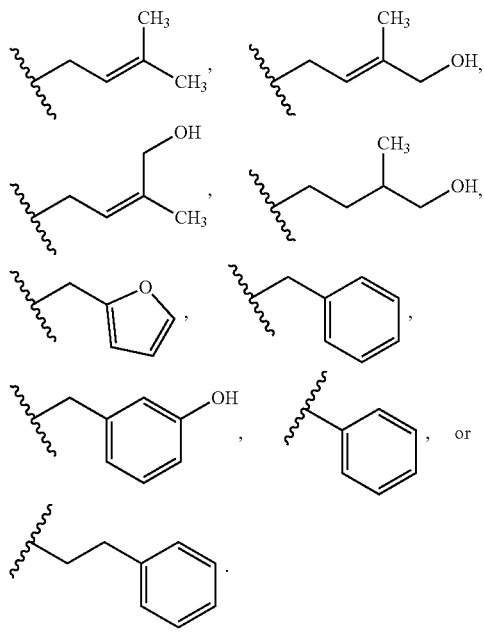

Provided herein are pharmaceutical compositions which include a pharmaceutically acceptable excipient and a compound of any of the formulas or embodiments provided herein, including pharmaceutically acceptable salts thereof.

Provided herein are methods of treating or preventing a neurodegenerative disease in a subject in need thereof by administering pharmaceutical compositions which include a pharmaceutically acceptable excipient and therapeutically effective amounts of a compound of any of the formulas or embodiments provided herein, including pharmaceutically acceptable salts thereof.

Provided herein are methods of treating or preventing a mitochondrial disease in a subject in need thereof by administering pharmaceutical compositions which include a pharmaceutically acceptable excipient and therapeutically effective amounts of a compound of any of the formulas or embodiments provided herein, including pharmaceutically acceptable salts thereof.

Provided herein are methods of treating or preventing a complex I deficiency in a subject in need thereof by administering pharmaceutical compositions which include a pharmaceutically acceptable excipient and therapeutically effective amounts of a compound of any of the formulas or embodiments provided herein, including pharmaceutically acceptable salts thereof.

Provided herein are methods of treating or preventing Parkinson's disease in a subject in need thereof by administering pharmaceutical compositions which include a pharmaceutically acceptable excipient and therapeutically effective amounts of a compound of any of the formulas or embodiments provided herein, including pharmaceutically acceptable salts thereof.

Provided herein are methods of treating or preventing Leigh's disease in a subject in need thereof by administering pharmaceutical compositions which include a pharmaceutically acceptable excipient and therapeutically effective amounts of a compound of any of the formulas or embodiments provided herein, including pharmaceutically acceptable salts thereof.

In some embodiments, the compound and the use of such compound in any of the methods provided herein is kinetin or a pharmaceutically acceptable salt thereof.

In some embodiments, the disclosure provides a compound having the following formula or pharmaceutically acceptable salt thereof:

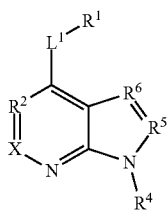

wherein X is independently selected from a carbon with a —CH, —CHCH$_3$, substituted or unsubstituted cycloalkyl, substituted or unsubstituted heterocycloalkyl, substituted or unsubstituted aryl, or substituted or unsubstituted heteroaryl;
L$^{1-}$ is a bond, substituted or unsubstituted alkylene, or substituted or unsubstituted heteroalkylene;
R$^{1-}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^4$ is hydrogen, substituted or unsubstituted cycloalkyl, substituted or unsubstituted heterocycloalkyl, substituted or unsubstituted aryl, or substituted or unsubstituted heteroaryl;
R$^2$ is independently selected from a —CH or N;
R$^5$ is a saturated carbon atom or amine; and
R$^6$ is a saturated carbon atom or N.

In some embodiments, the disclosure relates to a compound having formula:

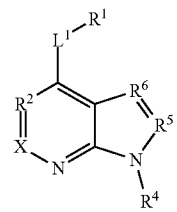

wherein X is independently selected from a —CH, —CHCH$_3$, or a carbon with a substituted or unsubstituted cycloalkyl, substituted or unsubstituted heterocycloalkyl, substituted or unsubstituted aryl, or substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, unsubstituted pyrrolidinyl, substituted or unsubstituted 2,5-dihydro-1H-pyrrolyl, substituted or unsubstituted cyclopentyl, substituted or unsubstituted cyclopentenyl, substituted or unsubstituted 1,3-oxathiolanyl, independently be R$^{99}$-substituted, where R$^{99}$ is as described herein, including embodiments thereof. L$^1$ is a bond, substituted or unsubstituted alkylene, or substituted or unsubstituted heteroalkylene;
R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^4$ is hydrogen, substituted or unsubstituted cycloalkyl, substituted or unsubstituted heterocycloalkyl, substituted or unsubstituted aryl, or substituted or unsubstituted heteroaryl;
R$^2$ is an amine group;
R$^5$ is a saturated carbon atom; and
R$^6$ is an amino group; and wherein the compound is not a compound disclosed in paragraphs [0115]-[0117] of U.S. Patent Application No. 61/763,444, filed Feb. 11, 2013, U.S. Patent Application No. 61/845,529, filed Jul. 12, 2103, or PCT Application No. PCT/US2014/015863, filed Feb. 11, 2014, or any non-provisional application, filed Feb. 11, 2014, claiming priority to thereto.

In some embodiments, the disclosure relates to a compound having formula:

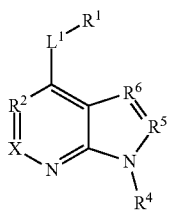

wherein X is independently selected from a —CH, —CHCH₃, or a carbon with a substituted or unsubstituted cycloalkyl, substituted or unsubstituted heterocycloalkyl, substituted or unsubstituted aryl, or substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, unsubstituted pyrrolidinyl, substituted or unsubstituted 2,5-dihydro-1H-pyrrolyl, substituted or unsubstituted cyclopentyl, substituted or unsubstituted cyclopentenyl, substituted or unsubstituted 1,3-oxathiolanyl, independently be $R^{99}$-substituted, where $R^{99}$ is as described herein, including embodiments thereof. $L^1$ is a bond, substituted or unsubstituted alkylene, or substituted or unsubstituted heteroalkylene;

$R^{1-}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is hydrogen, substituted or unsubstituted cycloalkyl, substituted or unsubstituted heterocycloalkyl, substituted or unsubstituted aryl, or substituted or unsubstituted heteroaryl;

$R^2$ is an amine group;

$R^5$ is a saturated carbon atom; and $R^6$ is an amine group; and wherein the compound is not a compound disclosed in paragraphs [0115]-[0117] of U.S. Patent Application No. 61/763,444, filed Feb. 11, 2013, U.S. Patent Application No. 61/845,529, filed Jul. 12, 2103, or PCT Application No. PCT/US2014/015863, filed Feb. 11, 2014, or any non-provisional application, filed Feb. 11, 2014, claiming priority to thereto.

In some embodiments, the disclosure relates to a compound having formula:

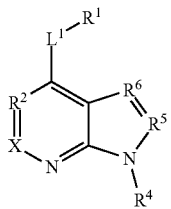

wherein X is independently selected from a —CH, —CHCH₃, or a carbon with a substituted or unsubstituted cycloalkyl, substituted or unsubstituted heterocycloalkyl, substituted or unsubstituted aryl, or substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, unsubstituted pyrrolidinyl, substituted or unsubstituted 2,5-dihydro-1H-pyrrolyl, substituted or unsubstituted cyclopentyl, substituted or unsubstituted cyclopentenyl, substituted or unsubstituted 1,3-oxathiolanyl, independently be $R^{99}$-substituted, where $R^{99}$ is as described herein, including embodiments thereof.

$L^{1-}$ is a bond, substituted or unsubstituted alkylene, or substituted or unsubstituted heteroalkylene;

$R^{1-}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is hydrogen, substituted or unsubstituted cycloalkyl, substituted or unsubstituted heterocycloalkyl, substituted or unsubstituted aryl, or substituted or unsubstituted heteroaryl;

$R^2$ is an amino group;

$R^5$ is a saturated carbon atom; and $R^6$ is an amino group; and wherein the compound is not an embodiment disclosed in paragraphs [0115]-[0117] of U.S. Patent Application No. 61/763,444, filed Feb. 11, 2013, U.S. Patent Application No. 61/845,529, filed Jul. 12, 2103, or PCT Application No. PCT/US2014/015863, filed Feb. 11, 2014, or any non-provisional application, filed Feb. 11, 2014, claiming priority to thereto.

In some embodiments, the disclosure relates to a compound having formula:

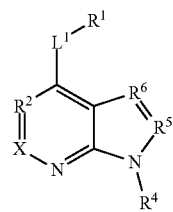

wherein X is independently selected from a —CH, —CHCH₃, or a carbon with a substituted or unsubstituted cycloalkyl, substituted or unsubstituted heterocycloalkyl, substituted or unsubstituted aryl, or substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, unsubstituted pyrrolidinyl, substituted or unsubstituted 2,5-dihydro-1H-pyrrolyl, substituted or unsubstituted cyclopentyl, substituted or unsubstituted cyclopentenyl, substituted or unsubstituted 1,3-oxathiolanyl, independently be $R^{99}$-substituted, where $R^{99}$ is as described herein, including embodiments thereof.

$L^1$ is a bond, substituted or unsubstituted alkylene, or substituted or unsubstituted heteroalkylene;

$R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is hydrogen, substituted or unsubstituted cycloalkyl, substituted or unsubstituted heterocycloalkyl, substituted or unsubstituted aryl, or substituted or unsubstituted heteroaryl;

$R^2$ is an N;

$R^5$ is an N; and $R^6$ is a saturated carbon atom.

In some embodiments, the disclosure relates to a compound having formula:

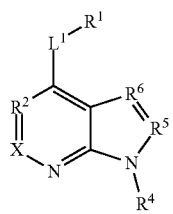

wherein X is C—CH$_3$; $L^1$ is NH; $R^{1-}$ is CH$_2$(2,5-dihydrofuranyl)-$R^{99}$;

$R^2$ is N;

$R^4$ is hydrogen;

$R^5$ is N; and $R^6$ is CH;

wherein $R^{99}$ is independently a hydrogen, methyl group, methoxy group, oxo, halogen, —CF$_3$, —CN, —OH, —NH$_2$, —COOH, —CONH$_2$, —NO$_2$, —SH, —SO$_2$C$_1$, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)—OH, —NHOH, —OCF$_2$, OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, or substituted or unsubstituted triphosphate. In some embodiments, $R^{99}$ is independently a methoxy group. In some embodiments, $R^{99}$ is independently a hydrogen. In some embodiments, $R^{99}$ is independently a methyl group.

In some embodiments, the disclosure relates to a compound having formula:

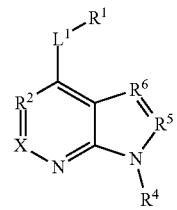

wherein X is independently selected from a —CH, —CHCH$_3$, or a carbon with a substituted or unsubstituted cycloalkyl, substituted or unsubstituted heterocycloalkyl, substituted or unsubstituted aryl, or substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, unsubstituted pyrrolidinyl, substituted or unsubstituted 2,5-dihydro-1H-pyrrolyl, substituted or unsubstituted cyclopentyl, substituted or unsubstituted cyclopentenyl, substituted or unsubstituted 1, 3-oxathiolanyl, independently be $R^{99}$-substituted, where $R^{99}$ is as described herein, including embodiments thereof.

$L^1$ is a bond, substituted or unsubstituted alkylene, or substituted or unsubstituted heteroalkylene;

$R^{1-}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is hydrogen, substituted or unsubstituted cycloalkyl, substituted or unsubstituted heterocycloalkyl, substituted or unsubstituted aryl, or substituted or unsubstituted heteroaryl;

$R^2$ is an NH;

$R^5$ is a saturated carbon atom; and $R^6$ is an amino group; and wherein the compound is not a compound disclosed with the formula:

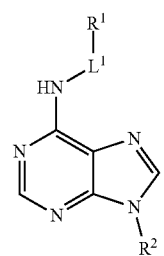

(Formula Ia.)

wherein $L^1$ is a bond, substituted or unsubstituted alkylene, or substituted or unsubstituted heteroalkylene;

$R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R⁴ is hydrogen, substituted or unsubstituted cycloalkyl, substituted or unsubstituted heterocycloalkyl, substituted or unsubstituted aryl, or substituted or unsubstituted heteroaryl; and wherein if R⁴ is hydrogen, then is not hydrogen,

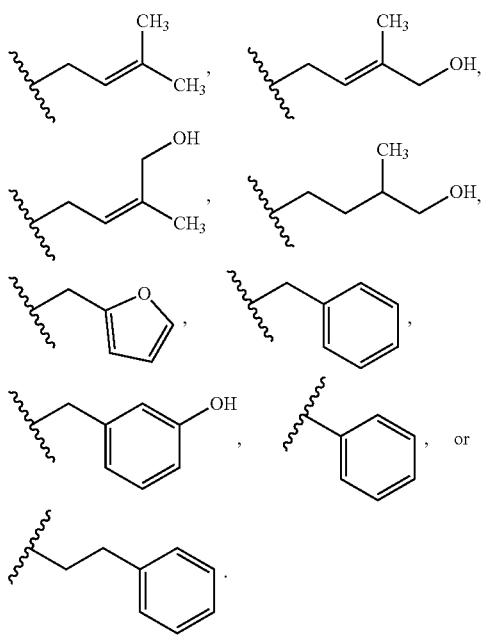

In some embodiments, the compound of the present disclosure has the formula:

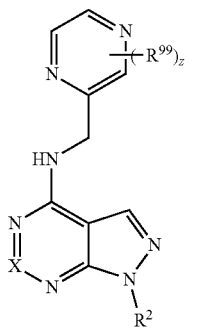

wherein X is independently selected from a —CH, —CHCH₃, or a carbon with a substituted or unsubstituted cycloalkyl, substituted or unsubstituted heterocycloalkyl, substituted or unsubstituted aryl, or substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, unsubstituted pyrrolidinyl, substituted or unsubstituted 2,5-dihydro-1H-pyrrolyl, substituted or unsubstituted cyclopentyl, substituted or unsubstituted cyclopentenyl, substituted or unsubstituted 1,3-oxathiolanyl, independently R⁹⁹-substituted, where R⁹⁹ is as described herein, including embodiments thereof.

wherein R² is H; and the symbol z is an integer independently selected from 0, 1, 2, 3, 4, or 5;

wherein R⁹⁹ is independently a hydrogen, methyl group, methoxy group, oxo, halogen, —CF₃, —CN, —OH, —NH₂, —COOH, —CONH₂, —NO₂, —SH, —SO₂C₁, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, or substituted or unsubstituted triphosphate. In some embodiments, R⁹⁹ is independently a hydrogen.

In some embodiments, the present disclosure provides a compound having the Formula:

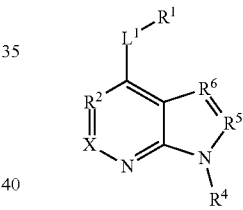

wherein X is CH or C—CH₃; L¹ is NH; R⁶ is a saturated carbon; R⁴ is hydrogen, substituted or unsubstituted cycloalkyl, substituted or unsubstituted heterocycloalkyl, substituted or unsubstituted aryl, or substituted or unsubstituted heteroaryl; R⁵ is a N; and R¹ is C (2,5-dihydrofuranyl)-R⁹⁹;

wherein R⁹⁹ is independently a hydrogen, methyl group, methoxy group, oxo, halogen, —CF₃, —CN, —OH, —NH₂, —COOH, —CONH₂, —NO₂, —SH, —SO₂C₁—SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, or substituted or unsubstituted triphosphate. In some embodiments, $R^{99}$ is a methoxy group. In some embodiments, $R^{99}$ is a hydrogen. In some embodiments, $R^{99}$ is a methyl group.

In some embodiments, the present disclosure provides a compound having the Formula:

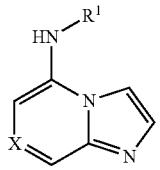

wherein X is independently a carbon with a hydrogen, methyl group, methoxy group, oxo, halogen, —$CF_3$, —CN, —OH, —$NH_2$, —COOH, —$CONH_2$, —$NO_2$, —SH, —$SO_2C_1$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)-OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, or substituted or unsubstituted triphosphate;

wherein $R^1$ is independently selected from a hydrogen, methyl group, methoxy group, oxo, halogen, —$CF_3$, —CN, —OH, —$NH_2$, —COON, —$CONH_2$, —$NO_2$, —SH, —$SO_2C_1$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, or $CH_2$ (2,5-dihydrofuranyl)-$R^{99}$; and $R^{99}$ is independently sleeted from a hydrogen, methyl group, methoxy group, oxo, halogen, —$CF_3$, —CN, —OH, —$NH_2$, —COOH, —$CONH_2$, —$NO_2$, —SH, —$SO_2C_1$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, substituted or unsubstituted triphosphate. In some embodiments, X is independently a carbon with a hydrogen. In some embodiments, $R^{99}$ is independently a hydrogen. In some embodiments, the present disclosure provides a compound having the Formula:

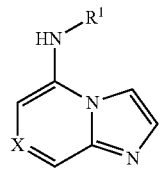

wherein X is independently a carbon with a hydrogen, methyl group, methoxy group, oxo, halogen, —$CF_3$, —CN, —OH, —$NH_2$, —COOH, —$CONH_2$, —$NO_2$, —SH, —$SO_2C_1$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, or substituted or unsubstituted triphosphate;

wherein $R^1$ is $CH_2$ (2,5-dihydrofuranyl)-$R^{99}$;

wherein $R^{99}$ is independently a hydrogen, methyl group, methoxy group, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, substituted or unsubstituted triphosphate. In some embodiments, X is independently a carbon with a hydrogen. In some embodiments, R$^{99}$ is independently a hydrogen.

In some embodiments, the present disclosure provides a compound having the Formula:

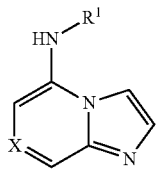

wherein X is independently a carbon with a hydrogen, methyl group, methoxy group, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, substituted or unsubstituted triphosphate, or R$^{99}$-substituted, where R$^{99}$ is described herein, including embodiments thereof;
wherein R$^1$ is (2,5-dihydrofuranyl)-R$^{99}$;
wherein R$^{99}$ is independently a hydrogen, methyl group, methoxy group, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted phosphate, substituted or unsubstituted monophosphate, substituted or unsubstituted diphosphate, substituted or unsubstituted triphosphate. In some embodiments, X is independently a carbon with a hydrogen.

In a first aspect is provided a method of treating a neurodegenerative disease in a patient in need thereof, the method including administering a therapeutically effective amount of a compound to the patient, wherein the compound has the formula:

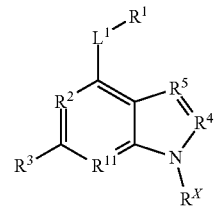

(Ib). L$^1$ is a bond, substituted or unsubstituted alkylene, substituted or unsubstituted alkenyl, substituted or unsubstituted alkynyl, or substituted or unsubstituted heteroalkylene. R$^1$ is hydrogen, oxo, halogen, —CX$_3$, —CN, —SO$_2$Cl, —SO$_n$R$^{10}$, —SO$_v$NR$^7$R$^8$, —NHNH$_2$, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$OR$^{10}$, —N(R$^7$)C=(O)R$^9$, —NR$^7$C(O)—OR$^9$, —NR$^7$OR$^9$, —OCX$_3$, —OCHX$_2$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^2$, R$^4$, R$^5$, R$^{11}$ are independently-N—CH, —CD, or —C-L$^1$-R$^6$ where in R$^6$ is independently halogen, —CF$_3$, —CN, —OH, —NH$_2$, —COOH, —CONH$_2$, —NO$_2$, —SH, —SO$_2$Cl, —SO$_3$H, —SO$_4$H—SO$_2$NH$_2$, SO$_n$OR$^{10}$, —SO$_v$NR$^7$R$^8$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$OR$^{10}$, —N(R$^7$)C=(O)R$^9$, —NR$^7$C(O)—OR$^9$, —NR$^7$OR$^9$, —OCX$_3$, —OCHX$_2$, —OCF$_3$, —OCHF$_2$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R$^7$ and R$^8$ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F.

R$^3$ is independently H, D, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, SO$_n$R$^{10}$, —SO, NR$^7$R$^8$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$OR$^{10}$, —N(R$^7$)C=(O)R$^9$, —NR$^7$C(O)—OR$^9$, —NR$^7$OR$^9$, —OCX$_3$, —OCHX$_2$, —OCF$_3$, —OCHF$_2$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R$^7$ and R$^8$ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F.

R$^x$ is hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl.

R$^7$, R$^8$, R$^9$, and Rm are independently hydrogen, deuterium, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R$^7$ and R$^8$ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F.

In some embodiments, the disclosure provides a method of treating or preventing a neurodegenerative disease in a subject in need thereof comprising administering to the subject a therapeutically effective amount of any compound disclosed herein or a pharmaceutically acceptable salt thereof. In some embodiments, the disclosure provides a method of treating or preventing a neurodegenerative disease in a subject in need thereof comprising administering to the subject a therapeutically effective amount of kinetin or a pharmaceutically acceptable salt thereof.

In some embodiments, the disclosure provides a method of treating or preventing Leigh disease in a subject in need thereof comprising administering to the subject a therapeutically effective amount of any compound disclosed herein or a pharmaceutically acceptable salt thereof.

In some embodiments, the disclosure provides a method of treating or preventing Leigh disease in a subject in need thereof comprising administering to the subject a therapeutically effective amount of kinetin or a pharmaceutically acceptable salt thereof.

In some embodiments, the disclosure provides a method of treating or preventing a complex I deficiency in a subject in need thereof comprising administering to the subject a therapeutically effective amount of any compound disclosed herein or a pharmaceutically acceptable salt thereof. In some embodiments, the disclosure provides a method of treating or preventing a complex I deficiency in a subject in need thereof comprising administering to the subject a therapeutically effective amount of kinetin or a pharmaceutically acceptable salt thereof.

In some embodiments, the compound is not kinetin. In some embodiments, the compound does not include compounds of the following formula:

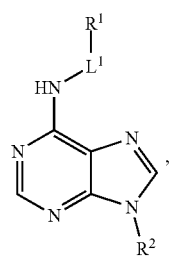

(I)

wherein L$^1$ is a bond, substituted or unsubstituted alkylene, or substituted or unsubstituted heteroalkylene. R$^1$ is hydrogen, oxo, halogen, —CX$_3$, —CN, —SO$_2$Cl, —SO$_n$OR$^{10}$, —SO$_v$NR$^7$R$^8$, —NHNH$_2$, —ONR$^7$R$^8$, —NHC(O)NHNH$_2$, —NHC(O)NR$^7$R$^8$, —N(O)$_m$, —NR$^7$R$^8$, —C(O)R$^9$, —C(O)OR$^9$, —C(O)NR$^7$R$^8$, —OR$^{10}$, NR$^7$SO$_2$R$^{10}$, —N(R$^7$)C(O)R$^9$, —NR$^7$C(O)—OR$^9$, —NR$^7$OR$^9$, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is hydrogen, substituted or unsubstituted cycloalkyl, substituted or unsubstituted heterocycloalkyl, substituted or unsubstituted aryl, or substituted or unsubstituted heteroaryl. R$^7$, R$^8$, R$^9$, and R$^{10}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R$^7$ and R$^8$ are bonded to the same nitrogen atom, they may optionally be joined to form a substituted or unsubstituted heterocycloalkyl or substituted or unsubstituted heteroaryl; wherein the symbols m and v are independently 1 or 2.; and wherein the symbol n is independently an integer from 0 to 4; and wherein the symbol X is independently —Cl, —Br, —I, or —F.

In some embodiments, the disclosure provides a compound of formula:

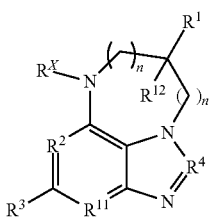

(IIa)

wherein R$^1$ is hydrogen, deuterium, oxo, halogen, —CX$_3$, —CN, —SO$_2$Cl, —SO$_2$, OR$^{10}$, —SO$_2$NR$^7$R$^8$, —NHNH$_2$, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$R$^{10}$, —N(R$^7$)C=(O)R$^9$, —NR$^7$C(O)—OR$^9$, —NR$^7$OR$^9$, —OCX$_3$, —OCHX$_2$, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^2$, R$^4$, R$^{11}$ are independently —N, —CH, —CD, or —C-L$^1$-R$^6$ where in R$^6$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —SO$_v$NR$^7$R$^8$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —ONR$^7$R$^8$, —NHC=(O)NHNH$_2$, —NHC=(O)NR$^7$R$^8$, N(O)$_m$, —NR$^7$R$^8$, —C(O)R$^9$, —C(O)OR$^9$, —C(O)NR$^7$R$^8$, —OR$^{10}$, —NR$^7$SO$_2$OR$^{10}$, —N(R$^7$)C=(O)

R⁹, —NR⁷C(O)—OR⁹, —NR⁷OR⁹, —OCX₃, —OCHX₂, —OCF₃, —OCHF₂, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F.

R³ is independently H, D, halogen, —CF₃, —CN, —OH, —NH₂, —COOH, —CONH₂, —NO₂, —SH, —SO₂Cl, —SO₃H, —SO₄H, —SO₂NH₂, SO$_n$R¹⁰, —SO$_v$NR⁷R⁸, —NHNH₂, —ONH₂, —NHC═(O)NHNH₂, —NHC═(O)NH₂, —NHSO₂H, —NHC═(O)H, —NHC(O)—OH, —NHOH, —ONR⁷R⁸, —NHC═(O)NHNH₂, —NHC═(O)NR⁷R⁸, —N(O)$_m$, —NR⁷R⁸, —C(O)R⁹, —C(O)OR⁹, C(O)NR⁷R⁸, —OR¹⁰, —NR⁷SO₂OR¹⁰, —N(R⁷)C═(O)R⁹, —NR⁷C(O)—OR⁹, —NR⁷OR⁹, —OCX₃, —OCHX₂, —OCF₃, —OCHF₂, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F R$^x$ is hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl.

R⁷, R⁸, R⁹, and R¹⁰ are independently hydrogen, deuterium, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F; and wherein R¹² is independently H, D, halogen, —CF₃, —CN, —OH, —NH₂, —COOH, —CONH₂, —NO₂, —SH, —SO₂Cl, —SO₃H, —SO₄H, —SO₂NH₂, SO$_n$R¹⁰, —SO$_v$NR⁷R⁸, —NHNH₂, —ONH₂, —NHC═(O)NHNH₂, —NHC═(O)NH₂, —NHSO₂H, —NHC═(O)H, —NHC(O)—OH, —NHOH, —ONR⁷R⁸, —NHC═(O)NHNH₂, —NHC═(O)NR⁷R⁸, —N(O)$_m$, —NR⁷R⁸, —C(O)R⁹, —C(O)OR⁹, C(O)NR⁷R⁸, —NR⁷SO₂OR¹⁰, —N(R⁷)C═(O)R⁹, —NR⁷C(O)—OR⁹, —NR⁷OR⁹, —OCX₃, —OCHX₂, —OCF₃, —OCHF₂, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl. The symbols m and v are independently 1 or 2. The symbol is independently an integer from 0 to 4. The symbol X is independently —Cl, —Br, —I, or —F.

In some embodiments, the disclosure provides a compound of formula:

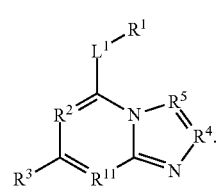

IIIa

L¹ is a bond, substituted or unsubstituted alkylene, substituted or unsubstituted alkenyl, substituted or unsubstituted alkynyl, or substituted or unsubstituted heteroalkylene.

R¹ is hydrogen, deuterium, oxo, halogen, —CX₃, —CN, —SO₂Cl, —SO$_n$R¹⁰, —SO, NR⁷R⁸, —NHNH₂, —ONR⁷R⁸, —NHC═(O)NHNH₂, —NHC═(O)NR⁷R⁸, —N(O)$_m$, —NR⁷R⁸, —C(O)R⁹, —C(O)OR⁹, —C(O)NR⁷R⁸, —OR¹⁰, —NR⁷SO₂R¹⁰, —N(R⁷)C═(O)R⁹, —NR⁷C(O)—OR⁹, —NR⁷OR⁹, —OCX₃, —OCHX₂, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R², R⁴, R⁵, R¹¹ are independently —N, —CH, —CD, or —C-L'-R⁶ where in R⁶ is independently halogen, —CF₃, —CN, —OH, —NH₂, —COOH, —CONH₂, —NO₂, —SH, —SO₂Cl, —SO₃H, —SO₄H, —SO₂NH₂, SO$_n$R¹⁰, —SO$_v$NR⁷R⁸, —NHNH₂, —ONH₂, —NHC═(O)NHNH₂, —NHC═(O)NH₂, —NHSO₂H, —NHC═(O)H, —NHC(O)—OH, —NHOH, —ONR⁷R⁸, —NHC═(O)NHNH₂, —NHC═(O)NR⁷R⁸, —N(O)$_m$, —NR⁷R⁸, —C(O)R⁹, —C(O)OR⁹, —C(O)NR⁷R⁸, —NR⁷SO₂OR¹⁰, —N(R⁷)C═(O)R⁹, —NR⁷C(O)—OR⁹, —NR⁷OR⁹, —OCX₃, —OCHX₂, —OCF₃, —OCHF₂, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F.

R³ is independently H, D, halogen, —CF₃, —CN, —OH, —NH₂, —COOH, —CONH₂, —NO₂, —SH, —SO₂Cl, —SO₃H, —SO₄H?, —SO₂NH₂, —SO$_n$R¹⁰, —SO$_v$NR⁷R⁸, —NHNH₂, —ONH₂, —NHC═(O)NHNH₂, —NHC═(O)NH₂, —NHSO₂H, —NHC═(O)H, —NHC(O)—OH, —NHOH, —ONR⁷R⁸, —NHC═(O)NHNH₂, —NHC═(O)NR⁷R⁸, —N(O)$_m$, —NR⁷R⁸, —C(O)R⁹, —C(O)OR⁹, —C(O)NR⁷R⁸, —NR⁷SO₂R¹⁰, —N(R⁷)C═(O)R⁹, —NR⁷C(O)—OR⁹, —NR⁷OR⁹, —OCX3, —OCHX₂, —OCF₃, —OCHF₂, substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl.

The symbols m and v are independently 1 or 2. The symbol n is independently an integer from 0 to 4. The symbol X is independently —Cl, —Br, —I, or —F $R^x$ is hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl.

$R^7$, $R^8$, $R^9$, and $R^{10}$ are independently hydrogen, deuterium, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F.

In some embodiments, the present disclosure provides a compound having the Formula:

(II)

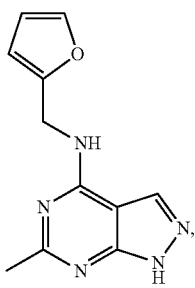

or pharmaceutically acceptable salt thereof.

In some embodiments, the present disclosure provides a compound having the formula (III)

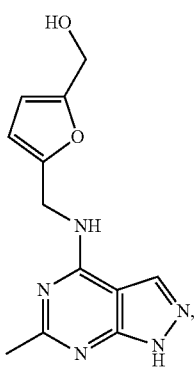

or pharmaceutically acceptable salt thereof.

In some embodiments, the present disclosure provides a compound having the formula (IV)

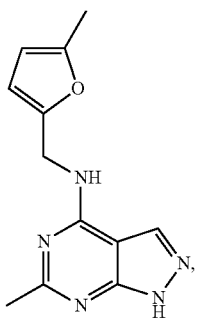

or pharmaceutically acceptable salt thereof.

In some embodiments, the present disclosure provides a compound having the formula:

V

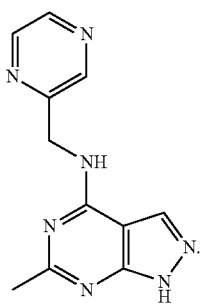

or pharmaceutically acceptable salt thereof.

In some embodiments, the present disclosure provides a compound having the formula:

VI

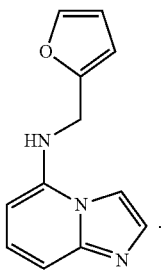

or pharmaceutically acceptable salt thereof.

In some embodiments, the present disclosure provides a compound having the formula:

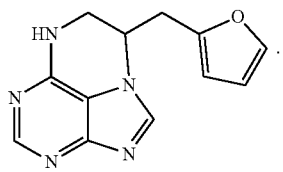

VII or pharmaceutically acceptable salt thereof.

As described herein, the present disclosure also provides compositions, such as but not limited to, pharmaceutical compositions of any compound described herein or a pharmaceutically acceptable salt thereof. In some embodiments, the pharmaceutical compositions comprise a pharmaceutically acceptable carrier and/or excipient.

The compounds described herein can also be combined with other compounds or medicaments. The presently described compounds can be used, for example, to inhibit or ameliorate Parkinson's disease and/or Leigh's disease and/or cardiomyopathy in a subject in need thereof. Accordingly, in some embodiments, the present disclosure provides compositions comprising a compound of Formula I, Ia, and Ib, or its stereoisomers, Formula II, IIa, III, IIIa, IV, V, VI, or VII, and optionally at least one other compound for treatment or prevention of Leigh's disease in a subject in need thereof. the present disclosure provides compositions comprising a compound of Formula T or its stereoisomers, Formula II, IIa, III, IIIa, IV, V, VI, or VII and at least one other compound that treats or prevents a neurodegenerative disease in a subject in need thereof. The present disclosure provides compositions comprising a compound of Formula I, Ia, and Ib or its stereoisomers, Formula II, IIa, III, IIIa, IV, V, VI, or VII, and at least one other compound that treats or prevents a mitochondrial disease in a subject in need thereof. The present disclosure provides compositions comprising a compound of Formula I, Ia, and Ib or its stereoisomers, Formula II, IIa, III, IIIa, IV, V, VI, or VII, and at least one other compound that treats or prevents a cardiomyopathy in a subject in need thereof The compound(s) can be modified by cellular or synthetic processes to become an active compound(s), which can act as a substrate for the enzyme PINK1. In some embodiments, the compound(s) can be modified to include a biphosphate or a triphosphate group. In some embodiments, the active compound(s) are analogs of adenosine triphosphate (ATP). In some embodiments, the active compound(s) are analogs of kinetin triphosphate (KTP). In some embodiments, the active compound(s) can bind to the N-terminal kinase domain of PINK1. In some embodiments, the active compound(s) can bind to the N-terminal kinase domain of PINK1 with a higher catalytic efficiency that its endogenous substrate ATP. In some embodiments, the active compound (s) can bind to the N-terminal kinase domain of mutated or damaged PINK1, including but not limited to cases where mutated of damaged PINK1 does not bind to ATP or does not bind to ATP with endogenous catalytic efficiency. By acting as a precursor to the active compound(s), the compound(s) have increased membrane permeability, as ATP, KTP and their analogs are membrane impermeable. By acting as a substrate, the compound(s), once converted to the active form, can increase the activity of PINK1. In cases where PINK1 is Imitated or damaged and does not exhibit normal levels of activity, the compound(s), once converted to the active form, can restore PINK1 activity.

Accordingly, in some embodiments, the present disclosure provides methods of treating or preventing Parkinson's disease in a subject comprising administering to the subject one or more compounds, or a pharmaceutically acceptable salt thereof, of any one of the compounds described herein or a pharmaceutical composition comprising one or more of the compounds described herein, or pharmaceutically acceptable salt thereof. In some embodiments, the present disclosure provides methods of treating or preventing Leigh's disease in a subject comprising administering to the subject one or more compounds, or a pharmaceutically acceptable salt thereof, of any one of the compounds described herein or a pharmaceutical composition comprising one or more of the compounds described herein, or pharmaceutically acceptable salt thereof. In some embodiments, the treating of Parkinson's or Leigh's disease comprises ameliorating symptoms by stimulating PINK1 or a mutated PINK1.

In some embodiments, the compounds of the disclosure are those embodiments set forth in PCT Application No. PCT/US2014/015863, filed Feb. 11, 2014, which is incorporated by reference in its entirety. In some embodiments, the disclosure provides for a method of treating or preventing a mitochondrial disease or a complex I deficiency in a subject in need thereof by administering a therapeutically effective amount of an embodiment disclosed in PCT Application No. PCT/US2014/015863, filed Feb. 11, 2014, including all provisos therein. In some embodiments, the disclosure provides for a method of treating or preventing Leigh's disease in a subject in need thereof by administering a therapeutically effective amount of an embodiment disclosed in PCT Application No. PCT/US2014/015863, filed Feb. 11, 2014, including all provisos therein. In some embodiments, the disclosure provides for a method of treating or preventing Leigh's disease in a subject in need thereof by administering a therapeutically effective amount of kinetin or a pharmaceutically acceptable salt, tautomer, or isomer thereof.

In some embodiments, a method of treating one or more of the following mitochondrial diseases in a subject is provided: LHON, MELAS, and Charcot Marie Tooth. In some embodiments, the method comprises administering to a subject one or more compounds described herein, or a pharmaceutically acceptable salt thereof, or a pharmaceutical composition comprising one or more compounds described herein, or pharmaceutically acceptable salt thereof. In some embodiments, the method comprises administering to a subject a compound or pharmaceutically acceptable salt thereof that acts as a PINK1 substrate with one or more compounds described herein, or a pharmaceutically acceptable salt thereof, or a pharmaceutical composition comprising one or more compounds described herein, or pharmaceutically acceptable salt thereof. In some embodiments, the cholesterol therapeutic is niacin or acifran. In some embodiments, the subject is a subject in need thereof.

In some embodiments, one or more compounds described herein are administered to a subject. In some embodiments, one or more compounds of Formula I, la, Ib, II, IIa, III, IIIa, IV, V, VI, VII are administered to a subject in need thereof.

In some embodiments, one or more compounds described herein are administered to a subject for treatment or prevention of cardiomyopathy. In some embodiments, one or more compounds of Formula I, Ia, Ib, II, IIa, III, IIIa, IV, V, VI, VII (or their respective pharmaceutical salts thereof) are administered to a subject in need thereof. In some embodiments, one or more pharmaceutical salts optionally in conjunction with a pharmaceutically acceptable carrier are administered to a subject in need thereof.

Although compounds described herein may be shown with specific stereochemistries around certain atoms, such as R, S, cis or trans, the compounds can also be made in the opposite orientation or in a racemic mixture.

In some embodiments, the present disclosure provides pharmaceutical compositions comprising a compound or pharmaceutically salt thereof of any compound described herein.

The compounds described herein can be made by can be made according to the methods described herein and in the examples. The methods described herein can be adapted based upon the compounds desired and described herein. In some embodiments, the method of making the compounds is made according to the schemes described herein. In some embodiments, this method can be used to make one or more compounds as described herein and will be apparent to one of skill in the art which compounds can be made according to the methods described herein.

In some embodiments, a compound is made according to Scheme I.

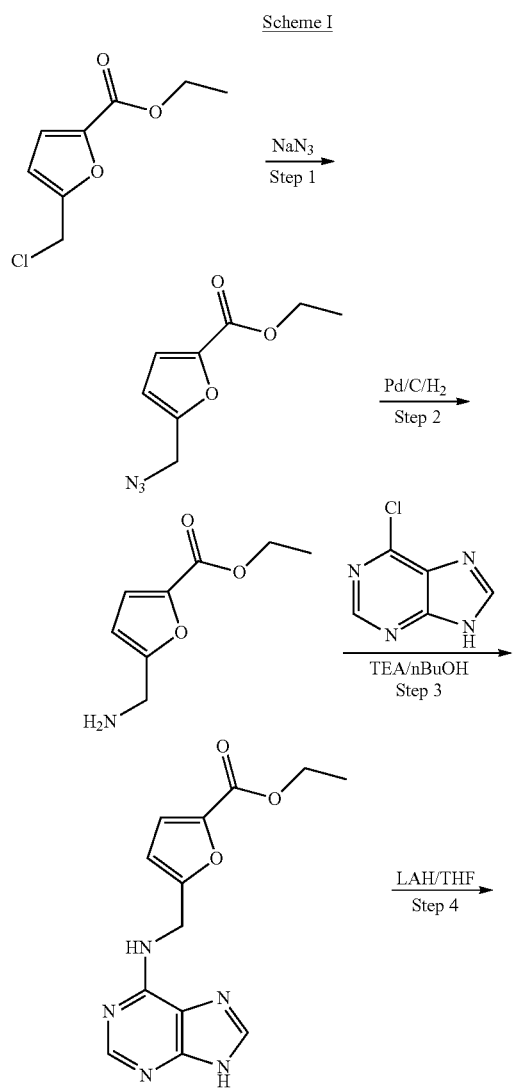

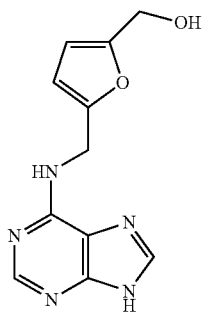

MTK-0026

The conditions and temperatures can be varied, or the synthesis can be performed according to the examples and compounds described herein.

This scheme is a non-limiting synthetic schemes and the synthetic route can be modified as would be apparent to one of skill in the art reading the present specification to produce one or more of the compounds described herein.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginally, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. For example, the compounds can be administered in combination with other therapeutics that inhibit, reduce or ameliorate symptoms of a neurodegentative disease, a mitochondrial disease, and/or cardiomyopathy. The compounds can also be administered in combination with therapeutics intended to treat neurodegentative disease, a mitochondrial disease, and/or cardiomyopathy, including, but not limited to, Levodopa, Sinemet, Requip, Mirapex, Symmetrel Artane, Cogentin, Eldepryl, Azilect, Tasmar, Comtan and Neupro. The compounds can also be combined with one or more dopamine agonists and/or one or more COMT Inhibitors and/or one or more anticholinergics. Examples of other pharmaceuticals or medicaments are known to one of skill in the art and include, but are not limited to those described herein.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers or excipients well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In some embodiments, the compounds can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle or bag containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation or kit, the package or kit containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition of the present disclosure is in the form of a liquid wherein the active agent is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960,150; 3,963,025; 4,186,184; 4,303,637; 5,443,505; and 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of the compounds described herein in accordance with the present disclosure include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compounds are solubilized at least in part by an acceptable solubilizing agent. Certain acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts can be included in the compositions of the disclosure in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

The present disclosure also provides pharmaceutical packs or kits comprising one or more containers filled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein in one or separate containers. In some embodiments, the kit comprises a compound described herein in a single injectable dosage form, such as a single dose within an injectable device such as a syringe with a needle. In some embodiments, the kit comprises a compound described herein in multiple injectable dosage forms in one or a plurality of separate containers.

The present disclosure also provides one or more compounds described above, or a pharmaceutically acceptable salt thereof, or a pharmaceutical composition comprising one or more compounds described above, for use in the manufacture of a medicament for the treatment of flushing and/or of a mammal or subject.

The present disclosure also provides one or more compounds described above, or a pharmaceutically acceptable salt thereof, or a pharmaceutical composition comprising one or more compounds described above, for use in the manufacture of a medicament for the treatment of a neurodegenerative disease in a mammal or subject.

The present disclosure also provides one or more compounds described above, or a pharmaceutically acceptable salt thereof, or a pharmaceutical composition comprising one or more compounds described above, for use in the manufacture of a medicament for the treatment of a mitochondrial disease in a mammal or subject.

The present disclosure also provides one or more compounds described above, or a pharmaceutically acceptable salt thereof, or a pharmaceutical composition comprising one or more compounds described above, for use in the manufacture of a medicament for the treatment of a complex I disease or deficiency in a mammal or subject.

The present disclosure also provides one or more compounds described above, or a pharmaceutically acceptable salt thereof, or a pharmaceutical composition comprising one or more compounds described above, for use in the manufacture of a medicament for the treatment of Leigh's disease in a mammal or subject.

The present disclosure also provides one or more compounds described above, or a pharmaceutically acceptable salt thereof, or a pharmaceutical composition comprising one or more compounds described above, for use in the manufacture of a medicament for the treatment of Parkinson's disease in a mammal or subject.

In some embodiments, the compound or pharmaceutical composition comprising the compounds disclosed herein, or the pharmaceutically acceptable salts herein, are neo-substrates of PINK1. In some embodiments, the neo-substrate is not kinetin. In some embodiments, the neo-substrate is not kinetin riboside. In some embodiments, the neo-substrate is not kinetin riboside 5' monophosphate. In some embodiments, the neo-substrate is not kinetin riboside 5' diphosphate. In some embodiments, the neo-substrate is not kinetin riboside 5' triphosphate. In some embodiments, the neo-substrate is not a derivative (e.g. prodrug) of kinetin, kinetin riboside, kinetin riboside 5' monophosphate, kinetin riboside 5' diphosphate, or kinetin riboside 5' triphosphate. In some embodiments, the neo-substrate is not $N_6$-(delta 2-Isopentenyl)-adenine. In some embodiments, the neo-substrate is not $N_6$-(delta 2-Isopentenyl)-adenosine, $N_6$-(delta 2-Isopentenyl)-adenosine 5' monophosphate, $N_6$-(delta 2-Tsopentenyl)-adenosine 5' diphosphate, $N_6$-(delta 2-Isopentenyl)-adenosine 5' triphosphate, or a derivative (e.g. prodrug) thereof. In some embodiments, the neo-substrate is not a cytokinin. In some embodiments, the neo-substrate is not a cytokinin riboside, cytokinin riboside 5' monophosphate, cytokinin riboside 5' diphosphate, cytokinin riboside 5' triphosphate, or a derivative (e.g. prodrug) thereof [0001] In some embodiments, -L$^1$-R' is not hydrogen.

In embodiments, -L$^1$-R$^1$ is not hydrogen. In embodiments, -L$^1$-R$^1$ is not

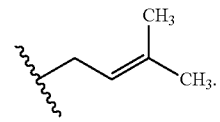 [SMILES: *CC=C(C)C]

In embodiments, -L$^1$-R$^1$ is not

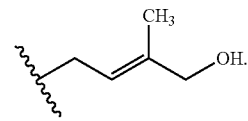 [SMILES: *C/C=C(\C)CO]

In embodiments, -L$^1$-R$^1$ is not

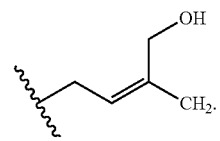

In embodiments, -L$^1$-R$^1$ is not

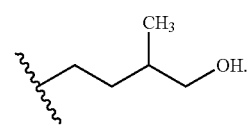 [SMILES: *CCC(C)CO]

In embodiments, -L$^1$-R$^1$ is not

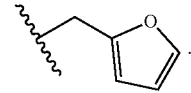

In embodiments, -L$^1$-R$^1$ is not

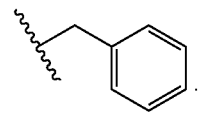 [SMILES: *Cc1ccccc1]

In embodiments, -L¹-R¹ is not

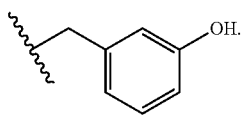 [SMILES: *Cc1cccc(O)c1]

In embodiments, -L¹-R¹ is not

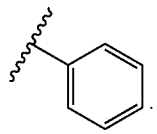

In embodiments, -L¹-R¹ is not

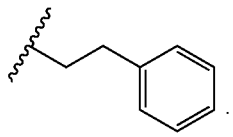

In embodiments, -L¹-R¹ is not

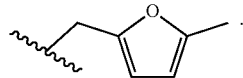 [SMILES: *Cc1ccc(C)o1]

In embodiments, -L¹-R¹ is not

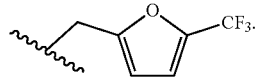 [SMILES: *Cc1ccc(C(F)(F)F)o1]

In embodiments, -L¹-R¹ is not

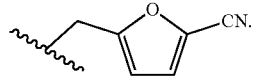 [SMILES: *Cc1ccc(C#N)o1]

In embodiments, -L¹-R¹ is not

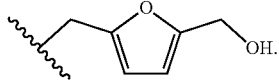 [SMILES: *Cc1ccc(CO)o1]

In embodiments, -L¹-R¹ is not

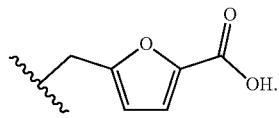 [SMILES: *Cc1ccc(C(=O)O)o1]

In embodiments, -L¹-R¹ is not

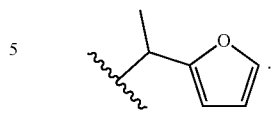

In embodiments, -L¹-R¹ is not

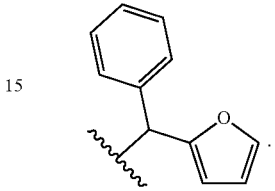

In embodiments, -L¹-R¹ is not

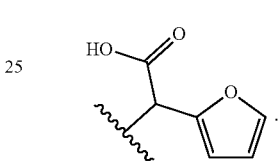

In embodiments, -L¹-R¹ is not

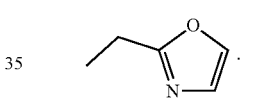

In embodiments, -L¹-R¹ is not

In embodiments, -L¹-R¹ is not

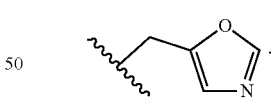

In embodiments, -L¹-R¹ is not

In embodiments, -L¹-R¹ is not

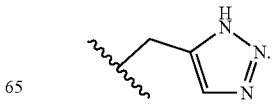

In embodiments, -L¹-R¹ is not

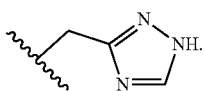

In embodiments, -L¹-R¹ is not

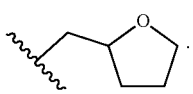

In embodiments, -L¹-R¹ is not

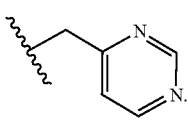

In embodiments, -L¹-R¹ is not

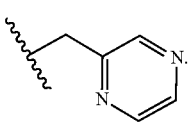 [SMILES: *Cc1cnccn1]

In embodiments, -L¹-R¹ is not

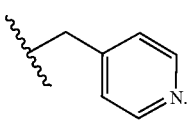

In embodiments, -L¹-R¹ is not

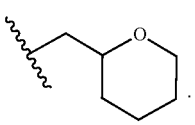

In embodiments, -L¹-R¹ is not

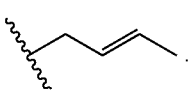 [SMILES: *C/C=C/C]

In embodiments, -L¹-R¹ is not

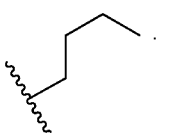 [SMILES: *CCCC]

For each and every method described herein, the mammal or subject can be a mammal or subject in need thereof.

The present disclosure also provides the use of one or more compounds described above, or a pharmaceutically acceptable salt thereof, or a pharmaceutical composition comprising one or more compounds described above, in the modulation of PINK1.

As used herein, "modulation" can refer to either inhibition or enhancement of a specific activity. For example, the modulation of PINK1 activity can refer to the inhibition and/or activation of PINK1 dependent activities, such as a decrease in Parkin recruitment. In some embodiments, the modulation refers to the inhibition or activation of Parkin recruitment. In some embodiments, the compounds described herein activate PINK1 activity by a factor from about 1% to about 50%. The activity of PINK1 can be measured by any method including but not limited to the methods described herein.

The compounds described herein are neo-substrates of PINK1. The ability of the compounds to stimulate or inhibit PINK1 activity may be measured using any assay known in the art used to detect Parkin recruitment or PINK1 phosphorylation, or the absence of such signaling/activity. "PINK1 activity" refers to the ability of PINK1 to phosphorylate any substrate. Such activity can be measured, e.g., in a cell(s), by expressing mutant PINK1, administering the compounds disclosed herein and measuring the degree to which cells expressing the mutant PINK1 were able to phosphorylate an enzymatically active substrate as compared to a cell(s) expressing wild-type PINK1.

PINK1 activity can be measured by changes in the time necessary to recruit 50% of a substrate ("$R^{50}$"). In some embodiments, the compounds reduce a $R^{50}$ by a factor of about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%. In some embodiments, the compounds reduce a $R^{50}$ by a factor from about 1% to about 50%. In some embodiments, the compounds reduce a $R^{50}$ by a factor from about 2% to about 50%. In some embodiments, the compounds reduce a $R^{50}$ by a factor from about 3% to about 50%. In some embodiments, the compounds reduce a $R^{50}$ by a factor from about 4% to about 50%. In some embodiments, the compounds reduce a $R^{50}$ by a factor from about 5% to about 50%. In some embodiments, the compounds reduce a $R^{50}$ by a factor from about 6% to about 50%. In some embodiments, the compounds reduce a $R^{50}$ by a factor from about 7% to about 50%. In some embodiments, the compounds reduce a $R^{50}$ by a factor from about 8% to about 50%. In some embodiments, the compounds reduce a $R^{50}$ by a factor from about 9% to about 50%. In some embodiments, the compounds reduce a $R^{50}$ by a factor from about 10% to about 50%. In some embodiments, the compounds reduce a $R^{50}$ by a factor from about 15% to about 50%. In some embodiments, the compounds reduce a $R^{50}$ by a factor from about 20% to about 50%. In some embodiments, the compounds reduce a $R^{50}$ by a factor from about 25% to about 50%. In some embodiments, the compounds reduce a $R^{50}$ by a factor from about 30% to about 50%. In some embodiments, the compounds reduce a $R^{50}$ by a factor from about 35% to about 50%. In some embodiments, the compounds reduce a $R^{50}$ by a factor from about 40% to about 50%. In some embodiments, the compounds reduce a $R^{50}$ by a factor from about 45% to about 50%. In some embodiments, the compounds reduce a $R^{50}$ by a factor from about 10% to about 40%. In some embodiments, the compounds reduce a $R^{50}$ by a factor from about 10% to about 30%. In some embodiments, the compounds reduce a $R^{50}$ by a factor from about 10% to about 20%.

Plasmids expressing PINK1 can be transfected into an isolated cell and expressed in an isolated cell, expressed in a membrane derived from a cell, expressed in tissue or in an animal. For example, neuronal cells, cells of the immune system, transformed cells, or membranes can be used to test the PINK1 activity described above. Modulation is tested using one of the in vitro or in vivo assays described herein. Other assays generally known can also be used to test the compounds. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to an PINK1. Binding can be performed in solution, in a bilayer membrane, attached to a solid phase, in a lipid monolayer, or in vesicles. For example, in an assay, the binding of the natural ligand to its receptor is measured in the presence of a candidate modulator, such as the compound described herein. Alternatively, the binding of the candidate modulator may be measured in the presence of the natural ligand. Often, competitive assays that measure the ability of a compound to compete with binding of the natural ligand to the receptor are used. Binding can be tested by measuring, e.g., changes in spectroscopic characteristics (e.g., fluorescence, absorbance, refractive index), hydrodynamic (e.g., shape) changes, or changes in chromatographic or solubility properties.

The activity of the compounds can also be measured using assays involving β-arrestin recruitment. β-arrestin serves as a regulatory protein that is distributed throughout the cytoplasm in unactivated cells. Ligand binding to an appropriate GPR109a is associated with redistribution of β-arrestin from the cytoplasm to the cell surface, where it associates with the GPR109a. Thus, receptor activation and the effect of candidate modulators on ligand-induced receptor activation, can be assessed by monitoring β-arrestin recruitment to the cell surface. This is frequently performed by transfecting a labeled P-auestin fusion protein (e.g., β-arrestin-green fluorescent protein (GFP)) into cells and monitoring its distribution using confocal microscopy (see, e.g., Groarke et al., J. Biol. Chem. 274(33):23263 69 (1999)).

Another technology that can be used to evaluate GPR109a-protein interactions in living cells involves bioluminescence resonance energy transfer (BRET). A detailed discussion regarding BRET can be found in Kroeger et al., J. Biol. Chem., 276(16):12736 43 (2001).

Other assays can involve determining the activity of receptors which, when activated by ligand binding, result in a change in the level of intracellular cyclic nucleotides, e.g., cAMP, by activating or inhibiting downstream effectors such as adenylate cyclase. In one embodiment, changes in intracellular cAMP can be measured using immunoassays. The method described in Offermanns & Simon, J. Biol. Chem. 270:15175 15180 (1995) may be used to determine the level of cAMP. Also, the method described in Felley-Bosco et al., Am. J. Resp. Cell and Mol. Biol. 11:159 164 (1994) may be used to determine the level of cGMP. Further, an assay kit for measuring cAMP a is described in U.S. Pat. No. 4,115,538, herein incorporated by reference.

In another embodiment, transcription levels can be measured to assess the effects of a test compound on ligand-induced signal transduction. A host cell containing the protein of interest is contacted with a test compound in the presence of the natural ligand for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, Nature Biotechnology 15:961 964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Additional assays can also be used. For example, the activity of the compound can be measured in a cell based assay. For example, a nucleic acid molecule encoding GPR109a, such as Accession NP 808219.1, can be incorporated into an expression vector and transfected or transformed into a cell. In some embodiments, the expression vector is a plasmid or virus. In some embodiments, the expression of the nucleic acid molecule is operably linked to a promoter. The promoter can be constitutive or respond to a drug or other response element so that the expression can be controlled. The type of expression vector is not critical and any expression vector can be used that is suitable for the cell type. In some embodiments, the plasmid is pCMV-Prolink. In some embodiments, the cell is a mammalian cell. In some embodiments, the cell is a Chinese Hamster Ovary (CHO-1) cell. In some embodiments, the cell is an EA-arrestin parental line CHO-1 cell, which is available from DiscoveRx Corporation (Fremont, Calif.). The expression of the receptor can be stable so that that stable cell lines can be selected. The selection of stably expressing receptor cell lines can be done to routine methods, such as selecting for expression under G418 (Geneticin). The expression of the receptor can also be transient.

After the receptor is expressed in a cell the cells can be grown in appropriate media in the appropriate cell plate. The cells can be plated, for example at 5000-10000 cells per well in a 384 well plate. In some embodiments, the cells are plated at about 1000, 2000, 3000, 4000, 5000, 6000, 7000, 8000, 9000, or 10000 cells/per well. The plates can have any number of wells and the number of cells can be modified accordingly.

In some embodiments, to measure cAMP activity that is mediated by the receptor, responses can be determined by measuring changes in intracellular cAMP using. cAMP can be measured by any known method or kit. Examples of a kit that can be used, include but are not limited to, CisBio HTRF cAMP HiRange kit (cat #62AM6PEJ) based on time-resolved fluorescence resonance energy transfer (TR-FRET). The compounds (e.g. test or control) can be contacted with the cells for a period of time and then cAMP can be measured.

In some embodiments, a compound's effect on the modulation of PINK1 will be measured using cells expressing mutant and wild-type versions of PINK1. PINK1 is generally known. In some embodiments, the enzymatic rescue is measured. Enzymatic rescue experiments are experiments in which cells expressing mutated forms of the PINK1 with reduced or deficient enzymatic activity are contacted with compounds of the present disclosure and are able to re-activate the mutated PINK1 enzymatic activity. PINK1 molecules are known. In some embodiments, the compounds of the present disclosure are able to enzymatically rescue human PINK1 (accession number AY358957, which is incorporated by reference in its entirety) having the following amino acid sequence:

(SEQ ID NO: 1)
MLWWLVLLLLPTLKSVFCSLVTSLYLPNTEDLSLWLWPKPDLHSGTRTEV
STHTVPSKPGTASPCWPLAGAVPSPTVSRLEALTRAVQVAEPLGSCGFQG
GPCPGRRRD.

In some embodiment, the compounds of the present disclosure are able to enzymatically rescue mouse PINK1 (accession number XM 924521, which is incorporated by reference in its entirety) having the following amino acid sequence:

(SEQ ID NO: 2)
MAVRQALGRGLQLGRALLLRFAPKPGPLFGWGKPGPAAAWGRGE

RPGQVVSPGAQPRPVGLPLPDRYRFFRQSVAGLAARIQRQFMVRARGGAG

PCGRAVFLAFGLGLGLIEEKQAEGRRAASACQEIQAIFTQKTKRVSDPLD

TRCWQGFRLEDYLIGQAIGKGCNAAVYEATMPTLPQHLEKAKHLGLIGKG

PDVVLKGADGEQAPGTPTFPFAIKMMWNISAGSSSEAILSKMSQELVPAS

RVALAGEYGAVTYRRSRDGPKQLAPHPNIIRVFRAFTSSVPLLPGALADY

PDMLPPHYYPEGLGHGRTLFLVMKNYPCTLRQYLEEQTPSSRLATMMTLQ

LLEGVDHLVQQGIAHRDLKSDNILVEWDSDGCPWLVISDFGCCLADQHVG

LRLPFNSSSVERGGNGSLMAPEVSTAHSGPSAVIDYSKADTWAVGAIAYE

IFGLANPFYGQGSAHLESRSYQEAQLPEMPESVPPEARRLVRSLLQREAS

KRPSARLAANVLHLSLWGEHLLALKNLKLDKMIAWLLQQSAATLLADRLR

EKSCVETKLQMLFLANLECEALCQAALLLSSWRAAP.

In some embodiment, the compounds of the present disclosure are able to enzymatically rescue rat PINK1 (accession number XM 216565, which is incorporated by reference in its entirety) having the following amino acid sequence:

(SEQ ID NO: 3)
MAVRQALGRGLQLGRALLLRFAPKPGPVSGWGKPGPGAAWGRGE

RPGRVSSPGAQPRPLGLPLPDRYRFFRQSVAGLAARIQRQFVVRARGGAG

PCGRAVFLAFGLGLGLIEEKQAESRRAASACQEIQAIFTQKNKQVSDPLD

TRRWQGFRLEDYLIGQAIGKGCNAAVYEATMPTLPQHLEKAKHLGLLGKG

PDVVSKGADGEQAPGAPAFPFAIKMMWNISAGSSSEAILSKMSQELEALG

SANRKGTLQQFRR

The present disclosure also provides the use of one or more compounds described above, or a pharmaceutically acceptable salt thereof, or a pharmaceutical composition comprising one or more compounds described above, in the treatment of Leigh's disease, Parkinson's disease, and/or any other mitochondrial disease or neurodegenerative disease. In some embodiments, the mammal is a mammal in need thereof.

Any medicament having utility in an application described herein can be used in co-therapy, co-administration or co-formulation with a composition as described above. Such additional medicaments include, medicines for cholesterol, such as but not limited to niacin, acifran, a statin, such as, but not limited to, lovastatin, atorvastatin, fluvastatin, pitavastatin, rosuvastatin, simvastatin, and the like. Other additional medicaments include, but are not limited to, ezetimibe, Trilipix (fenofibric acid), and the like. Other medicaments and compositions include, but are not limited to, fish oil, red yeast rice, omega fatty acids, and the like.

The additional medicament can be administered in co-therapy (including co-formulation) with the one or more of the compounds described herein.

In some embodiments, the response of the disease or disorder to the treatment is monitored and the treatment regimen is adjusted if necessary in light of such monitoring.

Frequency of administration is typically such that the dosing interval, for example, the period of time between one dose and the next, during waking hours is from about 2 to about 12 hours, from about 3 to about 8 hours, or from about 4 to about 6 hours. It will be understood by those of skill in the art that an appropriate dosing interval is dependent to some degree on the length of time for which the selected composition is capable of maintaining a concentration of the compound(s) in the subject and/or in the target tissue (e.g., above the $EC_{50}$ (the minimum concentration of the compound which modulates the receptor's activity by 90%). Ideally the concentration remains above the EC50 for at least 100% of the dosing interval. Where this is not achievable it is desired that the concentration should remain above the EC50 for at least about 60% of the dosing interval, or should remain above the EC50 for at least about 40% of the dosing interval.

Compounds provide for in this disclosure are set forth in Table A. Each compound and its pharmaceutically acceptable salt, tautomer, and isomer is contemplated by any of the compoisitons or methods provided herein:

In order that the disclosure disclosed herein may be more efficiently understood, examples are provided below. It should be understood that these examples are for illustrative purposes only and are not to be construed as limiting the disclosure in any manner. Throughout these examples, there may be molecular cloning reactions, and other standard recombinant DNA techniques described and these were carried out according to methods described in Maniatis et al., Molecular Cloning—A Laboratory Manual, 2nd ed., Cold Spring Harbor Press (1989), using commercially available reagents, except where otherwise noted.

A. U.S. Patent Application No. 61/763,444, filed Feb. 11, 2013

B. U.S. Patent Application No. 61/845,529, filed Jul. 12, 2103,

C. Any non-provisional application, filed Feb. 11, 2014, claiming priority to the above-identified U.S. Provisional Patent applications.

D. Kruse S E, et al. (2008) Mice with mitochondrial complex I deficiency develop a fatal encephalomyopathy. *Cell Metab* 7:312-320

E. Hertz N T, Berthet A, Sos M L, Thorn K S, Burlingame A L, Nakamura K, Shokat K M. A Neo-Substrate that Amplifies Catalytic Activity of Parkinson's-Disease-Related Kinase PINK1. *Cell* 154, 737-747, Aug. 15, 2013.

F. Quintana, et al. *PNAS*, Jun. 15, 2010; vol. 107 no. 24

1. Schapira, A. H. Mitochondrial disease. Lancet 379, 1825-1834, (2012).
2. Chen, Y. and Dorn, C. PINK1-Phosphorylated Mitofusin-2 Is a Parkin Receptor for Culling Damaged Mitochondria. Science 340, 471-475, (2013).
3. Narendra, D. P. et al. PINK1 is selectively stabilized on impaired mitochondria to activate Parkin. PLoS Biol 8, e1000298 (2010).
4. Wang, X., (2011). et al. PINK1 and Parkin target Miro for phosphorylation and degradation to arrest mitochondrial motility. Cell 147, 893-906, (2011).
5. Richardson P, et al. Report of the 1995 World Health Organization/International Society and Federation of Cardiology Task Force on the Definition and Classification of cardiomyopathies. Circulation 1996; 93:841.
6. Longo, D, et al. Harrison's Internal Medicine. 18$^{th}$ ed. (online), Ch. 238 (2011).
7. Petit, A. et al. Wild-type PINK1 prevents basal and induced neuronal apoptosis, a protective effect abrogated by Parkinson disease-related mutations. J Biol Chem 280, 3402534032 (2005).
8. Koh, H. & Chung, J. PINK1 as a molecular checkpoint in the maintenance of mitochondria) function and integrity. Mol Cells 34, 7-13, (2012).
9. Martins-Branco, D. et al. Ubiquitin proteasome system in Parkinson's disease: a keeper or a witness? Exp Neurol 238, 89-99, (2012).
10. Geisler, S. et al. The PINK1/Parkin-mediated mitophagy is compromised by PD-associated mutations. Autophagy 6, 871-878, (2010).
11. Shin, J. H. et al. PARIS (ZNF746) repression of PGC-1alpha contributes to neurodegeneration in Parkinson's disease. Cell 144, 689-702, (2011).
12. Henchcliffe, C. & Beal, M. F. Mitochondria) biology and oxidative stress in Parkinson disease pathogenesis. Nat Clin Pract Neurol 4, 600-609 (2008).
13. Pridgeon, J. W., Olzmann, J. A., Chin, L. S. & Li, L. PINK1 Protects against Oxidative Stress by Phosphorylating Mitochondria) Chaperone TRAP1. PLoS Bio15, e172 (2007).
14. Hague, M. E. et al. Cytoplasmic Pinkl activity protects neurons from dopaminergic neurotoxin MPTP. Proc Natl Acad Sci USA 105, 1716-1721 (2008).
15. Gautier, C. A., Kitada, T. & Shen, J. Loss of PINK1 causes mitochondria) functional defects and increased sensitivity to oxidative stress. Proc Natl Acad Sci USA 105, 1136411369 (2008).
16. Samaranch, L. et al. PINK1-linked parkinsonism is associated with Lewy body pathology. Brain 133, 1128-1142, (2010).
17. Merrick, K. A. et al. Switching Cdk2 on or off with small molecules to reveal requirements in human cell proliferation. Mol Cell 42, 624-636, (2011).
18. Mills, R. D. et al. Biochemical aspects of the neuroprotective mechanism of PTEN-induced kinase-1 (PINK1). J Neurochem 105, 18-33 (2008).
19. Hertz, N. T. et al. Chemical Genetic Approach for Kinase-Substrate Mapping by Covalent Capture of Thiophosphopeptides and Analysis by Mass Spectrometry. Current Protocols in Chemical Biology 2, 15-36, (2010).
20. Blethrow, J. D., Glavy, J. S., Morgan, D. 0. & Shokat, K. M. Covalent capture of kinase-specific phosphopeptides reveals Cdk1-cyclin B substrates. Proc Natl Acad Sci USA 105, 1442-1447 (2008).
21. Kondapalli, C. et al. PINK1 is activated by mitochondrial membrane potential depolarization and stimulates Parkin E3 ligase activity by phosphorylating Serine 65. Open Biol 2, 120080, (2012).
22. Beilina, A. et al. Mutations in PTEN-induced putative kinase 1 associated with recessive parkinsonism have differential effects on protein stability. Proc Natl Acad Sci USA 102, 5703-5708 (2005).
23. Hertz, N. T. & Shokat, K. M.
24. Ishii, Y., Sakai, S. & Honma, Y. Cytokinin-induced differentiation of human myeloid leukemia HL-60 cells is associated with the formation of nucleotides, but not with incorporation into DNA or RNA. Biochim Biophys Acta 1643, 11-24 (2003).
25. Kulkarni, R. N. et al. Tissue-specific knockout of the insulin receptor in pancreatic beta cells creates an insulin secretory defect similar to that in type 2 diabetes. Cell 96, 329-339, (1999).
26. Kissil, J. L. et al. DAP-kinase loss of expression in various carcinoma and B-cell lymphoma cell lines: possible implications for role as tumor suppressor gene. Oncogene 15, 403-407, (1997).
27. Gao, Y., Ge, G. & Ji, H. LKB1 in lung cancerigenesis: a serine/threonine kinase as tumor suppressor. Protein Cell 2, 99-107, (2011).
28. I. Martin, V. L. Dawson, T. M. Dawson, Recent advances in the genetics of Parkinson's disease. Annu Rev Genomics Hum Genet 12, 301 (Sep. 22, 2011).
29. A. M. Edwards et al., Too many roads not taken. Nature 470, 163 (Feb. 10, 2011).
30. J. D. Sadowsky et al., Turning a protein kinase on or off from a single allosteric site via disulfide trapping. Proc Natl Acad Sci USA 108, 6056 (Apr. 12, 2011).
31. 0. Goransson et al., Mechanism of action of A-769662, a valuable tool for activation of AMP-activated protein kinase. J Biol Chem 282, 32549 (Nov. 9, 2007).
32. S. Lourido et al., Calcium-dependent protein kinase 1 is an essential regulator of exocytosis in Toxoplasma. Nature 465, 359 (May 20, 2010).

The following examples are provided to describe the disclosure in greater detail. They are intended to illustrate, not to limit, the disclosure. Various publications, including patents, published applications, technical articles and scholarly articles are cited throughout the specification. Each of these cited publications is incorporated by reference herein in its entirety.

EXAMPLES

Example 1: Synthesis of Compounds

| | |
|---|---|
| A General procedure 1 | 103 |
| B General procedure 2 | 109 |

| | |
|---|---|
| C General procedure 3 | 112 |
| D General procedure 4 | 114 |
| E General procedure 5 | 115 |
| F General procedure 6 | 116 |
| G General procedure 7 | 116 |
| H General procedure 8 | 117 |
| I General procedure 9 | 118 |
| J General procedure 9 | 119 |
| K General procedure 10 | 122 |
| L General procedure 11 | 123 |
| M General procedure 12 | 127 |
| N General procedure 13 | 128 |
| O General procedure 19 | 136 |
| P General procedure 20 | 137 |
| Q General procedure 21 | 138 |
| R General procedure 22 | 138 |
| S General procedure 23 | 138 |
| Primary cultures of medium spiny neurons | 142 |
| MPP+ exposure and drug treatment | 143 |
| End point evaluation: measure of total number of TH positive neurons | 143 |
| Statistics | 144 |
| RESULTS | 144 |
| A. Effect of Kinetin pre-incubated during 2 days on dopaminergic neurons after a MPP+ injury | 144 |
| B. Effect of Kinetin pre-incubated during 6 days on dopaminergic neurons after a MPP+ injury | 145 |
| C. Effect of Kinetin pre-incubated during 10 days on dopaminergic neurons after a MPP+ injury | 145 |
| MPP+ exposure and drug treatment | 152 |

Abbreviations List

General
anhy. Anhydrous 20
aq. Aqueous
ruin minute(s)
mL Milliliter
mmol millimole(s)
mol mole(s)
MS mass spectrometry
NMR nuclear magnetic resonance
TLC thin layer chromatography
HPLC high-performance liquid chromatography
  Spectrum
Hz Hertz
δ chemical shift
J coupling constant
s Singlet
d Doublet
t Triplet
q Quartet
m Multiplet
br Broad
qd quartet of doublets
dquin doublet of quintets
dd doublet of doublets
dt doublet of triplets
  Solvents and Reagents
$CHCl_3$ Chloroform
DCM Dichloromethane
DMF Dimethylformamide
Et2O diethyl ether
EtOH ethyl alcohol
EtOAc ethyl acetate
MeOH methyl alcohol
MeCN Acetonitrile
PE petroleum ether
THE Tetrahydrofuran
AcOH acetic acid
HCl hydrochloric acid
$H_2SO_4$ sulfuric acid
$NH_4Cl$ ammonium chloride
KOH potassium hydroxide
NaOH sodium hydroxide
$K_2CO_3$ potassium carbonate
$Na_2CO_3$ sodium carbonate
TFA trifluoroacetic acid
$Na_2SO_4$ sodium sulfate
$NaBH_4$ sodium borohydride
$NaHCO_3$ sodium bicarbonate
LiHMDS lithium hexamethyldisilylamide
NaHMDS sodium hexamethyldisilylamide
LAH lithium aluminum hydride
$NaBH_4$ sodium borohydride
LDA lithium diisopropylarnide
$Et_3N$ Triethylamine
DMAP 4-(dimethylamino)pyridine
DIPEA N,N-diisopropylethylamine
$NH_4OH$ ammonium hydroxide
EDCI 1-ethyl-3-(3-dimethylaminopropyl)carbodiimide
HOBt 1-hydroxybenzotriazole
HATU O-(7-azabenzotriazol-1-yl)-N,N,N',N'-tetra-methyl-uronium
Xphos 2-Dicyclohexylphosphino-2',4',6'-triisopropylbiphenyl
BINAP 2, 2'-bis(diphenylphosphanyl)-1,1'-binaphthyl General Experimental Notes:

In the following examples, the reagents (chemicals) were purchased from commercial sources (such as Alfa, Acros, Sigma Aldrich, TCI and Shanghai Chemical Reagent Company), and used without further purification. Flash chromatography was performed on an Ez Purifier III using column with silica gel particles of 200-300 mesh. Analytical and preparative thin layer chromatography (TLC) plates were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA). HPLC chromatographs were record on an Agilent 1200 Liquid Chromatography (Agilent, USA, column: Ultimate 4.6 mm×50 mm, 5 μm, mobile phase A: 0.1% formic acid in water; mobile phase B: acetonitrile). Microwave reactions were run on an Initiator 2.5 Microwave Synthesizer (Biotage, Sweden).

General Experimental Notes:

In the following examples, the reagents (chemicals) were purchased from commercial sources (such as Alfa, Acros, Sigma Aldrich, TCI and Shanghai Chemical Reagent Company), and used without further purification. Flash chromatography was performed on an Ez Purifier III using column with silica gel particles of 200-300 mesh. Analytical and preparative thin layer chromatography (TLC) plates were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, 6) downfield from tetramethylsilane. Mass spectra were given with electrospray ionization (ESI) from a Waters LCT TOF Mass Spectrometer (Waters, USA). HPLC chromatographs were record on an Agilent 1200 Liquid Chromatography (Agilent, USA, column. Ultimate 4.6 mm×50 mm, 5 m, mobile phase A: 0.1% formic acid in water; mobile phase B: acetonitrile). Microwave reactions were run on an Initiator 2.5 Microwave Synthesizer (Biotage, Sweden).

A. General Procedure 1:

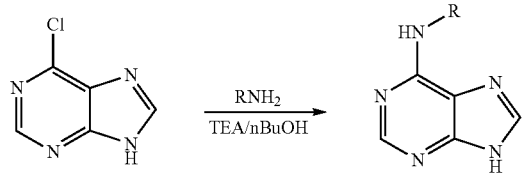

To a solution of 6-chloropurine (1 eq.) in n-butanol were added TEA (2.0 eq) and the corresponding amine (1.2 eq). The mixture was sealed and stirred at 100° C. for 12 h. The mixture was filtered, and the precipitation was washed with EA and water twice, and dried under vacuum to provide the desired product. Further purification was done by a reversed phase chromatography, using 0-100% methanol and water as the eluting solvent.

MTK-0013/NB612-059 [N-(oxazol-2-ylmethyl)-9H-purin-6-amine]

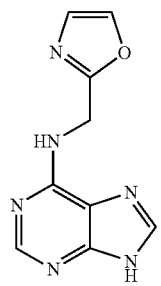

$^1$H NMR (400 MHz, DMSO-$d_6$) δ: 12.96 (br, 1H), 8.18 (s, 1H), 8.15 (br, 1H), 8.00 (s, 1H), 7.12 (s 1H), 4.80 (br, 2H). LC-MS: m/z 217.2 [M+H]$^+$.

MTK-0018/NB612-046 [N-(thiazol-2-ylmethyl)-9H-purin-6-amine]

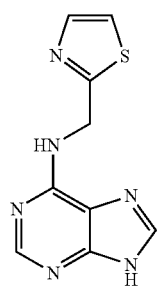

$^1$H NMR (400 MHz, DMSO-$d_6$) δ: 12.93 (br, 1H), 8.48 (s, 1H), 8.22 (s, 1H), 8.17 (s, 1H), 7.73 (d, J=3.6 Hz, 1H), 7.56 (d, J=3.2 Hz, 1H), 4.97 (br, 2H). LC-MS: m/z 233.3 [M+H]$^+$.

MTK-0021/NB579-037 [N-(2-methylallyl)-9H-purin-6-amine]

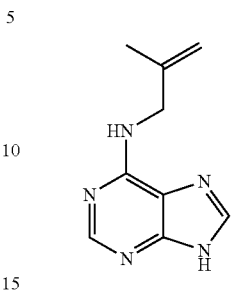

$^1$H NMR (400 MHz, DMSO-$d_6$) δ: 1.73 (s, 3H) 3.93-4.18 (m, 2H) 4.77 (d, J=17.73 Hz, 2H) 7.71-7.91 (m, 1H), 8.09 (s, 1H), 8.16 (br. s., 1H), 12.92 (br. s., 1H). LCMS (m/z) 190.06 [M+H]$^+$.

MTK-0025/NB612-036 [N-(oxazol-4-ylmethyl)-9H-purin-6-amine]

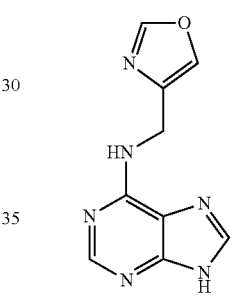

$^1$H NMR (400 MHz, DMSO-$d_6$) δ: 12.85 (br, 1H), 8.30 (s, 1H), 8.20 (s, 1H), 8.17 (s, 1H), 7.94 (br, 1H), 7.90 (s, 1H), 4.61 (br, 2H). LC-MS: m/z 217.2 [M+H]$^+$.

MTK-0028/NB579-056 [N-(2-(furan-2-yl)ethyl)-9H-purin-6-amine]

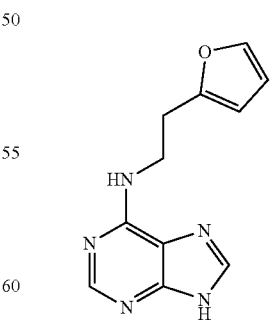

$^1$H NMR (400 MHz, DMSO-$d_6$) δ: 2.96 (t, J=7.39 Hz, 2H) 3.74 (br. s., 2H) 6.19 (d, J=2.69 Hz, 1H) 6.32-6.40 (m, 1H) 7.51-7.58 (m, 1H) 7.75 (br. s., 1H) 8.09 (s, 1H) 8.20 (br. s., 1H) 12.92 (br. s., 1H). LCMS (m/z) 229.68 [M+H]$^+$.

MTK-0030/NB571-057 [N-(pyridin-4-ylmethyl)-
9H-purin-6-amine]

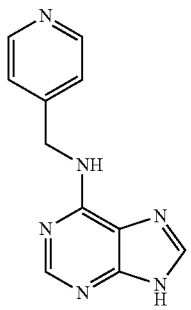 [SMILES: c1cc(CNc2ncnc3[nH]cnc23)ccn1]

¹H NMR (400 MHz, DMSO-d₆) δ: 12.99 (br, 1H), 8.47 (d, 2H), 8.3 (d, 2H), 8.16 (s, 1H), 7.31 (d, 2H), 4.72 (br, 2H). LCMS (m/z) 227.53 [M+H]⁺.

MTK-0034/NB579-038 [N-((tetrahydro-2H-pyran-2-yl)methyl)-9H-purin-6-amine]

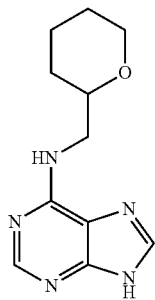 [SMILES: c1nc(NCC2CCCCO2)c2nc[nH]c2n1]

¹H NMR (400 MHz, DMSO-d₆) δ: 1.17-1.27 (m, 1H), 1.45 (br. s., 3H), 1.63 (d, J=12.63 Hz, 1H), 1.71-1.83 (m, 1H), 3.33 (m, 1H), 3.50 (br. s., 2H), 3.87 (d, J=11.28 Hz, 1H), 7.40 (br. s., 1H), 8.09 (s, 1H), 8.18 (br. s., 1H), 12.91 (br. s., 1H). LC-MS (m/z) 234.56 [M+H]⁺.

MTK-0035/NB612-028 [N-((1H-pyrazol-5-yl)methyl)-9H-purin-6-amine]

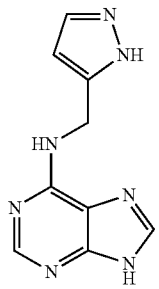 [SMILES: c1cc(CNc2ncnc3[nH]cnc23)[nH]n1]

¹H NMR (400 MHz, DMSO-d₆) δ: 12.91 (br, 1H), 12.58 (br, 1H), 8.21 (s, 1H), 8.15 (s, 1H), 7.84 (br, 1H), 7.81 (br, 1H), 6.15 (br, 1H), 4.70 (br, 2H). LC-MS: m/z 216.2 [M+H]⁺.

MTK-0036/NB579-031 [N-(pyridin-3-ylmethyl)-9H-purin-6-amine]

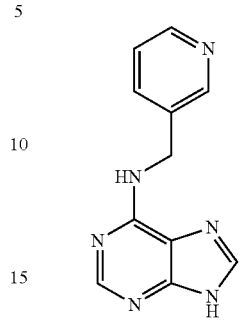

¹HNMR (Methanol-d₄) δ: 4.73 (br. s., 2H), 7.33 (dd, J=7.66, 4.70 Hz, 1H), 7.76 (d, J=8.06 Hz, 1H), 8.13 (s, 1H), 8.20 (s, 1H), 8.26 (br. s., 1H), 8.43 (dd, J=4.70, 1.48 Hz, 1H), 8.59 (d, J=1.61 Hz, 1H), 12.97 (br. s., 1H). LCMS (m/z) 227.53 [M+H]⁺.

MTK-0037/NB612-026 [N-((tetrahydrofuran-3-yl)methyl)-9H-purin-6-amine]

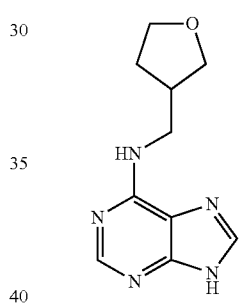

¹H NMR (400 MHz, DMSO-d₆) δ: 12.90 (br, 1H), 8.08 (br, 1H), 7.81 (s, 1H), 7.80 (br, 1H), 3.77-3.47 (m, 6H), 2.64-2.60 (m, 1H), 1.95-1.91 (m, 1H), 1.68-1.64 (m, 1H). LC-MS: m/z 220.2 [M+H]⁺.

MTK-0038/NB612-025 [N-(furan-2-ylmethyl)-N-methyl-9H-purin-6-amine]

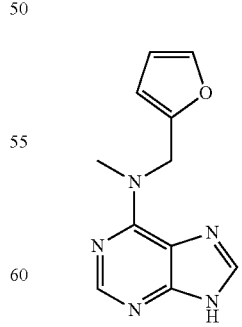

¹H NMR (400 MHz, DMSO-d₆) δ: 13.06 (br, 1H), 8.24 (s, 1H), 8.15 (s, 1H), 7.57 (dd, J=2.4 Hz, 1.2 Hz, 1H), 6.40-6.38 (m, 1H), 6.32 (d, J=3.2 Hz, 1H), 5.38 (br, 2H), 3.34 (s, 3H). LC-MS: m/z 230.2 [M+H]⁺.

85

MTK-0039/NB612-015 [N-butyl-9H-purin-6-amine]

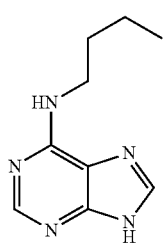

¹H NMR (400 MHz, DMSO-d₆) δ: 12.85 (br, 1H), 8.16 (br, 1H), 8.05 (s, 1H), 7.60 (br, 1H), 3.46 (br, 2H), 1.60-1.53 (m, 2H), 1.38-1.28 (m, 2H), 0.89 (t, J=7.6 Hz, 3H). LC-MS: m/z 192.2 [M+H]⁺.

MTK-0040/NB612-014 [N-(prop-2-ynyl)-9H-purin-6-amine]

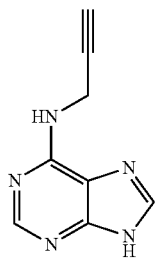

¹H NMR (400 MHz, DMSO-d₆) δ: 12.99 (br, 1H), 8.24 (br, 1H), 8.13 (s, 1H), 8.00 (br, 1H), 4.26 (br, 2H), 3.02 (s, 1H). LC-MS: m/z 174.2 [M+H]⁺.

MTK-0041/NB612-011 [N-((tetrahydrofuran-2-yl)methyl)-9H-purin-6-amine]

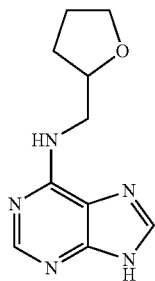 [SMILES: c1nc(NCC2CCCO2)c2nc[nH]c2n1]

¹H NMR (400 MHz, CDCl₃) δ: 8.43 (s, 1H), 7.99 (s, 1H), 6.59 (br, 1H), 4.21-4.16 (m, 1H), 3.97-3.91 (m, 2H), 3.82-3.71 (m, 2H), 2.08-2.02 (m, 1H), 1.98-1.89 (m, 2H), 1.73-1.69 (m, 1H). LC-MS: m/z 220.2 [M+H]⁺.

86

MTK-0042/NB612-012 [N-isopentyl-9H-purin-6-amine]

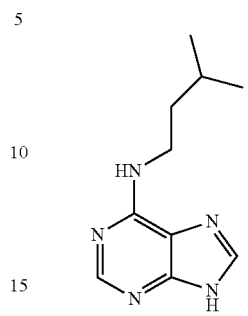

¹H NMR (400 MHz, DMSO-d₆) δ: 12.86 (br, 1H), 8.17 (br, 1H), 8.07 (s, 1H), 7.57 (br, 1H), 3.49 (br, 2H), 1.67-1.61 (m, 1H), 1.52-1.47 (m, 2H), 0.91 (d, J=6.4 Hz, 6H). LC-MS: m/z 206.2 [M+H]⁺.

MTK-0043/NB612-013 [N-((5-methylfuran-2-yl)methyl)-9H-purin-6-amine]

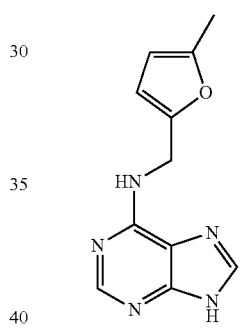

¹H NMR (400 MHz, DMSO-d₆) δ: 12.94 (br, 1H), 8.20 (br, 1H), 8.11 (s, 1H), 7.99 (br, 1H), 6.09 (s, 1H), 5.95 (s, 1H), 4.64 (br, 2H), 2.21 (s, 3H). LC-MS: m/z 230.1 [M+H]⁺.

MTK-0044/NB582-032 [N-(pyrazin-2-ylmethyl)-9H-purin-6-amine]

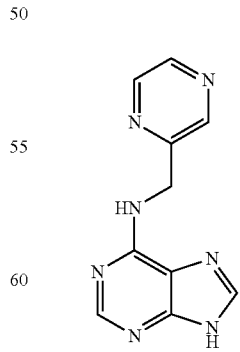

¹H NMR (Methanol-d₄) δ: 8.70 (d, J=1.1 Hz, 1H), 8.64-8.57 (m, 1H), 8.51 (d, J=2.6 Hz, 1H), 8.26 (s, 1H), 8.13 (s, 1H), 5.02 (s, 2H). LC-MS: m/z 228.2 [M+H]⁺.

MTK-0050/NB582-063 [N,N-diethyl-9H-purin-6-amine]

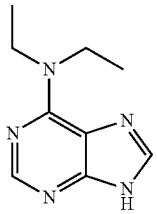

¹H NMR (Chloroform-d) δ: 8.40 (s, 1H), 7.98 (s, 1H), 4.42-3.72 (m, 4H), 1.35 (t, J=7.0 Hz, 6H). LCMS (m/z) 192.2 [M+H]⁺.

MTK-0060/NB582-078 [N₄₁H-1, 2, 4-triazol-3-yl) methyl)-9H-purin-6-amine]

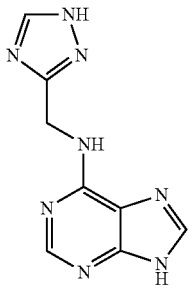

¹H NMR (Deuterium water) δ: 8.62 (s, 1H), 8.54 (s, 1H), 8.35 (s, 1H), 5.74 (s, 2H), 3.63 (s, 1H). LCMS (m/z) 217.2 [M+H]⁺.

B. General Procedure 2:

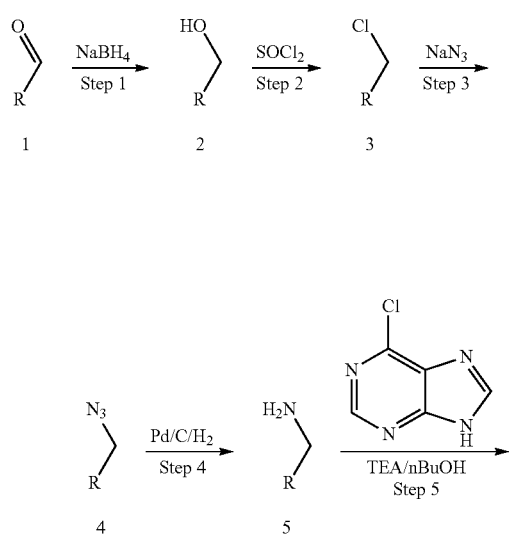

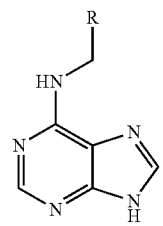

Step 1: to a mixture of the corresponding aldehyde (1, 1 mmol) in MeOH, was added NaBH₄ (2 mmol). The mixture was stirred at room temperature until LCMS indicated completion of the reaction. The mixture was then concentrated in vacuo, the residue was partitioned between brine and DCM. The organic layer was separated, dried over anhydrous Na₂SO₄, then filtered, and the filtrate was concentrated in vacuo to afford the crude compound 2, which was purified by a flash chromatography.

Step 2: a mixture of the corresponding compound 2 (1 mmol) in SOCl₂ (5 mL) was heated to 80° C. until TLC show completion of the reaction. The mixture was concentrated in vacuo to afford the crude product 3, which was used directly for the next step without purification.

Step 3: to a mixture of the corresponding chloride (3, 1 mmol) in DMF (5 mL) was added NaN₃ (346 mg, 5.32 mmol). The mixture was heated to 50° C. overnight. TLC show consumption of the start material, one new spot appeared. The mixture was then diluted with brine (20 mL), extracted with DCM (10 mL, twice). The organic layer was combined, dried over anhydrous Na₂SO₄, filtered and the filtrate was concentrated in vacuo to afford the crude compound 4, which was purified by a flash chromatography.

Step 4: to a mixture of the corresponding azide 4 (1 mmol) in ethanol was added 10% palladium on carbon (50 mg), the mixture was held stirring under H₂ atmosphere overnight. TLC show consumption of the start material, one new spot appeared. The mixture was filtered through a celite pad; the filtrate was concentrated to afford the crude compound 5, which was used directly for the next step without purification.

Step 5: the same procedure as General procedure 1

MTK-0047/NB616-032 b[N-((1H-imidazol-5-yl) methyl)-9H-purin-6-amine]

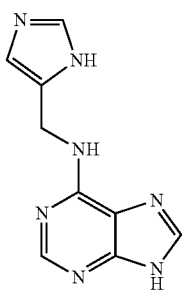

¹H NMR (400 MHz, DMSO) δ: 10.38 (s, 1H), 8.91 (d, J=1.6 Hz, 1H), 8.73 (s, 1H), 8.71 (s, 1H), 6.67 (d, J=1.6 Hz, 1H), 4.88 (s, 2H), 4.98 (d, J=5.4 Hz, 2H). LC-MS: m/z 216.1 [M+H]⁺.

MTK-0052/NB616-034 [(E)-N-(3-(furan-2-yL)propyl-9H-purin-6-amine]

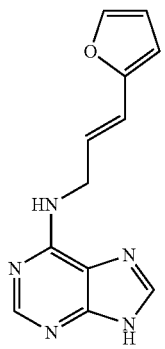 [SMILES: C(=C\c1ccco1)/CNc1ncnc2[nH]cnc12]

¹H NMR (400 MHz, DMSO) δ: 12.86 (s, 1H), 8.20 (s, 1H), 8.12 (d, J=2.4 Hz, 1H), 7.90 (s, 1H), 7.56-7.86 (m, 1H), 6.59-6.35 (m, 3H), 6.23 (dd, J=13.5, 8.0 Hz, 1H), 4.26 (s, 2H). LC-MS: m/z 241.7 [M+H]⁺.

MTK-0053/NB616-036 [N-(3-(furan-2-yl)propyl)-9H-purin-6-amine]

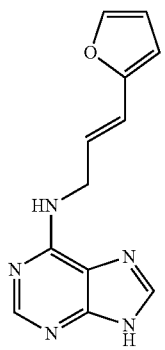 [SMILES: C(=C\c1ccco1)/CNc1ncnc2[nH]cnc12]

¹H NMR (400 MHz, DMSO) δ: 8.72 (s, 1H), 8.45 (s, 1H), 8.08 (s, 1H), 7.48 (s, 1H), 6.32 (s, 1H), 6.12 (s, 1H), 3.53 (s, 2H), 2.60-2.74 (m, 2H), 1.82-1.95 (m, 2H). LC-MS: m/z 243.5 [M+H]⁺.

MTK-0066/NB607-025 [N, N'-(furan-2, 5-diylbis(methylene))bis(9H-purin-6-amine)]

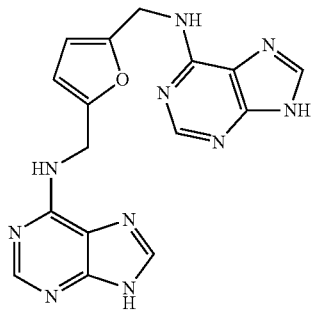 [SMILES: c1nc(NCc2ccc(CNc3ncnc4[nH]cnc34)o2)c2nc[nH]c2n1]

¹H NMR (400 MHz, DMSO) δ: 4.66 (br. s., 4H), 6.11 (s, 2H), 8.03 (br. s., 2H), 8.10 (s, 2H), 8.19 (br. s., 2H), 8.27 (br. s., 1H), 12.98 (br. s., 2H). LC-MS (m/z) 363.25 [M+1−1]⁺.

MTK-0074/NB607-029 [N((5-(aminomethyl)furan-2-yl)methyl)-9H-purin-6-amine]

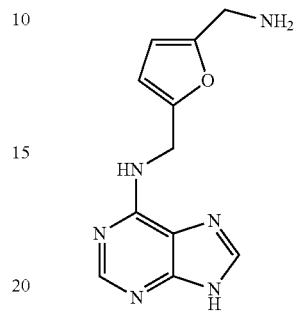

¹H NMR (400 MHz, DMSO) δ: 3.71 (s, 2H), 4.68 (br. s., 2H), 6.17 (s, 2H), 8.01 (br. s., 1H), 8.13 (s, 1H), 8.22 (s, 1H). LCMS (m/z) 228.09 [M-16]+.

MTK-0078/NB616-057 [N-((1H-imidazol-2-yl)methyl)-9H-purin-6-amine]

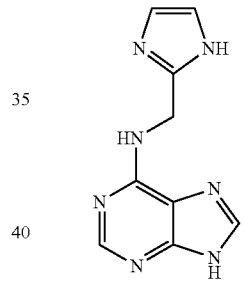

1H NMR (400 MHz, DMSO) δ: 13.10 (s, 1H), 8.96 (s, 1H), 8.23 (s, 1H), 8.19 (s, 1H), 7.25 (s, 2H), 4.88 (s, 2H). LC-MS: m/z 216.1 [M+H]⁺.

C. General Procedure 3:

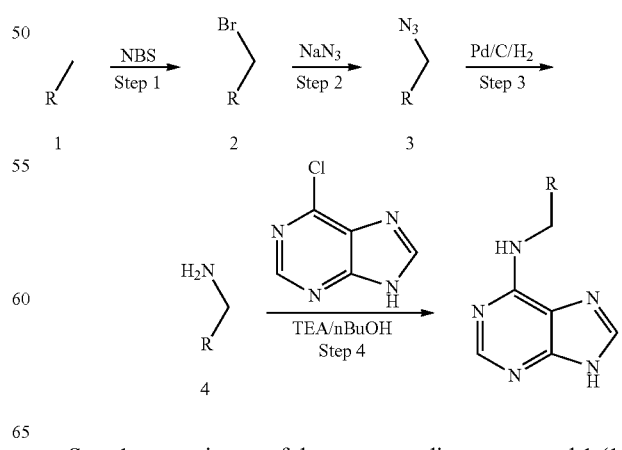

Step 1: to a mixture of the corresponding compound 1 (1 mmol) in CCl₄ (50 mL), was added NBS (1.2 mmol). The mixture was stirred at a reflux temperature until LCMS indicated completion of the reaction. The mixture was then cooled to room temperature, filtered, and the filtrate was concentrated in vacuo to afford the crude compound 2, which was purified by a flash chromatography or used directly for the next step without purification.

Step 2: the same procedure as General procedure 2, step 3

Step 3: the same procedure as General procedure 2, step 4

Step 4: the same procedure as General procedure 1

MTK-0011/NB571-079 [N-(pyrimidin-4-ylmethyl)-9H-purin-6-amine]

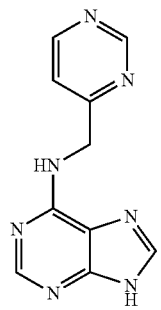

$^1$H NMR (Methanol-d$_4$) δ: 9.11 (s, 1H), 8.70 (d, J=5.2 Hz, 1H), 8.24 (s, 1H), 8.13 (s, 1H), 7.53 (d, J=5.2 Hz, 1H), 4.97 (br, 2H). LC-MS: m/z 228.2 [M+H]$^+$.

MTK-0023/NB571-075 [N-(pyridazin-3-ylmethyl)-9H-purin-6-amine]

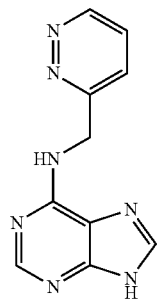 [SMILES: c1cnnc(CNc2ncnc3[nH]cnc23)c1]

$^1$H NMR (400 MHz, DMSO-d$_6$) δ: 12.93 (s, br, 1H), 9.13 (d, J=4 Hz, 1H), 9.11 (s, 1H), 8.18 (m, 2H), 7.62 (m, 2H), 5.00 (s, 2H). LC-MS: m/z 228.2 [M+H]$^+$.

MTK-0024/NB571-073 [N-(thiazol-5-ylmethyl)-9H-purin-6-amine]

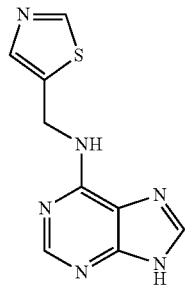 [SMILES: c1nc(NCc2cncs2)c2nc[nH]c2n1]

$^1$H NMR (400 MHz, DMSO-d$_6$) δ: 12.99 (br, 1H), 8.92 (s, 1H), 8.25 (s, 1H), 8.14 (s, 1H), 7.83 (d, J=3.6 Hz, 1H), 4.91 (br, 2H). LC-MS: m/z 233.3 [M+H]$^+$.

D. General Procedure 4:

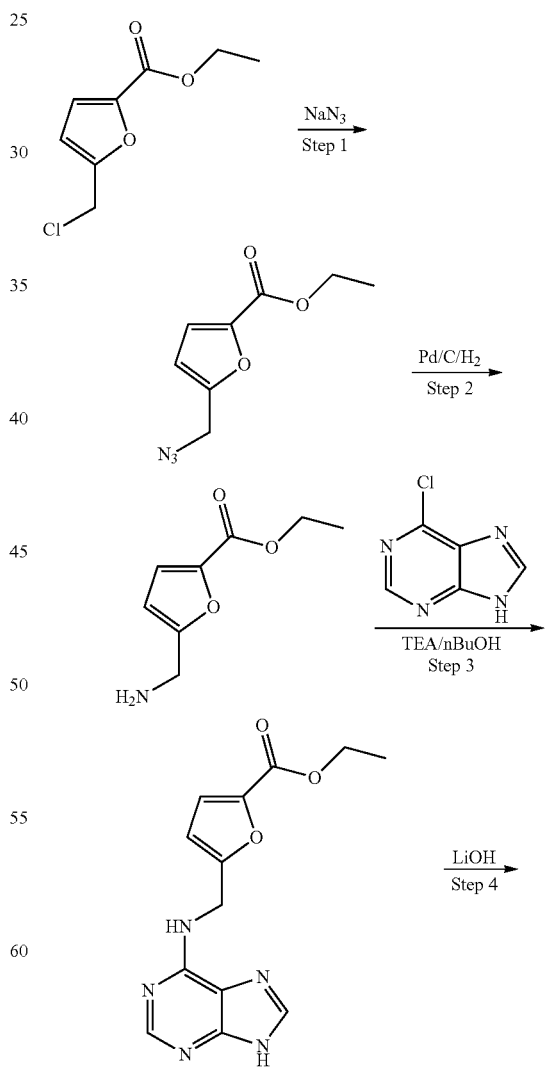

MTK-0033

-continued

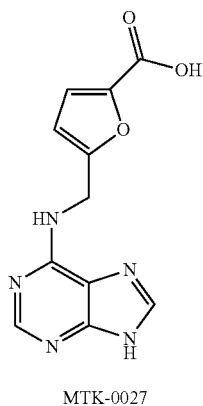

MTK-0027

Step 1: to a mixture of ethyl 5-(chloromethyl)furan-2-carboxylate (1 g, 5.32 mmol) in DMF (5 mL) was added NaN₃ (346 mg, 5.32 mmol). The mixture was heated to 50° C. overnight. TLC show consumption of the start material, one new spot appeared. The mixture was then diluted with brine (20 mL), extracted with DCM (10 mL, twice). The organic layer was combined, dried over anhydrous $Na_2SO_4$, filtered, and the filtrate was concentrated in vacuo to afford the crude product, which was used for the next step without purification.

Step 2: to a mixture of the crude ethyl 5-(azidomethyl)furan-2-carboxylate in ethanol was added 10% palladium on carbon (50 mg), the mixture was held stirring under $H_2$ atmosphere overnight. TLC show consumption of the start material, one new spot appeared. The mixture was filtered through a pad of Celite; the filtrate was concentrated to afford the crude product, which was used directly for the next step without purification. LC-MS: m/z 170.2 [M+H]⁺.

Step 3: the same procedure as General procedure 1

MTK-0027/NB612-033 [5-((9H-purin-6-ylamino)methyl)furan-2-carboxylic acid]

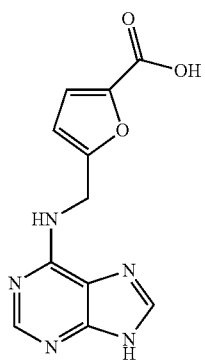

¹H NMR (400 MHz, DMSO-d₆) δ: 8.61 (br, 1H), 8.22 (s, 1H), 8.10 (s, 1H), 6.70 (br, 1H), 6.34 (br, 1H), 4.80 (br, 2H). LC-MS: m/z 260.2 [M+H]⁺.

MTK-0033/NB612-030 [ethyl 5 ((9H-purin-6-ylamino)methyl)furan-2-carboxylate]

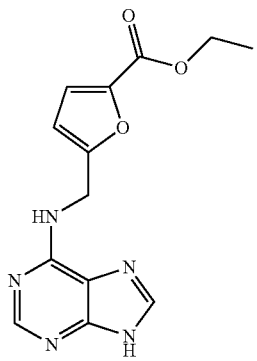 [SMILES: CCOC(=O)c1ccc(CNc2ncnc3[nH]cnc23)o1]

¹H NMR (400 MHz, DMSO-d₆) δ: 12.94 (br, 1H), 8.22 (br, 2H), 8.15 (s, 1H), 7.20 (d, J=3.6 Hz, 1H), 6.44 (d, J=3.2 Hz, 1H), 4.75 (br, 2H), 4.25 (q, J=7.2 Hz, 2H), 1.27 (t, J=7.2 Hz, 3H). LC-MS: m/z 288.3 [M+H]⁺.

Step 4: A mixture of ethyl 5-((9H-purin-6-ylamino)methyl)furan-2-carboxylate (120 mg, 0.42 mmol) and LiOH (35 mg, 0.84 mmol, 2.0 eq) in methanol (5 mL) was stirred at r.t. for 12 h. The mixture was adjusted to pH=7 with aqueous HCl (1 N) and then concentrated. The residue was purified by prep-HPLC to provide the desired product (76 mg, yield 70%).

E. General Procedure 5:

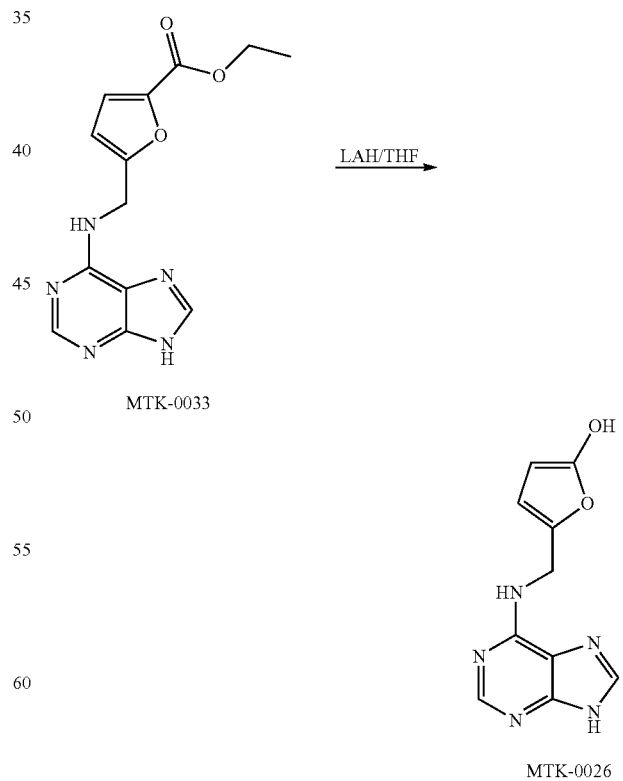

To the solution of ethyl 5-((9H-purin-6-ylamino)methyl)furan-2-carboxylate (120 mg, 0.42 mmol) in THF was added LiAlH$_4$ (30 mg, 0.84 mmol, 2.0 eq) at 0° C. The mixture was stirred at r.t. for 12 h. The reaction was quenched with Na$_2$SO$_4$.10H$_2$O. The mixture was filtered, and the filtrate was concentrated. The residue was purified by prep-HPLC to provide the desired product (48 mg, yield: 47%).

MTK-0026/NB612-034

$^1$H NMR (400 MHz, DMSO-d$_6$) δ: 8.20 (s, 1H), 8.11 (s, 1H), 7.96 (br, 1H), 4.72 (br, 2H), 4.33 (s, 2H). LC-MS: m/z 246.2 [M+H]$^+$.

F. General Procedure 6:

MTK-0054/NB607-009 [5(((9H-purin-6-y0amino) methyl)furan-2-carboxamidel

A mixture of MTK-0033 in ammonia solution was stirred in a sealed tube at 50° C. overnight. The mixture was concentrated in vacuo, the product was purified by a reversed phase flash chromatography. $^1$H NMR (400 MHz, DMSO-d$_6$) δ: 4.79 (br. s., 2H), 6.33 (d, J=3.22 Hz, 1H), 7.01 (d, J=3.49 Hz, 1H), 7.29 (br. s., 1H), 7.67 (br. s., 1H), 7.87 (br. s., 1H), 8.03 (s, 1H), 8.16 (s, 1H). LC-MS (m/z) 258.67 [M+H]$^+$.

G. General Procedure 7:

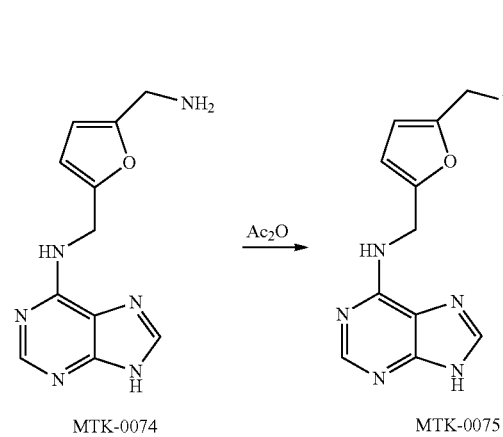

MTK-0075 MTK-0075/NB607-032 [N-45-4(9H-purin-6-yl)amino)methyl)furan-2-yl)methyl)acet-amide]

To a solution of N45-(aminomethyl)furan-2-yl)methyl)-9H-purin-6-amine (35 mg, 0.143 mmol) in DCM (2 mL) was added acetic anhydride (15 mg, 0.143 mmol), and the mixture was stirred at room temperature overnight. The solvent was then removed; the residue was purified by prepared-HPLC to get the desired compound as a white solid. $^1$H NMR (400 MHz, DMSO-d$_6$) δ: 1.82 (s, 3H), 4.19 (d, J=5.64 Hz, 2H), 4.71 (br. s., 2H), 6.08-6.21 (m, 2H), 7.91 (br. s., 1H), 8.09 (s, 1H), 8.19 (s, 1H), 8.28 (br. s., 1H). LCMS (m/z) 228.7 [M+1-1]$^+$.

H. General Procedure δ:

MTK-0056/NB612-066

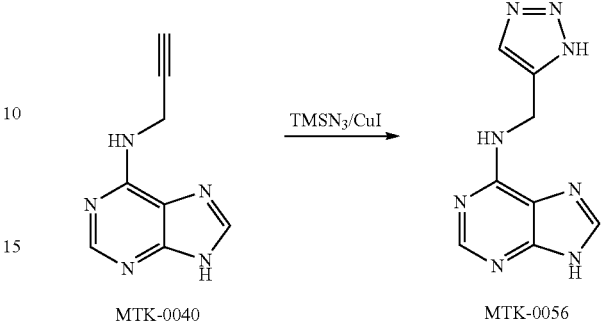

To the solution of N-(prop-2-yn-1-yl)-9H-purin-6-amine (80 mg, 0.46 mmol) in DMF/MeOH were added CuI (10 mg, 0.046 mmol, 0.1 eq) and TMSN$_3$ (80 mg, 0.7 mmol, 1.5 eq). The mixture was stirred at 100° C. for 12 h. The mixture was diluted with EA, washed with 30% aqueous NH$_4$OH, dried over MgSO$_4$, concentrated in vacuo and purified via prep-HPLC to give 4 mg of the desired product, yield 4%. $^1$H NMR (400 MHz, D$_2$0) δ: 8.23 (s, 1H), 8.13 (s, 1H), 7.84 (br, 1H), 4.80 (br, 2H), LC-MS: m/z 217.2 [M+H]$^+$.

I. General Procedure 9:

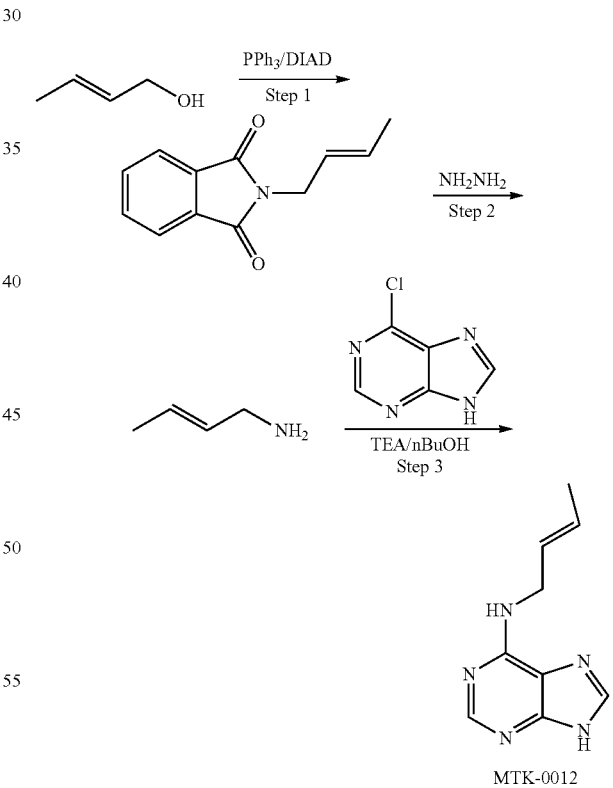

Step 1: To the solution of (E)-but-2-en-1-ol (2.1 g, 30 mmol) in THF (20 mL) were added PPh$_3$ (11.7 g, 45 mmol, 1.5 eq), O-Phthalimide (4 g, 30 mmol, 1.0 eq) and DIAD (9 g, 45 mmol, 1.5 eq). The mixture was stirred at 65° C. for 5 h. The mixture was concentrated and then purified by a flash chromatography to give the compound 2 (5 g, 80% yield). LC-MS: m/z 202.2 [M+H]$^+$.

Step 2: To the solution of 2 (2 g, 10.0 mmol) in THF (10 mL) was added hydrazine hydrate (500 mg, 10 mmol, 1.0 eq). The mixture was stirred at 80° C. for 3 hrs. The mixture was filtered, the filtrate was adjusted with HCl (3 N) to pH=3, and then concentrated in vacuo to afford crude product, which was used directly for the next step without further purification.

Step 3: the same procedure as General procedure 1.

MTK-0012/NB612-061 [(E)-N-(but-2-enyl)-9H-purin-6-amine]

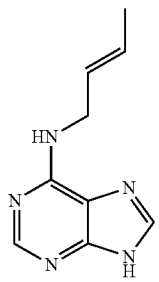

$^1$H NMR (400 MHz, DMSO-d$_6$) δ: 12.97 (br, 1H), 8.18 (s, 1H), 8.10 (s, 1H), 7.69 (br, 1H), 5.60 (br, 2H), 4.04 (br, 2H), 1.64-1.63 (m, 3H). LC-MS: m/z 190.2 [M+H]$^+$.

J. General Procedure 9:

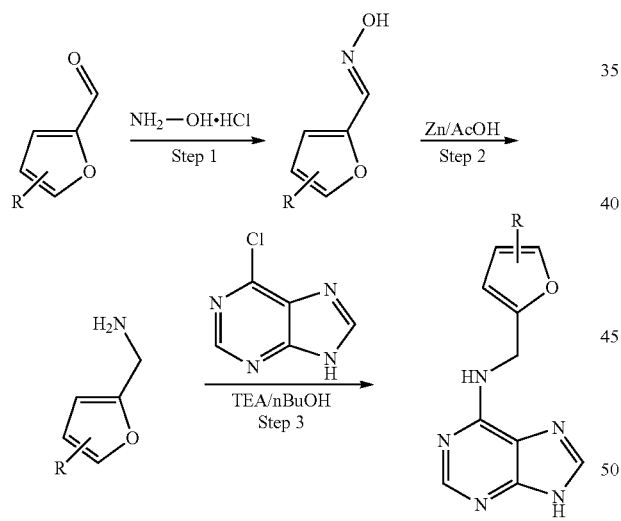

Step 1: To a solution of the corresponding furan-2-aldehyde (10 mmol) in EtOH (10 mL) was added hydroxylamine hydrochloride (11 mmol), and the mixture was refluxed for 2 h, when LCMS indicated the completion of the reaction. The solvent was removed, the residue was redissolved in 20 mL of ethyl acetate, and washed with water (2×20 ml), dried over Na$_2$SO$_4$, and concentrated under a reduced pressure. The residue was used in the next step without further purification.

Step 2: To a solution of the corresponding 2-(hydroxyimino)methyl)furan (10 mmol) in AcOH (20 mL) was added Zn dust (50 mmol), the mixture was stirred at room temperature overnight. The mixture was then filtered through a bunch funnel; the filtrate was collected and concentrated under reduced pressure. The residue was re-dissolved in ethyl acetate and washed with water (2×50 mL). The organic layer was concentrated under a reduced pressure and the residue was used in the next step without further purification.

Step 3: the same procedure as General procedure 1

MTK-0010/NB571-084 [N-((5-phenylfuran-2-yl)methyl)-9H-purin-6-amine]

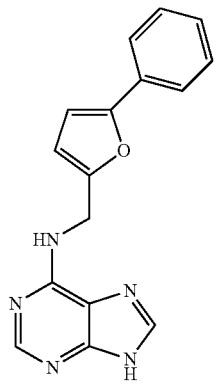 [SMILES: c1ccc(-c2ccc(CNc3ncnc4[nH]cnc34)o2)cc1]

$^1$H NMR (400 MHz, DMSO-d$_6$) δ: 12.97 (br, 1H), 8.25 (br, 1H), 8.14 (s, 2H), 7.65-7.63 (m, 2H), 7.42-7.38 (m, 2H), 7.28-7.24 (m, 1H), 6.85 (d, J=3.2 Hz, 1H), 6.36 (br, 1H), 4.77 (br, 2H). LC-MS: m/z 292.3 [M+H]$^+$.

MTK-0014/NB579-085 [N((4-phenylfuran-2-yl)methyl)-9H-purin-6-amine]

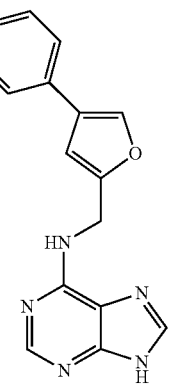

$^1$H NMR (400 MHz, DMSO-d$_6$) δ: 4.73 (br. s., 2H), 6.70 (br. s., 1H), 7.20-7.27 (m, 1H), 7.35 (t, J=7.66 Hz, 2H), 7.55 (d, J=7.25 Hz, 2H), 8.07 (s, 1H), 8.14 (br. s., 1H), 8.23 (br. s., 1H), 12.97 (br. s., 1H). LC-MS (m/z) 293.55 [M+H]$^+$.

MTK-0015/NB579-076 [5 ((9H-purin-6-ylamino)methyl)furan-2-carbonitrile]

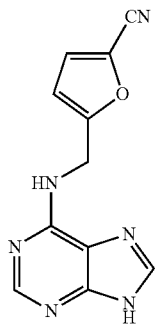 [SMILES: N#Cc1ccc(CNc2ncnc3[nH]cnc23)o1]

¹H NMR (400 MHz, DMSO-d₆) δ: 4.77 (br. s., 2H), 6.53 (d, J=3.76 Hz, 1H), 7.52 (d, J=3.49 Hz, 1H), 8.16 (s, 1H), 8.22 (s, 2H), 12.96 (br. s., 1H). LC-MS (m/z) 241.46 [M+H]⁺.

MTK-0022/NB579-039 [N-(benzofuran-2-ylmethyl)-9H-purin-6-amine]

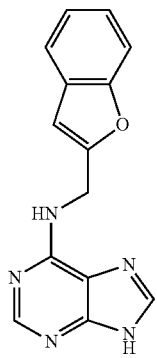

¹H NMR (400 MHz, DMSO-d₆) δ: 4.87 (br. s., 2H), 6.69 (s, 1H), 7.16-7.30 (m, 2H), 7.477.61 (m, 2H), 8.15 (s, 1H), 8.23 (s, 2H), 12.92 (br. s., 1H). LC-MS (m/z) 266.1 [M+H]⁺.

MTK-0046/NB579-092 [N((3-methylfuran-2-yl)methyl)-9H-purin-6-amine]

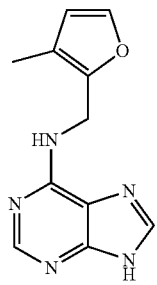 [SMILES: Cc1ccoc1CNc1ncnc2[nH]cnc12]

¹H NMR (400 MHz, DMSO-d₆) δ: 2.05 (s, 3H), 4.66 (br. s., 2H), 6.26 (s, 1H), 7.44 (br. s., 1H), 7.97 (br. s., 1H), 8.10 (br. s., 1H), 8.22 (br. s., 1H), 12.93 (br. s., 1H). LC-MS (m/z) 229.79 [M+H]⁺.

MTK-0055/NB607-008 [N((3-phenylfuran-2-yl)methyl)-9H-purin-6-amine]

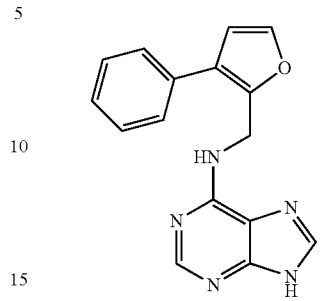

¹H NMR (400 MHz, DMSO-d₆) δ: 4.90 (br. s., 2H), 6.73 (d, J=1.61 Hz, 1H), 7.27-7.34 (m, 1H), 7.43 (t, J=7.66 Hz, 2H), 7.55-7.72 (m, 3H), 8.13 (s, 1H), 8.21 (s, 1H), 12.87 (br. s., 1H). LC-MS (m/z) 293.55 [M+H]⁺.

MTK-0081/NB607-038 N,N-bis((4, 5-dimethylfuran-2-yl)metliyl)-9H-purin-6-amine

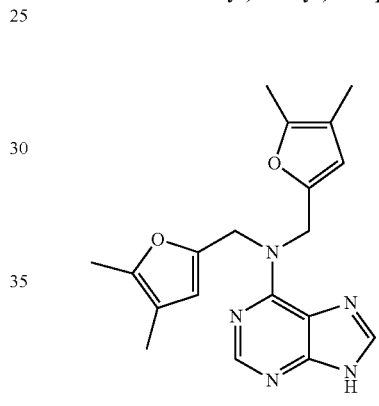

¹H NMR (400 MHz, METHANOL-d₄) δ: 1.89 (s, 6H), 2.13 (s, 6H), 5.16 (br. s., 4H), 6.04 (s, 2H), 8.03 (s, 1H), 8.27 (s, 1H). LCMS (m/z) 352.4 [M+H]⁺.

MTK-0082/NB607-041 N₄₄,₅-dimethylfuran-2-yl)methyl)-9H-purin-6-amine

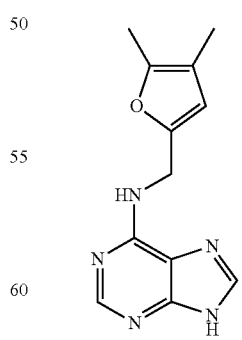

¹H NMR (400 MHz, DMSO-d₆) δ: 1.84 (s, 3H), 2.13 (s, 3H), 4.62 (br. s., 2H), 6.00 (s, 1H), 7.89 (br. s., 1H), 8.11 (s, 1H), 8.20 (s, 1H), 12.86 (br. s., 1H). LCMS (m/z) 244.1 [M+H]⁺.

K. General Procedure 10:

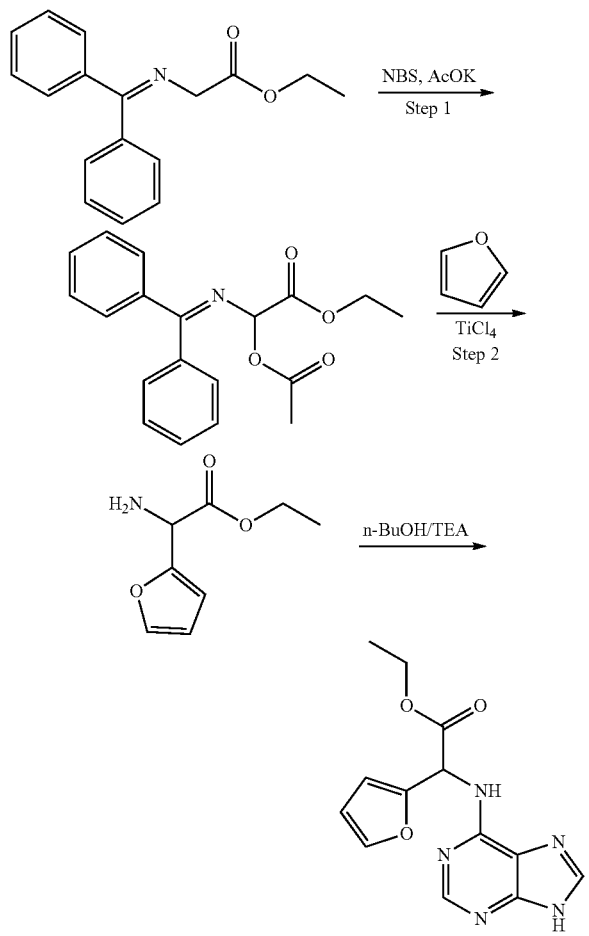

Step 1 and Step 2 follow the same procedure as the reference reported (Tetrahedron, 1988, vol. 44, #17, p. 5389-5402).

Step 3: The Same Procedure as General Procedure 1

MTK-0049/NB582-062 [ethyl 2-(9H-purin-6-ylamino)-2-(furan-2-yl)acetate]

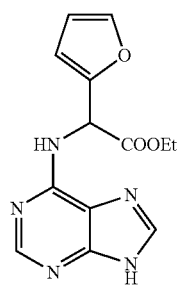 [SMILES: CCOC(=O)C(Nc1ncnc2[nH]cnc12)c1ccco1]

$^1$H NMR (Methanol-$d_4$) δ: 8.32 (s, 1H), 8.22-8.12 (m, 1H), 7.56 (d, J=1.1 Hz, 1H), 6.54 (d, J=3.3 Hz, 1H), 6.47 (dd, J=3.2, 1.9 Hz, 1H), 6.13 (s, 1H), 4.63 (s, 1H), 4.25 (qd, J=7.1, 2.0 Hz, 2H), 1.26 (t, J=7.1 Hz, 3H). LC-MS: m/z 288.3 [M+H]$^+$.

L. General Procedure 11:

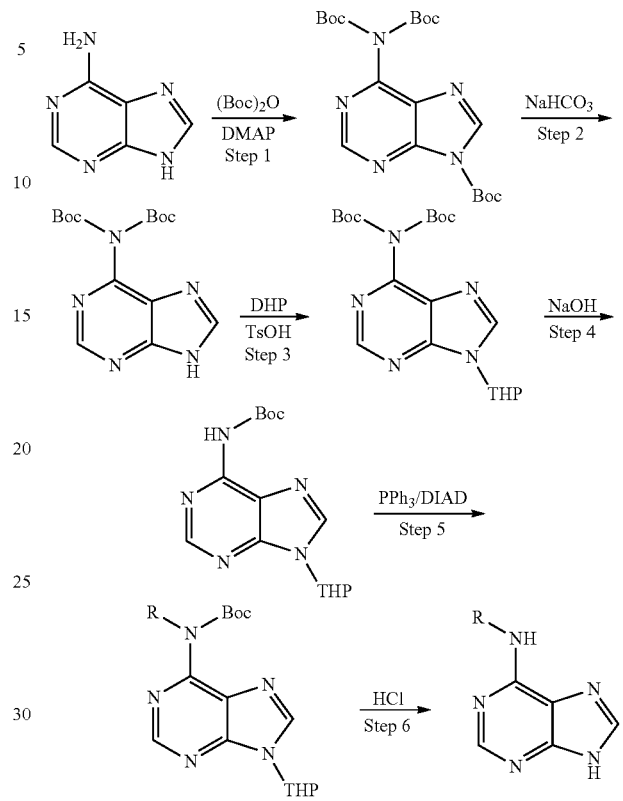

Step 1: To a suspension of 9H-purin-6-amine (1.35 g, 10.0 mmol), DMAP (0.12 g, 1.0 mmol) and TEA (3.03 g, 30.0 mmol) in 40 mL DCM was added (Boc)$_2$O (2.18 g, 10.0 mmol), the mixture was stirred at r.t for 4 hrs. The solvent was then removed, and the residue was directly used in the next step.

Step 2: The above residue was solved in 20 mL methanol, which was followed by adding 20% sodium bicarbonate solution (4 mL), the mixture was stirred at 50° C. for 2 hrs, which was then purified by a flash chromatography (PE/EA=6/1) to give white solid as the desired product. $^1$H NMR (400 MHz, DMSO) δ: 13.70 (s, 1H), 8.79 (s, 1H), 8.64 (s, 1H), 1.37 (s, 18H). LC-MS: m/z 336.4 [M+H]$^+$.

Step 3: A mixture of N,N-diboc-9H-purin-6-amine (3.0 g, 8.96 mmol) and DHP (1.5 g, 17.8 mmol), TsOH (0.05 g) in 30 mL ethyl acetate was stirred at 75° C. for 2 hrs. The solvent was then removed to afford a yellow solid as the desired product (3.8 g, 95% yield). LC-MS: m/z 420.6 [M+H]$^+$.

Step 4: To the above yellow solid in methanol (35 mL) was added sodium hydroxide solution (0.5 g in 3 mL water), the mixture was stirred at 35° C. for 2.5 hrs. The mixture was extracted with ethyl acetate (2×30 mL), the organic phase was combined and concentrated to give yellow solid (2.4 g, 84% yield) as the desired product tert-butyl 9-(tetrahydro-2H-pyran-2-yl)-9H-purin-6-ylcarbamate. LC-MS: m/z 320.4 [M+H]$^+$.

Step 5: To a solution of tert-butyl 9-(tetrahydro-2H-pyran-2-yl)-9H-purin-6-ylcarbamate (0.32 g, 1 mmol), the corresponding alcohol (1 mmol) and PPh3 (0.39 g, 1.5 mmol) in 10 mL anhydrous THF was added g DEAD (0.26, 1.5 mmol) dropwise at ice-cold temperature. The mixture was then stirred at r.t for another 16 hrs. The solvent was removed; the residue was purified by a flash chromatography to afford the desired product.

Step 6: To a solution of the above product in methanol was added 1 N HCl in MeOH, the mixture was stirred at 40° C. for 4 hrs. The solvent was then removed and washed with ethyl acetate to afford the desired compound. The disclosure provides for any of the following compounds or pharmaceutically acceptable salts, isomers, or tautomers thereof:

MTK-0016/NB616-33 [N-(cyclopentylmethyl)-9H-purin-6-amine]

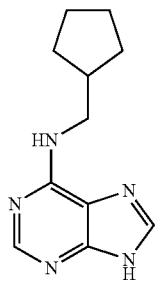 [SMILES: c1nc(NCC2CCCC2)c2nc[nH]c2n1]

$^1$H NMR (400 MHz, DMSO) δ: 9.88 (s, 1H), 8.56 (s, 2H), 3.58-3.53 (m, 2H), 2.24 (dt, J=15.0, 7.5 Hz, 1H), 1.78 (d, J=7.0 Hz, 2H), 1.66-1.58 (m, 2H), 1.52 (dd, J=9.7, 4.9 Hz, 2H), 1.30 (ddd, J=16.7, 12.1, 4.7 Hz, 2H). LC-MS: m/z 217.7 [M+H]$^+$.

MTK-0017/NB616-28B [N-(cyclopent-3-enylmethyl)-9H-purin-6-amine]

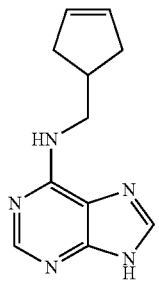

$^1$H NMR (400 MHz, DMSO) δ: 10.02 (s, 1H), 8.62-8.65 (d, J=17.5 Hz, 2H), 5.71 (s, 2H), 3.58 (t, J=6.5 Hz, 2H), 2.67 (d, J=8.1 Hz, 1H), 2.53-2.55 (m, 1H), 2.48-2.49 (m, 1H), 2.16 (dd, J=14.1, 4.8 Hz, 2H). LC-MS: m/z 215.7 [M+H]$^+$.

MTK-0019/NB616-24 [(E)-N-(2-methylbut-2-enyl)-9H-purin-6-amine]

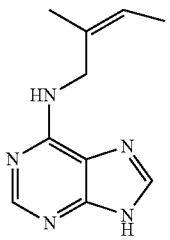

$^1$H NMR (400 MHz, DMSO) δ: 9.95 (s, 1H), 8.60 (t, J=24.1 Hz, 2H), 5.48 (d, J=6.3 Hz, 1H), 4.18 (d, J=5.3 Hz, 2H), 1.67 (s, 3H), 1.59 (d, J=6.7 Hz, 3H). LC-MS: m/z 203.9 [M+H]$^+$.

MTK-0020/NB616-22 [(E)-N-(2-ethylbut-2-enyl)-9H-purin-6-amine]

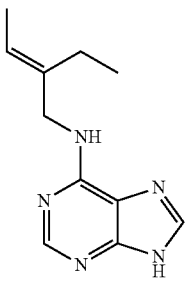 [SMILES: C/C=C(\CC)CNc1ncnc2[nH]cnc12]

$^1$H NMR (400 MHz, DMSO) δ: 9.78 (s, 1H), 8.61 (d, J=20.4 Hz, 2H), 5.46 (q, J=6.6 Hz, 1H), 4.22 (d, J=4.5 Hz, 2H), 2.10 (q, J=7.5 Hz, 2H), 1.60 (d, J=6.8 Hz, 3H), 0.99 (t, J=7.6 Hz, 3H). LC-MS: m/z 217.9 [M+H]$^+$.

MTK-0029/NB616-10A [N-(but-2-ynyl)-9H-purin-6-amine]

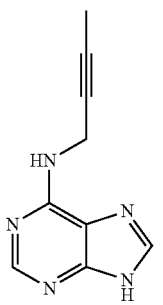

$^1$H NMR (400 MHz, DMSO) δ: 12.89 (s, 1H), 8.23 (s, 1H), 8.15 (d, J=11.7 Hz, 1H), 7.89 (s, 1H), 4.23 (s, 2H), 1.75 (s, 3H). LC-MS: m/z 187.8 [M+H]$^+$.

MTK-0031/NB616-15 [N-(furan-3-ylmethyl)-9H-purin-6-amine]

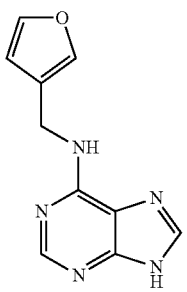 [SMILES: c1nc(NCc2ccoc2)c2nc[nH]c2n1]

$^1$H NMR (400 MHz, DMSO) δ: 10.16 (s, 1H), 8.58-8.78 (m, 2H), 7.76 (s, 1H), 7.66 (s, 1H), 6.58 (s, 1H), 4.71 (s, 2H). LC-MS: m/z 216.2 [M+H]$^+$.

MTK-0045/NB616-33 [N-(isoxazol-3-ylmethyl)-9H-purin-6-amine]

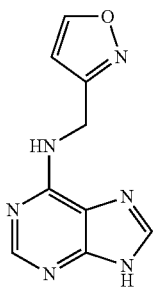 [SMILES: c1nc(NCc2ccon2)c2nc[nH]c2n1]

$^1$H NMR (400 MHz, DMSO) δ: 12.93 (s, 1H), 8.21 (s, 1H), 8.11 (s, 1H), 7.68 (s, 1H), 7.58 (d, J=11.6 Hz, 1H), 6.90 (s, 1H), 4.62 (s, 2H). LC-MS: m/z 216.8 [M+H]$^+$.

MTK-0048/NB616-20 [7-(furan-2-ylmethyl)-8,9-dihydro-7H-imidazo[4, 5, 1-de]pteridine]

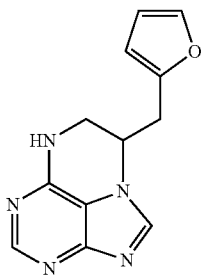 [SMILES: c1coc(CC2CNc3ncnc4ncn2c34)c1]

$^1$H NMR (400 MHz, DMSO) δ: 11.13 (s, 1H), 8.12 (d, J=21.0 Hz, 1H), 7.90 (s, 1H), 7.56 (dd, J=1.8, 0.7 Hz, 1H), 6.37 (dd, J=3.1, 1.9 Hz, 1H), 6.26-6.14 (m, 1H), 5.04 (d, J=4.2 Hz, 1H), 4.06 (dd, J=11.7, 9.9 Hz, 1H), 3.70 (dd, J=11.8, 5.3 Hz, 1H), 3.34 (s, 1H), 3.313.17 (m, 2H).

MTK-0065/NB616-45 [N-(oxazol-5-ylmethyl)-9H-purin-6-amine]

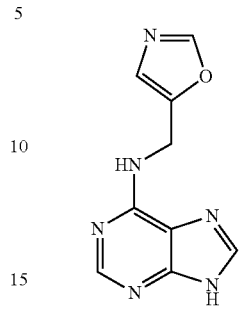

$^1$H NMR (400 MHz, DMSO) δ: 9.94 (s, 1H), 8.68 (s, 1H), 8.60 (s, 1H), 8.35 (s, 1H), 7.19 (s, 1H), 4.95 (s, 2H). LC-MS: m/z 217.0 [M+H]$^+$.

M. General Procedure 12:

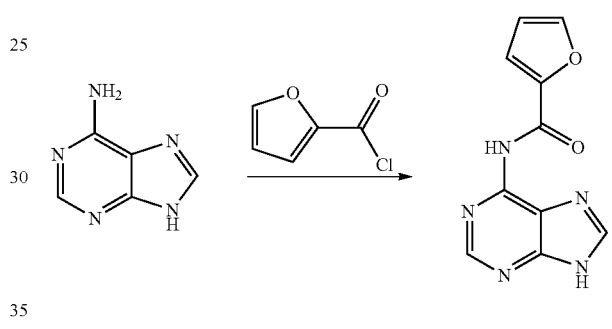

MTK-0032/NB579-035 [N-(9H-purin-6-yl)furan-2-carboxamide]

To a solution of furan-2-carbonyl chloride (1 g, 7.6 mmol) and 9H-purin-6-amine (1.05 g, 7.6 mmol) in THF 50 ml was added pyridine (1 mL), then the mixture was stirred at 60° C. overnight. The mixture was cooled to room temperature, remove the solvent, the residue was purified by prepared-HPLC to get the desired compound as a white solid. $^1$H NMR (400 MHz, DMSO) δ: 6.78 (dd, J=3.63, 1.75 Hz, 1H), 7.72-7.79 (m, 1H), 8.04-8.08 (m, 1H), 8.49 (s, 1H), 8.72 (s, 1H), 12.13 (br. s., 1H). LC-MS (m/z) 230.48 [M-F1-1]$^+$.

N. General Procedure 13:

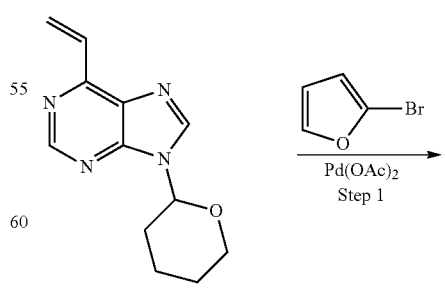

Reference compound
Tetrahedron, 1999,
vol 55, # 1
p. 211-228

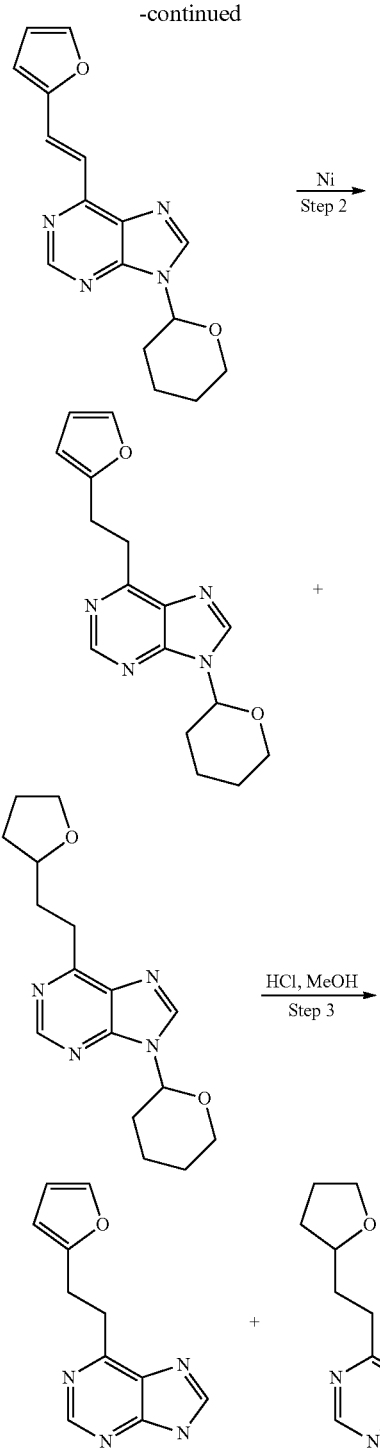

Step 1: To a solution of 9-(tetrahydro-2H-pyran-2-yl)-6-vinyl-9H-purine (300 mg, 1.31 mmol) and 2-bromofuran (383 mg, 2.62 mmol) in 10 mL of DMF was added D1PEA, (253.5 mg, 1.97 mmol), Pd(OAc)$_2$ (29.4 mg, 0.131 mmol) at r.t. under N$_2$. The mixture was heated at 105° C. for 40 min. TLC showed complete consumption of the starting material. The mixture was concentrated in vacuo and purified via column chromatography (petroleum ether/EtOAc) to give 65 mg of the product as a yellow solid. LC-MS (m/z) 297.3 [M+H]+.

Step 2: To a solution of (E)-6-(2-(furan-2-yl)vinyl)-9-(tetrahydro-2H-pyran-2-yl)-9H-purine (65 mg, 0.321 mmol) in 10 mL of MeOH was added Raney Nickel (5 mg) at r.t. The mixture was heated at 25° C. for 4 h. TLC showed complete consumption of the starting material after this time. The mixture was concentrated in vacuo and purified via flash column chromatography (petroleum ether/EtOAc) to give the product.

Step 3: A solution of (6-(2-(furan-2-yl)ethyl)-9-(tetrahydro-2H-pyran-2-yl)-9H-purine (20 mg, 0.067 mmol) in 2 mL of MeOH (1 M HCl gas in MeOH) was stirred at 25° C. for 1 h. TLC (petroleum ether/EtOAc, silica gel plate) showed complete consumption of the starting material after this time. The mixture was concentrated in vacuo and purified via column chromatography (DCM/McOH) to give the product as a white solid.

MTK-0071/NB582-096 [6-(2-(furan-2-yl)ethyl)-9H-purine]

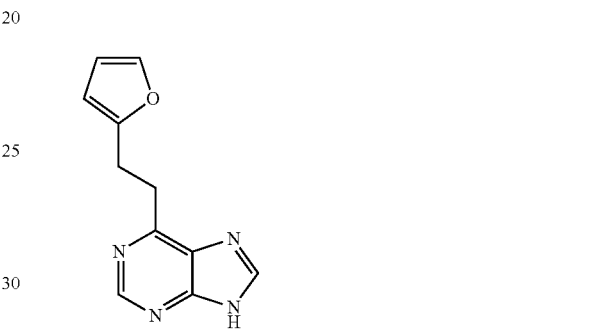

$^1$H NMR (Methanol-d$_4$) δ: 8.84 (s, 1H), 8.49 (s, 1H), 7.32 (d, J=1.2 Hz, 1H), 6.24 (dd, J=3.0, 2.0 Hz, 1H), 6.06-5.95 (m, 1H), 3.51 (t, J=7.6 Hz, 2H), 3.25 (t, J=7.7 Hz, 2H). LCMS (m/z) 215.2 [M+H]$^+$.

MTK-0077/NB582-96B [6-(2-(tetrahydrofuran-2-yl)ethyl)-9H-purine]

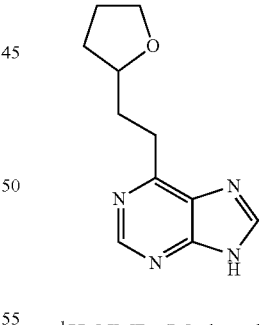

$^1$H NMR (Methanol-d$_4$) δ: 8.82 (s, 1H), 8.50 (s, 1H), 4.01-3.82 (m, 2H), 3.73 (dd, J=14.2, 7.9 Hz, 1H), 3.30-3.18 (m, 2H), 2.16-2.00 (m, 3H), 2.00-1.85 (m, 2H), 1.60 (ddd, J=16.0, 12.0, 7.5 Hz, 1H). LC-MS (m/z) 219.3 [M+H]$^+$.

General Procedure 14:

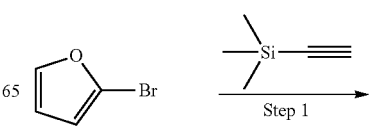

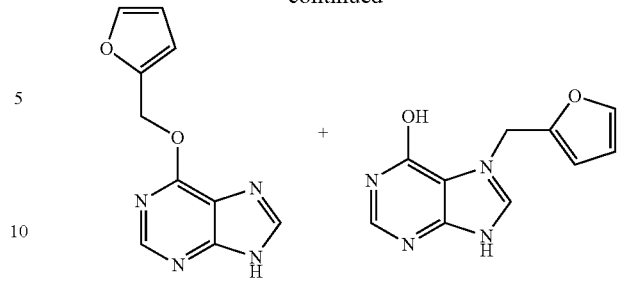

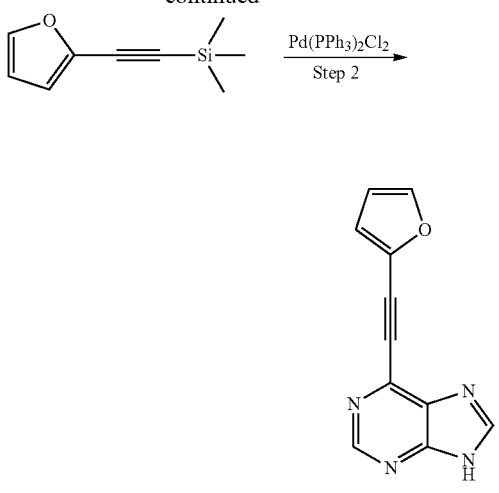

Step 1: follow reference procedure as WO2011/6061 A1

Step 2: To a solution of (furan-2-ylethynyl)trimethylsilane (200 mg, 1.211 mmol) and 6-iodo-9H-purine (298 mg, 1.211 mmol) in 10 mL of anhydrous THF was added Pd(PPh$_3$)$_2$Cl$_2$ (84.3 mg, 0.12 mmol), CuI (46 mg, 0.24 mmol), and TBAF (1M in THF, 1.82 mL) at r.t. under N$_2$. The mixture was stirred at 35° C. for 8 h. TLC showed complete consumption of the starting material after this time. The mixture was concentrated in vacuo and purified via column chromatography (DCM/MeOH) to give 150 mg of the product as a white solid.

MTK-0076/NB582-095 [6-(furan-2-ylethynyl)-9H-purine]

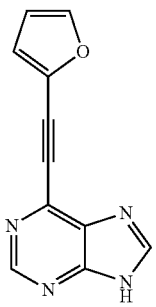 [SMILES: C(#Cc1ncnc2[nH]cnc12)c1ccco1]

$^1$H NMR (Methanol-d$_4$) δ: 8.92 (s, 1H), 8.61 (s, 1H), 7.77-7.71 (m, 1H), 7.17-7.09 (m, 1H), 6.65 (dd, J=3.5, 1.9 Hz, 1H). LC-MS (m/z) 211.2 [M+H]$^+$.

General Procedure 15:

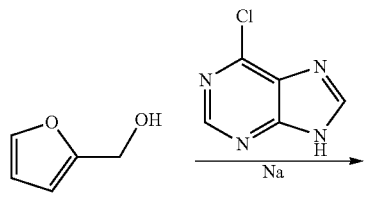

A mixture of Na (100 mg) in furan-2-ylmethanol (5 mL) was held stirring at room temperature for several hrs until all the Na was dissolved. To this mixture was added 6-chloro-9H-purine (500 mg) then the mixture was stirred at 100° C. overnight. The mixture was quenched with aqueous NH$_4$Cl, and then concentrated. The products were isolated by a revered phase flash column chromatography.

MTK-0070/NB644-001 [6-(furan-2-ylmethoxy)-9H-purine]

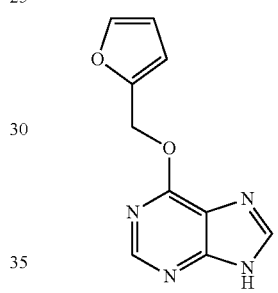

$^1$H NMR (400 MHz, DMSO) δ: 12.39 (s, 1H), 8.29 (s, 1H), 7.98 (s, 1H), 7.62 (s, 1H), 6.43-6.45 (m, 2H), 5.60 (s, 2H). LC-MS: m/z 217.2 [M+H]$^+$.

MTK-0073/NB644-01C [7-(furan-2-ylmethyl)-7H-purin-6-ol]

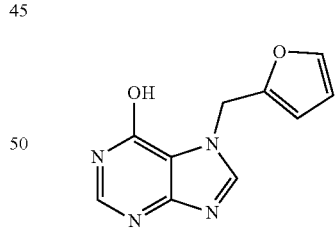

$^1$H NMR (400 MHz, DMSO) δ: 12.35 (s, 1H), 8.27 (s, 1H), 7.70 (s, 1H), 7.49 (s, 1H), 6.33 (s, 1H), 6.07 (s, 1H), 4.03 (s, 2H). LC-MS: m/z 217.2 [M+H]$^+$.

General Procedure 16:

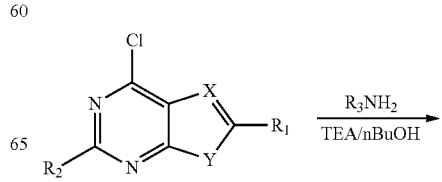

-continued

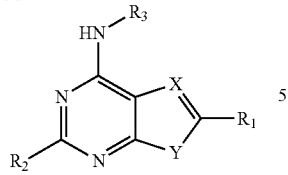

The same procedure as general procedure 1

MTK-0051/NB612-73 [N-(furan-2-ylmethyl)-1H-pyrazolo [3, 4-d]pyrimidin-4-amine]

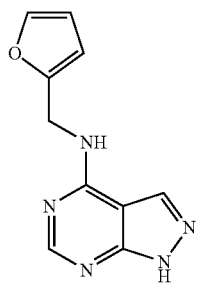 [SMILES: c1coc(CNc2ncnc3[nH]ncc23)c1]

$^1$H NMR (400 MHz, DMSO-d$_6$) δ: 13.44 (s, 1H), 8.64 (br., 1H), 8.26 (s, 1H), 8.14 (s, 1H), 7.61 (s, 1H), 6.42-6.41 (m, 1H), 6.35-6.34 (m, 1H), 4.73 (d, J=5.6 Hz, 2H). LC-MS: m/z 216 [M+H]$^+$.

MTK-0057/NB616-40 [N-(furan-2-ylmethyl)-1H-imidazo[4, 5-c]pyridin-4-amine]

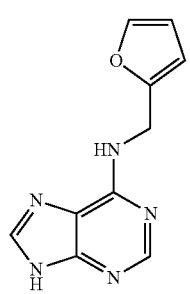 [SMILES: c1coc(CNc2ncnc3[nH]cnc23)c1]

NMP replaced n-BuOH as reaction solvent.

$^1$H NMR (400 MHz, DMSO-d$_6$) δ: 13.52 (s, 1H), 9.50 (s, 1H), 8.48 (s, 1H), 7.70 (d, J=6.9 Hz, 2H), 7.64 (s, 1H) 7.18 (d, J=6.9 Hz, 1H), 6.56-6.37 (m, 2H), 4.97 (s, 2H). LC-MS: m/z 214.7 [M+H]$^+$.

MTK-0058/NB612-83 [N-(furan-2-ylmethyl)-3H-imidazo[4, 5-b]pyridin-7-amine]

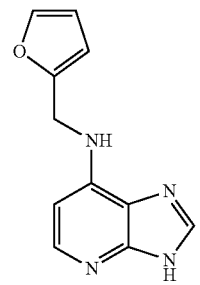 [SMILES: c1coc(CNc2ccnc3[nH]cnc23)c1]

$^1$H NMR (400 MHz, DMSO-d$_6$) δ: 12.60 (br., 1H), 8.04 (s, 1H), 7.86 (br., 1H), 7.56 (s, 1H), 7.06 (br., 1H), 6.38 (br., 2H), 6.30 (br., 1H), 4.63 (br., 2H). LC-MS: m/z 215 [M+H]$^+$.

MTK-0059/NB612-85 [N-(furan-2-ylmethyl)-1H-pyrazolo[3, 4-b]pyridin-4-amine]

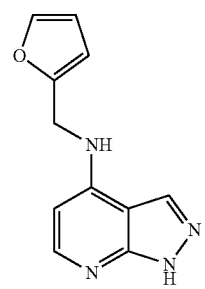 [SMILES: c1coc(CNc2ccnc3[nH]ncc23)c1]

$^1$H NMR (400 MHz, DMSO-d$_6$) δ: 13.03 (br., 1H), 8.13 (s, 1H), 7.99 (d, J=5.2 Hz, 1H), 7.74 (t, J=5.6 Hz, 1H), 7.61 (s, 1H), 6.41-6.40 (m, 1H), 6.26-6.24 (m, 1H), 4.50 (d, J=6.0 Hz, 2H). LC-MS: m/z 215 [M+H]$^+$.

MTK-0061/NB573-094 [N-(furan-2-ylmethyl)-8-phenyl-9H-purin-6-amine]

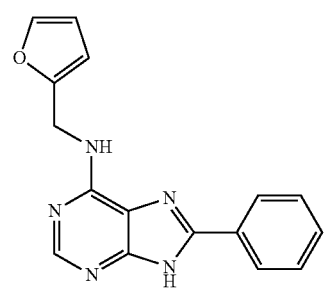 [SMILES: c1ccc(-c2nc3c(NCc4ccco4)ncnc3[nH]2)cc1]

$^1$H NMR (DMSO-d$_6$) δ: 13.47 (s, 1H), 8.23 (s, 1H), 8.16-8.14 (m, 3H), 7.56-7.49 (m, 4H), 6.37 (d, J=2.4 Hz, 1H), 6.27 (d, J=2.4 Hz, 1H), 4.71 (s, 2H). LC-MS: m/z 292 [M+H]$^+$.

113

MTK-0062/NB616-41 [N-(furan-2-ylmethyl)-1H-pyrazolo[4,3-c]pyridin-4-amine]

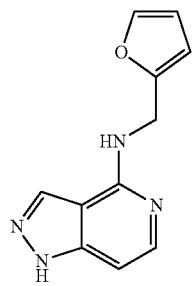

NMP replaced n-BuOH as reaction solvent.

¹H NMR (400 MHz, DMSO-d₆) δ: 13.02 (s, 1H), 8.22 (s, 1H), 7.74-7.65 (m, 2H), 7.58 (dd, J=1.7, 0.6 Hz, 1H), 6.67 (dd, J=5.6, 0.6 Hz, 1H), 6.39 (dd, J=3.1, 1.7 Hz, 1H), 6.28 (d, J=3.1 Hz, 1H), 4.68 (d, J=5.6 Hz, 2H). LC-MS: m/z 214.8 [M+H]⁺.

MTK-0063/NB573-096 [N-(furan-2-ylmethyl)-2-methyl-9H-purin-6-amine]

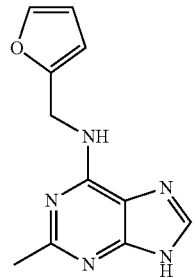 [SMILES: Cc1nc(NCc2ccco2)c2nc[nH]c2n1]

¹H NMR (DMSO-d₆) δ: 12.72 (s, 1H), 8.02 (s, 1H), 7.89 (br. s., 1H), 7.54 (s, 1H), 6.36 (s, 15 1H), 6.24 (s, 1H), 4.70 (s, 2H), 2.42 (s, 3H). LC-MS: m/z 230 [M+H]⁺.

MTK-0064/NB573-097 IN-(furan-2-ylmethyl)-8-methyl-9H-purin-6-amine]

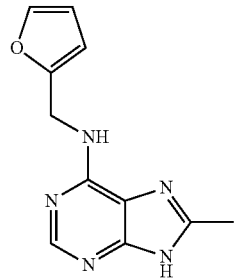 [SMILES: Cc1nc2c(NCc3ccco3)ncnc2[nH]1]

1H NMR (DMSO-d₆) δ: 12.59 (s, 1H), 8.13 (s, 1H), 7.83 (br. s., 1H), 7.54 (s, 1H), 6.36 (d, J=2.8 Hz, 1H), 6.22 (d, J=2.8 Hz, 1H), 4.70 (s, 2H), 2.45 (s, 3H). LC-MS: m/z 230.2 [M+H]⁺.

114

MTK-0068/NB571-098 [N-6-(furan-2-ylmethyl)-9H-purine-2,6-diamine]

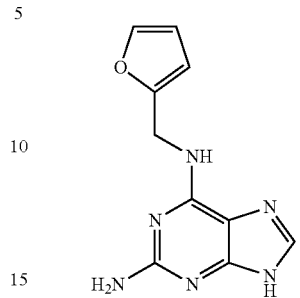

¹H NMR (DMSO-d₆) δ: 12.12 (s, 1H), 7.66 (s, 1H), 7.53-7.44 (m, 2H), 6.36 (s, 1H), 6.24 (s, 1H), 5.75 (s, 2H), 4.65 (s, 2H). LC-MS: m/z 231 [M+H]⁺.

MTK-0069/NB612-042 [N-(furan-2-ylmethyl)imidazo[1,2-a]pyridin-5-amine]

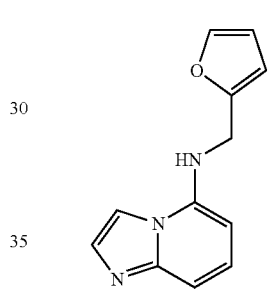

¹H NMR (400 MHz, DMSO-d₆) δ: 8.05 (s, 1H), 7.66-7.58 (m, 2H), 7.51 (t, J=5.6 Hz, 1H), 7.33-7.22 (m, 1H), 6.93 (d, J=8.8 Hz, 1H), 6.49-6.38 (m, 2H), 6.12 (d, J=7.6 Hz, 1H), 4.54 (d, J=5.8 Hz, 2H). LC-MS: m/z 214.7 [M+H]⁺.

MTK-0080/NB645-011 [N-(6-((furan-2-ylmethyl)amino)-9H-purin-2-yl)acetamide]

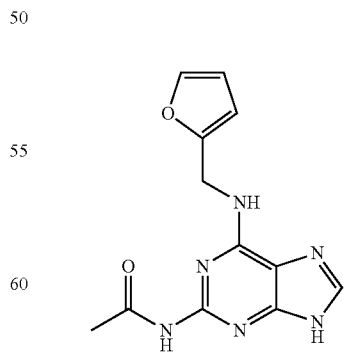

¹H NMR (DMSO-d₆ and D20) δ: 7.67 (s, 1H), 7.50 (S, 1H), 6.36-6.35 (m, 1H), 6.30 (d, J=3.2 Hz, 1H), 4.71 (s, 2H), 2.15 (s, 3H). LC-MS: m/z 231 [M+H]⁺.

General procedure 17:

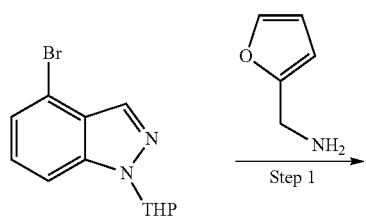

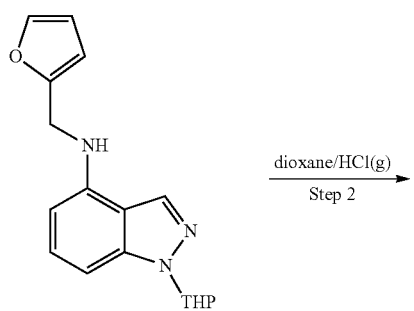

Step 1: A mixture of 4-bromo-1-(tetrahydro-2H-pyran-2-yl)-1H-indazole (140 mg, 0.5 mmol), furan-2-ylmethanamine (50 mg, 0.5 mmol), t-BuONa (75 mg, 0.75 mmol), xanphos (20 mg) and $Pd_2(dba)_3$ (20 mg) in toluene (3 ml) was stirred at 110° C. under micro-wave conditions for 0.5 h. The mixture was concentrated and purified by flash column chromatography (0-30% EtOAc in petroleum ether) gave the desired product N-(furan-2-ylmethyl)-1-(tetrahydro-2H-pyran-2-yl)-1H-indazol-4-amine (60 mg, 40% yield) LC-MS: m/z 298 [M+H]$^+$.

Step 2: To a solution of N-(furan-2-ylmethyl)-1-(tetrahydro-2H-pyran-2-yl)-1H-indazol-4-amine (60 mg, 0.2 mmol) in dioxane (2 mL) was added a solution of HCl in dioxane (4 N, 1 mL), then stirred at 40° C. for 5 h. The reaction mixture was concentrated and 0.2 mL of conc. $NH_3$ in water was added. Purification by a flash reverse column chromatography (0-60% MeOH in water) gave the product N-(furan-2-ylmethyl)-1H-indazol-4-amine (15 mg, 35% yield).

MTK-0067/NB645-001 [N-(furan-2-ylmethyl)-1H-indazol-4-amine]

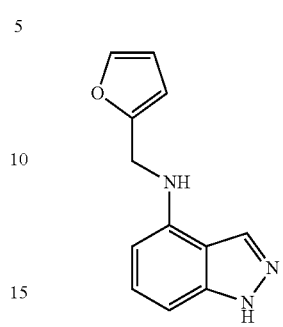

$^1$H NMR (methanol-d$_4$) δ: 8.13 (s, 1H), 7.43 (s, 1H), 7.16 (t, J=8.0 Hz, 1H), 6.80 (d, J=8.4 Hz, 1H), 6.35-6.34 (m, 1H) 6.28 (d, J=2.4 Hz, 1H), 6.24 (d, J=7.6 Hz, 1H), 4.47 (s, 2H). LC-MS: m/z 214 [M+H]$^+$.

General Procedure 18:

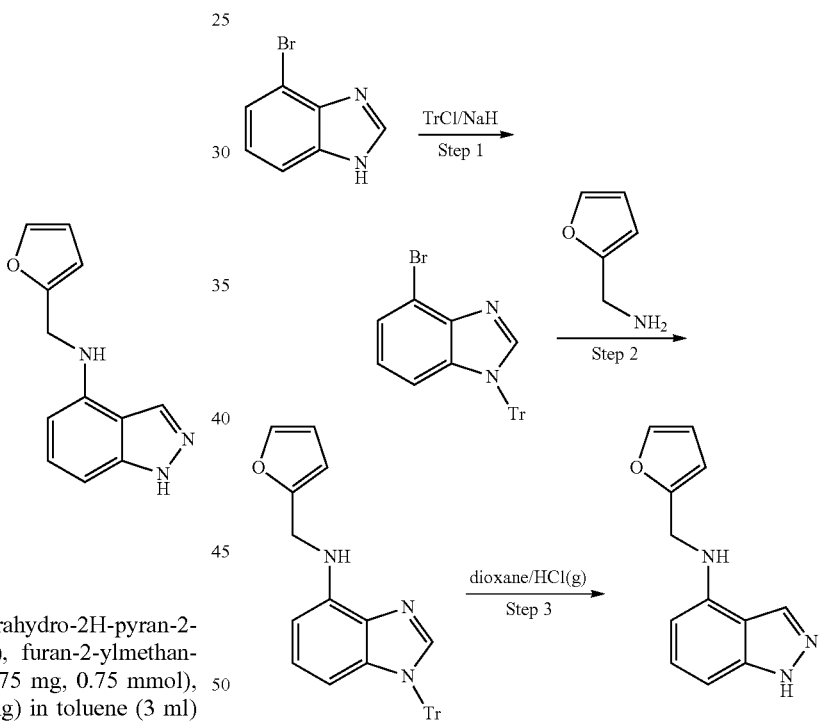

Step 1: To a solution of 4-bromo-1H-benzo[d]imidazole (300 mg, 1.52 mmol) in dry THF (15 mL) was added NaH (60%, 172 mg, 1.82 mmol), then stirred at rt for 0.5 h. (chloromethanetriyl) tribenzene (551 mg, 1.58 mmol) and cat. tetrabutylammonium iodide were added. The reaction mixture was heated to reflux for 4 h, then quenched with water and extracted with EtOAc. The organic layer was dried and concentrated. Purified by a flash column chromatography (0-30% EtOAc in petroleum ether) to get the target product 4-bromo-1-trityl-1H-benzo[d]imidazole (460 mg, 69% yield). LC-MS: m/z 439 [M+H]$^+$.

Step 2: It is same as general procedure 17 step 1.

Step 3: It is same as general procedure 17 step 2.

MTK-0079/NB645-006 [N-(furan-2-ylmethyl)-1H-benzo[d]imidazol-4-amine]

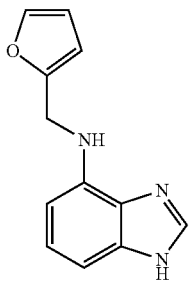 [SMILES: c1coc(CNc2cccc3[nH]cnc23)c1]

$^1$H NMR (DMSO-d$_6$) δ: 8.01 (s, 1H), 7.56 (s, 1H), 7.54 (s, 1H), 6.94 (d, J=8.0 Hz, 1H), 6.79-6.77 (m, 1H), 6.38-6.29 (m, 3H), 5.91 (t, J=6.0 Hz, 1H), 4.46 (d, J=6.4 Hz, 2H). LC-MS: m/z 214 [M+H]$^+$.

O. General Procedure 19:

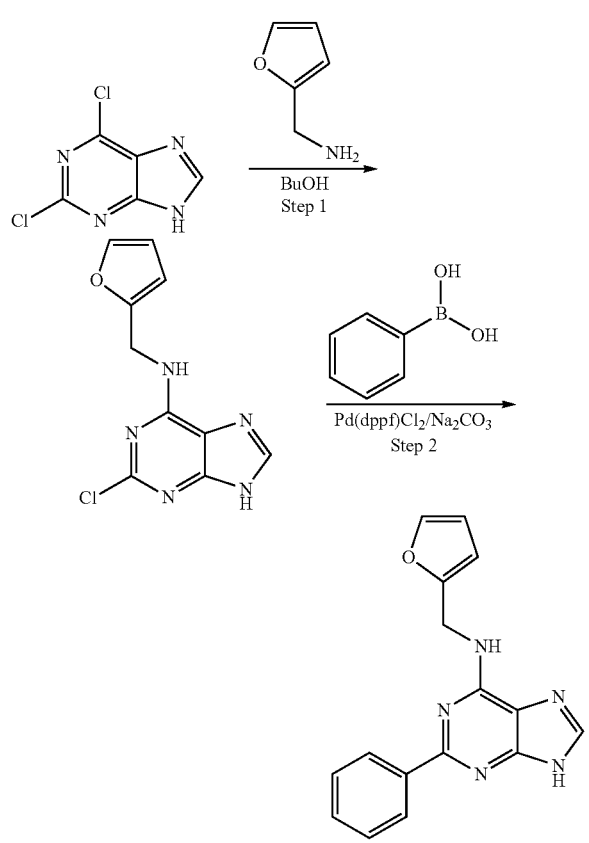

Step 1: It is same as general procedure 16.

Step 2: A mixture of 6-chloro-N-(furan-2-ylmethyl)-1H-pyrazolo[3, 4-d]pyrimidin-4-amine (250 mg, 1 mmol), phenylboronic acid (160 mg, 1.3 mmol), Na$_2$CO$_3$ (320 mg, 3 mmol) and Pd(dppf)Cl$_2$ (25 mg) in DMF/H$_2$O (4/1, 6 ml) was stirred at 120° C. under micro-wave conditions for 2 h. The mixture was portioned between water and EtOAc. The organic layer was washer with water and brine, dried and concentrated, purified by a reverse phase flash column chromatography (0-60% MeOH in water) then lyophilization to give the desired product N-(furan-2-ylmethyl)-2-phenyl-9H-purin-6-amine as a white solid (40 mg, 14% yield).

MTK-0072/NB645-002 [N-(furan-2-ylmethyl)-2-phenyl-9H-purin-6-amine]

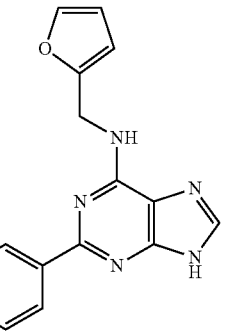

$^1$H NMR (methanol-d$_4$) δ: 8.43-8.41 (m, 2H), 8.08 (s, 1H), 7.46-7.45 (m, 4H), 6.39-6.37 (m, 2H), 4.95 (s, 2H). LC-MS: m/z 292 [M+H]$^+$.

P. General Procedure 20:

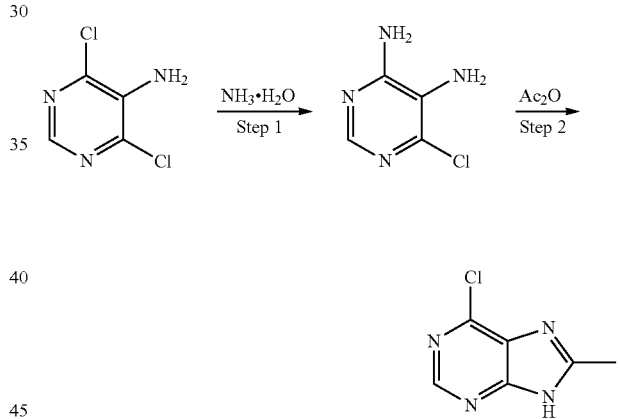

Step 1: The suspension of 4, 6-dichloropyrimidin-5-amine (1.64 g, 10 mmol) in 5 mL of conc. NH$_3$ in water in sealed tube was stirred at 100° C. overnight. The solid was collected by filtration and dried under vacuum to give the desired product 6-chloropyrimidine-4, 5-diamine as a yellow solid (1.2 g, 83% yield). LC-MS: m/z 145 (M-F1-1).

Step 2: A solution of 6-chloropyrimidine-4, 5-diamine (432 mg, 3 0 mmol) in acetic anhydride (5 mL) was heated to 120° C. for overnight. The reaction mixture was concentrated and water was added, and then extracted with EtOAc. The organic layer was separated and washed with water and brine, dried over Na$_2$SO$_4$ and concentrated. The residue was suspended in POCl$_3$ (10 mL) and heated to 120° C. for overnight. The reaction was concentrated and diluted with EtOAc and sat. Nat-100$_3$ solution. The organic layer was separated and washed with water and brine, dried over Na$_2$SO$_4$ and concentrated. Purified by a flash column chromatography (0-30% EtOAc in petroleum ether) to give the desired product 6-chloro-8-methyl-9H-purine (263 mg, 52% yield). LC-MS: m/z 169 [M+H]$^+$.

Q. General Procedure 21:

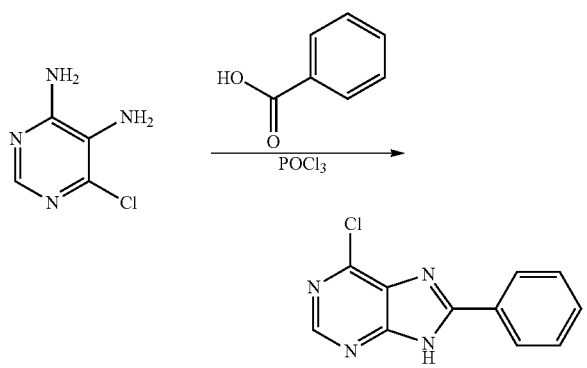

To a mixture of 6-Chloro-4, 5-diaminopyrimidine (432 mg, 3.0 mmol), NH₄Cl (954 mg, 18 mmol) and benzoic acid (366 mg, 3 mmol) in the flask was added phosphoryl chloride (16.0 mL), and the resulting mixture was stirred for 18 h at 100° C. The reaction mixture was evaporated to remove excess phosphoryl chloride, and the residue was added to water (20 mL). The precipitate was filtered and purified by flash chromatography (0 to 5% Methanol/DCM) to afford the 6-chloro-8-phenyl-9H-purine (480 mg, 69% yield) as a yellow solid. LC-MS: m/z 169 [M+H]⁺.

R. General procedure 22:

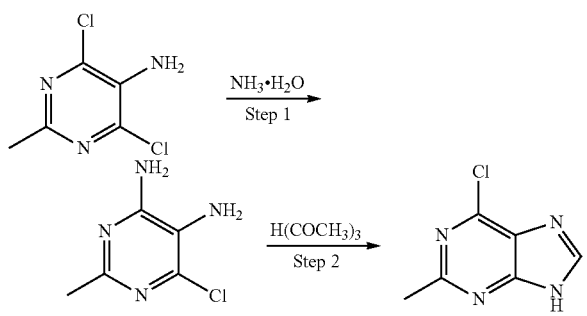

Step 1: It is same as general procedure 20 step 1.
Step 2: A solution of 6-chloro-2-methylpyrimidine-4, 5-diamine (474 mg, 3.0 mmol) in trimethoxymethane (15 mL) was heated to reflux overnight. The reaction mixture was concentrated and water was added, extracted with EtOAc. The organic layer was separated and washed with water and brine, dried over Na₂SO₄, and concentrated. Purification by a flash column chromatography (0-30% EtOAc in petroleum ether) gave 6-chloro-2-methyl-9H-purine (250 mg, 50% yield). LC-MS: m/z 169 (M-FIV).

S. General Procedure 23:

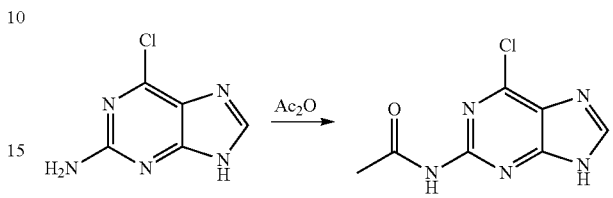

Step 1: To acetic anhydride (25 mL) at 180° C. was added 6-chloro-9H-purin-2-amine (2 g) and the mixture was heated to reflux overnight. The reaction mixture was cooled to rt. and ethoxyethane was added. The precipitate was collected by filtration and dried. Further purified by a reverse phase flash column chromatography (0-60% MeOH in water) gave N-(6-chloro-9H-purin-2-yl)acetamide (450 mg, 17% yield) as a white solid. LC-MS: m/z 212 (M+FH)⁺.

Example 2: Modulation of PINK1

This example demonstrates the ability of the compounds to modulat PINK1 activity in an in vitro experiment.

We grew SH-SYSY cells in 1:1 mix of DMEM and F12 supplemented with 10% FBS and Pen/Strep (1×) antibiotics on 96 well plates (~5,000 cells/well) at 37 degrees Celsius in 90 ul per well. We added 10 ul of 10× mix of the compounds identified below in a DMSO and medium mix to the cells. (min. 2 wells per compound per plate), allowed it to incubate for 96 hours at 37 degrees Celsius, then added 25 uM MG-132 for 16 hours (a proteasome inhibitor that triggers apoptosis; this toxicity is known to be opposed by PINK1). Following incubation with MG-132 we added 100 ul of Promega Caspase-Glo® reagent directly to each well to lyse cells and provide a luminescent Caspase 3/7 substrate peptide to quantify caspase cleavage activity. All of the values in Table 2 are presented as a % of kinetin's caspase cleavage values (kinentin was run as a positive control in parallel to the analogs of kinetin shown below).

TABLE 2

| | | Run1 | | | Run2 | | | Run3 | | |
|---|---|---|---|---|---|---|---|---|---|---|
| | Structure | Compound (avg as % kinetin) | DMSO Control (avg as % kinetin) | Cells Only (avg as % kinetin) | Compound (avg as % kinetin) | DMSO Control (avg as % kinetin) | Cells Only (avg as % kinetin) | Compound (avg as % kinetin) | DMSO Control (avg as % kinetin) | Cells Only (avg as % kinetin) |
| MTK-48 | 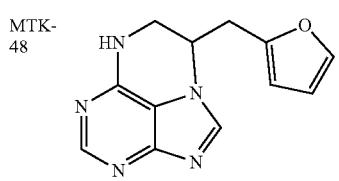 | 92% | 127% | 115% | 122% | 135% | 137% | 95% | 108% | 107% |

TABLE 2-continued

| | Structure | Run1 | | | Run2 | | | Run3 | | |
|---|---|---|---|---|---|---|---|---|---|---|
| | | Compound (avg as % kinetin) | DMSO Control (avg as % kinetin) | Cells Only (avg as % kinetin) | Compound (avg as % kinetin) | DMSO Control (avg as % kinetin) | Cells Only (avg as % kinetin) | Compound (avg as % kinetin) | DMSO Control (avg as % kinetin) | Cells Only (avg as % kinetin) |
| MTK-51 | 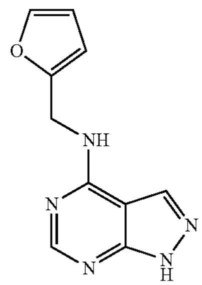 [SMILES: c1coc(CNc2ncnc3[nH]ncc23)c1] | 80% | 127% | 115% | 92% | 135% | 137% | | | |
| MTK-57 | 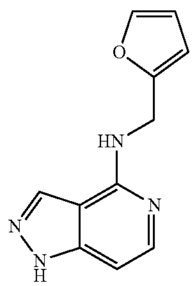 [SMILES: c1coc(CNc2nccc3[nH]ncc23)c1] | 97% | 108% | 102% | 112% | 135% | 137% | 100% | 108% | 107% |
| MTK-58 | 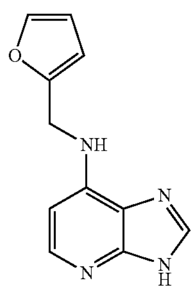 [SMILES: c1coc(CNc2ccnc3[nH]cnc23)c1] | 94% | 108% | 102% | 108% | 135% | 137% | | | |
| MTK-59 | 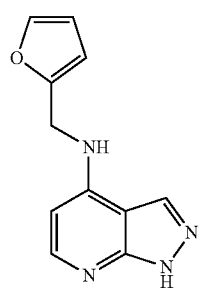 [SMILES: c1coc(CNc2ccnc3[nH]ncc23)c1] | 72% | 127% | 115% | 108% | 135% | 137% | | | |
| MTK-62 | 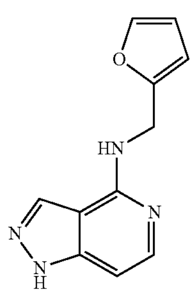 [SMILES: c1coc(CNc2nccc3[nH]ncc23)c1] | 88% | 108% | 102% | 132% | 135% | 137% | | | |

TABLE 2-continued

|  | | Run1 | | | Run2 | | | Run3 | | |
| --- | --- | --- | --- | --- | --- | --- | --- | --- | --- | --- |
| | Structure | Compound (avg as % kinetin) | DMSO Control (avg as % kinetin) | Cells Only (avg as % kinetin) | Compound (avg as % kinetin) | DMSO Control (avg as % kinetin) | Cells Only (avg as % kinetin) | Compound (avg as % kinetin) | DMSO Control (avg as % kinetin) | Cells Only (avg as % kinetin) |
| MTK-64 | [structure] | 79% | 108% | 102% | 120% | 135% | 137% | 93% | 108% | 107% |
| MTK-68 | [structure] | 95% | 132% | 132% | | | | | | |

Example 3

In Vivo Parkinson's Disease Study

Parkinson's disease (PD) is the second most common neurodegenerative disorder in the United States. The predominant motor symptoms of PD including slow movement, resting tremor, rigidity, and gait disturbance, are caused by the loss of dopaminergic neurons in the substantia nigra (SN). Although the aetiology of PD remains unknown, both genetic and environmental factors appear to play a role (Paisan-Ruiz et al., 2004; Vila & Przedborski, 2004). The neurotoxicant 1-methyl-4-phenyl-1, 2, 3, 6-tetrahydropyridine (MPTP) is a specific dopaminergic neuronal toxin. MPTP is converted to 1-methyl-4-phenyl pyridinium (MPP+) by astroglia and then causes specific dopaminergic neuronal death in the SN, thus leading to the clinical symptoms of PD in humans, primates and mice (Uhl et al., 1985). For this reason, MPTP-induced dopaminergic neurotoxicity in mice is widely used as a model for PD research. It has been largely reported that MPP+ causes neurodegeneration of dopaminergic neurones in vitro and provides a useful model of Parkinson's disease in vitro. The neurotrophins brain derived neurotrophic factor (BDNF) and glial derived neurotrophic factor (GDNF) have been suggested to reduce the MPP+-induced neurodegeneration in vitro (Hung & Lee, 1996); (Hou et al., 1996). This study investigated the neuroprotective effect of Mitokinin test compound (kinetin) in function on time of pre-incubation and concentration on mouse primary mesencephalic cultures injured by exposure to 1-methyl-4-phenylpyridinium (MPP+), a Parkinson' disease model in vitro. BDNF at 10 ng/ml will be used as a positive control in this study.

Protocol
Primary Cultures of Medium Spiny Neurons

Mouse dopaminergic neurons are cultured as described by Schinelli et al., 1988 and Viswanath et al., 2001. Briefly pregnant female mouse of 14 days gestation are killed by cervical dislocation (Mouse C57Bl/6; Janvier Labs) and the foetuses are removed from the uterus. The embryonic midbrains are removed and placed in ice-cold medium of Leibovitz (L15; PanBiotech; ref: PO4-27055, batch: 4290114) containing 2% of Penicillin-Streptomycin (PS; PanBiotech; ref: P06-07100; batch: 4810114) and 1% of bovine serum albumin (BSA; PanBiotech; Ref: P06-1391100, batch: K030913). Only the ventral portions of the mesencephalic flexure are used for the cell preparations as this is the region of the developing brain rich in dopaminergic neurons. The midbrains are dissociated by trypsinisation for 20 min at 37° C. (Trypsin EDTA IX; PanBiotech Ref: P10-023100; batch: 1681013). The reaction is stopped by the addition of Dulbecco's modified Eagle's medium (DMEM; PanBiotech Ref PO4-03600; batch: 9710913) containing DNAase I grade II (0.1 mg/ml; Panbiotech, ref: P60-37780100; batch: H130919) and 10% of foetal calf serum (FCS; Invitrogen; ref: 10270-098; batch: 41Q4120K). Cells are then mechanically dissociated by 3 passages through a 10 ml pipette. Cells are then centrifuged at 180×g for 10 min at 4° C. temperature on a layer of BSA (3.5%) in L15 medium. The supernatant is discarded and the cells of pellet is re-suspended in a defined culture medium consisting of Neurobasal (Invitrogen, ref: 21103; batch: 1556347) supplemented with B27 (2%; Invitrogen; ref: 17504; batch: 1446691), L-glutamine (2 mM; PanBiotech; ref: PO4-80100; batch: 6620314) and 2% of PS solution. Viable cells are counted in a Neubauer cytometer using the trypan blue exclusion test. The cells are seeded at a density of 70 000 cells/well in 96 well-plates (wells are pre-coated with poly- L-lysine (Greiner)) and are cultured at 37° C. in a humidified air (95%)/CO2 (5%) atmosphere. Half of the medium are changed every 2 days with fresh medium. In these conditions, after 5 days of culture, astrocytes are present in the culture and release growth factor allowing neurons differentiation. Five to six percents of the neuronal cell population are dopaminergic neurons.

MPP+ Exposure and Drug Treatment

Briefly, on day 5 of culture, the medium was removed and fresh medium was added, without or with kinetin (Sigma ref 48130) at 100 µM, 50 µM, 25 µM and with and without BDNF 10 ng/ml for 2 days, 6 days or 10 days. On day 7, 11 or 15 of culture, the medium was removed and fresh medium was added, without or with kinetin and without or with BDNF at 10 ng/ml and with $MPP^+$ (Sigma; ref: D048; batch 092M4729V; at 4 µM) in the culture medium. The test compounds were let during the MPP+ intoxication. The following conditions were done:
Control (DMSO 0.1%)
MPP (4 i.t.M, 48 h)/vehicle
MPP+ (4 i.t.M, 48 h)+kinetin at 100 µM, 50 i.tM, 25 i.tM
MPP+ (4 i.t.M, 48 h)+BDNF (10 ng/ml)
End Point Evaluation: Measure of Total Number of TH Positive Neurons.

After 48 hours of intoxication in presence or absence of test compounds, cells were fixed by a solution of 4% paraformaldehyde (Sigma, ref 6148, batch: SLBH4356V) for 20 min at room temperature, the control conditions was fixed as well following the same procedure. The cells were then permeabilized and non-specific sites were blocked with a solution of phosphate buffered saline (PBS; PanBiotech; ref: PO4-36500, Batch: 9650614) containing 0.1% of saponin (Sigma; ref: S7900, Batch: BCBJ8417V) and 1% fetal calf serum (FCS) for 15 min at room temperature. Cells were incubated with Monoclonal Anti-Tyrosine Hydroxylase antibody produced in mouse (TH, antibodies-Sigma; ref: T1299, Batch: 101M4796) PBS containing 1% FCS, 0.1% saponin, for 2 h at room temperature. Antibody against TH stained dopaminergic neuron.

The antibody was revealed with Alexa Fluor 488 goat anti-mouse IgG (Molecular probe, ref: A11001, Batch: 1397999) in PBS with 1% FCS, 0.1% saponin, for 1 hat room temperature. Nuclei of cells were labelled by a fluorescent marker (Hoechst solution, Sigma; ref: B1155, Batch: 011M4004V) in the same solution.

For each condition, 10 pictures per well were taken using InCell Analyzer™ 2000 (GE Healthcare) with 20× magnification. Images of each culture well were taken in same condition. Analysis of cell bodies of TH positive neurons was performed using Developer software (GE healthcare). A total of 6 data per experimental condition were provided. Six wells per condition (1 culture) were done to assess neuronal survival. Data are expressed in percentage of control condition. Statistical analyses were done on the different conditions using ANOVA test following by Fisher's PLSD test.

Statistics

The data were expressed as mean+s.e.mean (of 6 data per condition). A global analysis of the data were performed using a one-way analysis of variance (ANOVA). The level of significance is set at $p<0.05$.

Results

A. Effect of Kinetin Pre-Incubated During 2 Days on Dopaminergic Neurons after a MPP+ Injury FIG. 1 depicts the effects of Kinetin pre-incubating during 2 days on survival of mouse primary dopaminergic neuron culture injured by MPP (4 µM) expressed in percentage of control (mean±s.e.m; *$p<0.05$; $P<0.01$; *$P<0.005$; $MPP^+$vs control; one way Anova followed by Dunnett's test). $MPP^+$ when applied at 4 µM for 48 h induced a large and significant decrease of TH positive neurons (~50%). Application of BDNF (10 ng/mL) displays a strong protective effect against $MPP^+$ injury (87%, ***, $p<0.001$).

Pre-incubation of Kinetin 2 days before the injury shows a protective effect on TH neuron survival against $MPP^+$ in a dose-dependent manner. Only the strongest concentration of Kinetin (100 µM) induces a statistically significant rescue of dopaminergic neuron survival (70%, **, $p<0.01$). In conclusion, Kinetin at 100 µM (pre-incubated 2 days before intoxication) is able to protect TH positive neurons form MPP injury.

Figure 2:
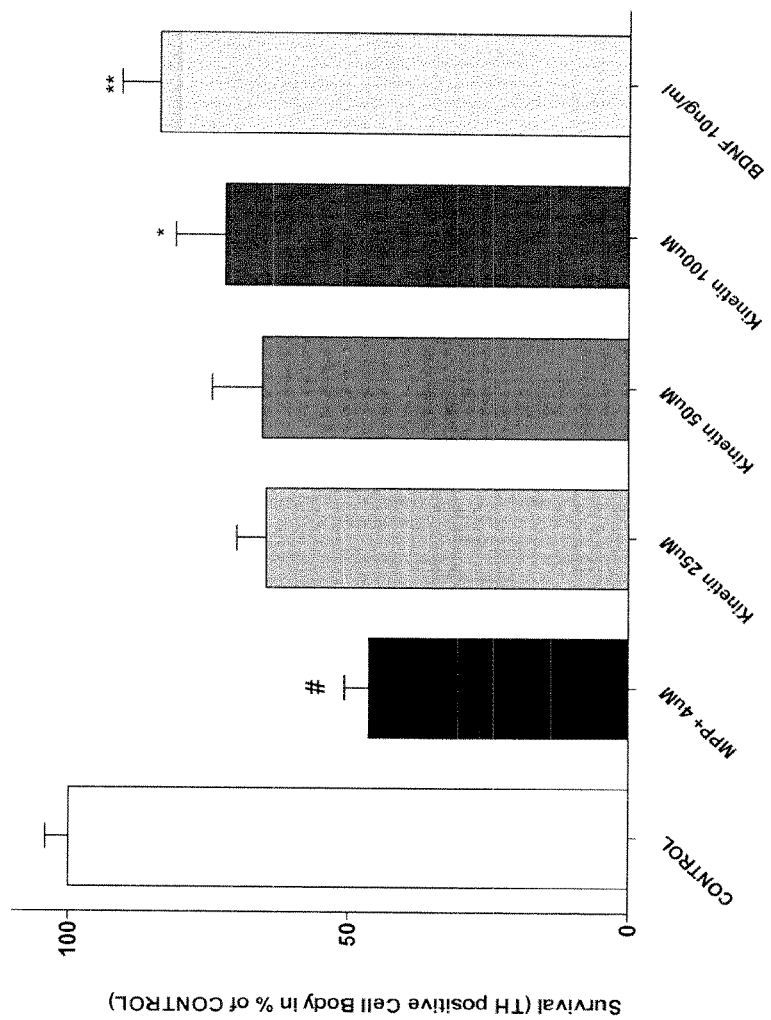
FIG. 2 depicts the effect of Kinetin pre-incubated during 6 days on survival of mouse primary dopaminergic neuron culture injured by MPP+ (4 µM) expressed in percentage of control. (mean+/−s.e.m; * p<0.05;  P<0.01; * P<0.005; MPP+vs control; one way Anova followed by Dunnett's test).

B. Effect of Kinetin Pre-Incubated During 6 Days on Dopaminergic Neurons after a MPP+ injury FIG. 2 depicts the effect of Kinetin pre-incubated during 6 days on survival of mouse primary dopaminergic neuron culture injured by $MPP^+$ (4 µM) expressed in percentage of control (mean±s.e.m; * $p<0.05$;  $P<0.01$; * $P<0.005$; MPP+vs control; one way Anova followed by Dunnett's test). $MPP^+$ applied at 4 µM for 48 h induced a large and significant decrease of TH positive neurons (FIG. 1) ~54%. Application of BDNF (10 ng/mL) displays a strong protective effect against $MPP^+$ injury (84%, **, $p<0.01$).

Pre-incubation of Kinetin 6 days before the injury shows a protective effect on TH neuron survival against MPP in a dose-dependent manner. Only the strongest concentration of Kinetin (100 µM) induces a statistically significant rescue of dopaminergic neuron survival (72%, *, $p<0.05$). In conclusion, Kinetin at 100 µM (pre-incubated 6 days before intoxication) is able to protect TH positive neurons form $MPP^+$ injury.

Figure 3:
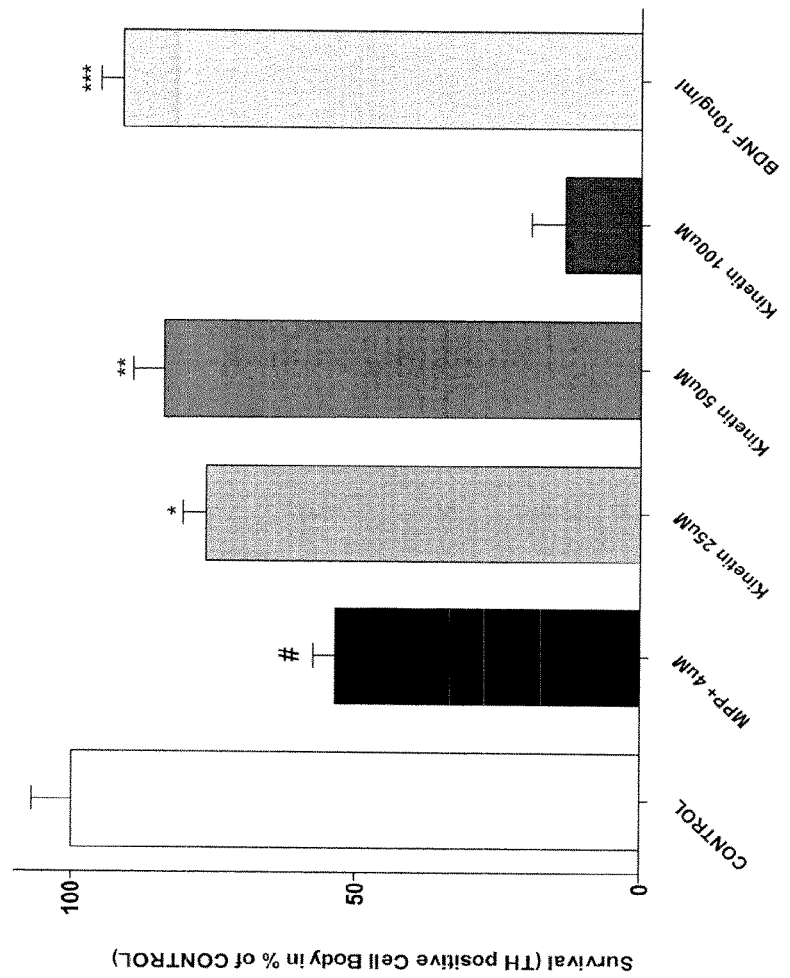
FIG. 3 depicts the effect of Kinetin pre-incubated during 10 days on survival of mouse primary dopaminergic neuron culture injured by MPP+ (4 µM) expressed in percentage of control. (mean+/−s.e.m; * p<0.05;  P<0.01; * P<0.005; MPP+vs control; one way Anova followed by Dunnett's test).

C. Effect of Kinetin Pre-Incubated During 10 Days on Dopaminergic Neurons after a MPP+ Injury FIG. 3 depicts the effect of Kinetin pre-incubated during 10 days on survival of mouse primary dopaminergic neuron culture injured by $MPP^+$ (4 µM) expressed in percentage of control (mean±s.e.m; * $p<0.05$;  $P<0.01$; * $P<0.005$; $MPP^+$ vs control; one way Anova followed by Dunnett's test). $MPP^+$ applied at 4 µM for 48 h induced a large and significant decrease of TH positive neurons (FIG. 1) ~47%. Application of BDNF (10 ng/mL) displays a strong protective effect against MPP injury (91%, ***, $p<0.001$).

Pre-incubation of Kinetin at 25 µM and 5004, 10 days before the injury shows a statistically significant protective effect on TH neuron survival against $MPP^+$ (respectively 76% of cell survival, *, $p<0.05$ and 84% of cell survival, **, $p<0.01$). In contrast, the strongest concentration of Kinetin (100 µM) appears to be toxic when incubated during a long time on dopaminergic neurons.

Kinetin shows a significant protective effect on dopaminergic neurons against $MPP^+$ injury. This effect is function of time of Kinetin pre-incubation and concentration. Indeed, a longer time of Kinetin pre-incubation before MPP+ intoxication (10 days) has revealed a significant protective of this compound at the two lowest concentrations tested 25 µM and 50 µM without any toxic effect.

Example 4

In Vivo Experimentation

The objective of this study will be to investigate whether the investigational compounds provide dopaminergic system protection in a mouse model of Parkinson's disease. 1-methyl-4-phenyl-1, 2, 3, 6-tetrahydropyridine (MPTP) is a neurotoxin precursor to MPP+, which causes permanent symptoms of Parkinson's disease by destroying dopaminergic neurons in the substantia nigra of the brain. In a MPTP model, the bilateral dopaminergic neuronal death of the substantia nigra and dopamine depletion of the striatum is created by repeated i.p. injection of MPTP. The compounds will be administered for 10 days prior to exposure to the neurotoxin MPTP, and will continue to be administered thereafter until the animals are sacrificed (see details below). Striatal levels of dopamine (DA), 3, 2-dihydroxyphenylacetic acid (DOPAC) and homovanillic acid (HVA) will be evaluated 7 days after the injection of MPTP with HPLC. In addition, the selective damage to dopaminergic neurons in the SNc will be evaluated with tyrosine hydroxylase (TH) immunorcactivity.

All animal experiments will be carried out according to the National Institute of Health (NIH) guidelines for the care and use of laboratory animals. Altogether 45 male, eight to twelve-week-old, C57Bl/6J mice, will be purchased from CRL Germany, are used for the experiment. Animals are housed at a standard temperature (22±1° C.) and in a light-controlled environment (lights on from 7 am to 9 pm) with ad libitum access to food and water. MPTP (Toronto Research Chemicals) is given twice a day at the dose of 15 mg/kg in saline i.p. at 3-h intervals on two consecutive days (Days 0 and 1), the total amount being then 60 mg/kg. The number of mice per MPTP treated group is 8 (n=8). Each compound will be prepared by dissolving in DMSO to create a 50 mM stock. 4 ul of this stock will be combined with 76 ul of water or saline to prepare for each i.p. injection.

Experiment Groups:
  Group 1: 8 mice treated with i.p. injections of MTK-0043 beginning 10 days before the onset of MPTP treatment and continuing until day 17 (sacrifice)
  Group 2: 8 mice treated with i.p. injections of MTK-0030 beginning 10 days before the onset of MPTP treatment and continuing until day 17 (sacrifice)
  Group 3: 8 mice treated with i.p. injections of MTK-0034 beginning 10 days before the onset of MPTP treatment and continuing until day 17 (sacrifice)
  Group 4: 8 mice treated with i.p. injections of MTK-0001 beginning 10 days before the onset of MPTP treatment and continuing until day 17 (sacrifice)
  Group 5: 8 mice without compound injections before the onset of MPTP treatment
  Group 6: 5 naive mice without MPTP or vehicle injections are used as controls for HPLC measurements (normal dopamine levels)

On day 17, the animals will be terminally anesthetized by pentobarbital (Mebunat, Orion Pharma) and subjected to cardiac puncture to collect blood samples into pre-cooled (ice bath) EDTA tubes. The tubes will be kept on ice and plasma is separated by centrifugation at 2000 g (+4° C.) immediately. 150-200 µl of plasma from each mouse is transferred into pre-cooled polypropylene tubes and kept frozen at −80° C. until sent to the Sponsor. Thereafter the mice will be transcardially perfused with heparinized (2.5 IU/ml) saline in order to remove blood from the brains. The brains will be removed, and striata will be dissected in toto, pooled, weighted, and snap-frozen in liquid nitrogen, and stored in −80° C.

The posterior brain block containing the SN is fixed by immersion in 4% paraformaldehyde in 0.1 M phosphate buffer (PB) for 24 hours. Following cryoprotection in 30% sucrose in 0.1M PB for 2-3 days, the blocks are frozen in liquid nitrogen and stored at −80° C. for TH THC. Remaining brain tissue (rest fraction) will be dissected, weighted and snap-frozen in liquid nitrogen, and stored in −80° C. until shipment to sponsor.

Tyrosine Hydroxylase Immunohistochemistry 20-µm-thick coronal cryosections are prepared with a cryostat (between AP −2.7 to 3.0 from bregma at 100-µm intervals). Additional sections from each mouse (2 slide sets) will be stored frozen for potential increased counting. For TH immunohistochemistry, the sections will be reacted with anti-TH-antibody (1:1000; Chemicon) for 1 day at +4° C. Thereafter the sections will be incubated with Alexa fluor secondary antibody (1:200; Molecular Probes). Finally, the sections will be rinsed, dehydrated, cover slipped and examined with Olympus AX-70 microscope. The number of TH-immunofluorescent neurons will be determined bilaterally by counting immunopositive cells through the SN pars compacta (4 sections per animal).

Dopamine (DA), 3, 4-dihydroxyphenylacetic acid (DOPAC) and homovanillic acid (HVA) concentrations in mouse striatal tissue samples will be determined by high performance liquid chromatography (HPLC) method with electrochemical detection. After thawing on ice, tissue samples are homogenized (1:10, w/v) in 0.1 M perchloric acid with MSE Soniprep 150 ultrasonic disintegrator (MSE Scientific Instruments, Crawley, UK). Tissue homogenates will be centrifuged for 15 min at 15000 g at 4° C. Supernatants will be filtered through polypropylene membrane (GHP Acrodisc Pall Corporation, Ann Arbor, Mich., USA) and diluted (1:1) with 0.1 M perchloric acid. The samples will be transferred into plastic vials and analyzed immediately.

The ESA HPLC system (ESA Inc., Chelmsford, Mass., USA) consist of a 582 solvent delivery system, a DG-1210 vacuum degasser, an 542 autosampler, a 880 thermostatted chamber, an eight-channel CoulArray® 5600 electrochemical array detector equipped with a two-channel 5014B microdialysis cell and a CoulArray® for Windows data acquisition module (version 1.00). The applied potentials are −175 mV (channel 1), +225 mV (channel 2), +350 mV (channel 3) and +450 mV (channel 4). DA and DOPAC are detected on channel 2 and HVA on channel 3. Injection volume is 10 µl.

The analytes are separated on a Zorbax SB-Aq reversed-phase column (2.1 100 mm, 3.5 pm, Agilent Technologies Inc., Little Falls, Wilmington, Del., USA) with a Zorbax SB-Aq precolumn (2.1, 12.5 mm, 5 µm) in an isocratic run. The column will be maintained at 35° C. The mobile phase is 100 µM monobasic sodium phosphate containing 4.75 µM citric acid monohydrate, 7 µM 1-octanesulfonic acid and 50 µM disodium EDT—md acetonitrile mixture (98:2, v/v). The pH of the mobile phase will be adjusted to 2.2 with o-phosphoric acid. The flow rate is 0.3 ml/min. The levels of DA, DOPAC and HVA will be expressed as nmol/g wet tissue.

The mice will be weighed on days 0, 10 and 17.

Animals are monitored daily by laboratory personnel. In the case that the general health status of an animal has significantly worsened, the mouse is terminated by an overdose of CO2, and decapitated. Definitions of acceptable endpoints include: no spontaneous movements and inability to drink or eat in 24-11 observation period, massive bleeding, spontaneous inflammation, missing anatomy, swelling or tumors larger than 20 mm, and inability to right itself in 30 sec period.

All values will be presented as mean±standard deviation (SD) or Standard Error of Mean (SEM), and differences are considered to be statistically significant at the $P<0.05$ level. Statistical analysis will be performed using StatsDirect statistical software. Differences between group means are analyzed by using unpaired t-test or 1-way-ANOVA followed by Dunnet's test (comparison to the control (=vehicle) group).

Documentation will delineate: body weight, Mean number of viable TH-positive neurons in SNc, Mean levels of DA, DOPAC, and HVA in striatum.

Example 5

The substantially same experiment will be performed above except that dosing will occur less than 10 days before the onset of MPTP treatment for each experimental group.

Example 6

The substantially same experiment will be performed above except that dosing will occur less than 10 days before the onset of MPTP treatment for each experimental group and dosing will also be tested at similar concnetrations but fed orally through water supply before the onset of MPTP treatment.

Example 7

The following experiment will be performed to determine if the compounds reduce symptoms of LD in a mouse model of the disease. Briefly, Ndufs4-null mice (KO) will be bred generated as described. The NesKO mice will be made by crossing the conditional Ndufs4 mice with Nestin-Cre mice. Pcp2-Cre mice and Ubc-CreERt2 mice will be used to inactivate Ndufs4 in Purkinje cells or in the adult by administration of tamoxifen, respectively. Mice will be maintained with rodent diet (5053; Picolab) and water available ad libitum with 12-h light-dark cycle at 22° C.

Details of visual placement/touch response, light/dark exploration, and rotarod tests can be found below. Briefly, Visual Placement/Touch Response. To test the vision of NesKO mice, the forepaw reaching reflex will be analyzed. When NesKO mice showed trunk curl or hind limb clasping the touch response was substituted. Mice will be lifted by the tail and moved toward the counter edge at a steady speed, slowing as the mouse approached the counter edge. The reaching reflex will be scored three times with 30 s in between each trial, before the mouse's whiskers touched the counter surface. Data were quantified as the percentage of forepaw-reaching events.

Light/Dark Exploration. To determine whether KO mice could differentiate between light and dark, mice will be acclimated to a 20×31-cm clean cage with fresh bedding for 1 h. One-third of the cage was covered and dark, the other two-thirds had bright lighting. A single test subject will be then transferred to a similar cage and exploratory movement was video taped. KO mice spent time equivalent to controls exploring the light side of cage.

Rotarod. Mice will be placed on a rotating drum (Rotarod; San Diego Instruments) that gradually accelerated from 4 rpm to 50 rpm during a 3-min test. The results of three to five replicates of each tested were averaged. For the UbCre-ERt tamoxifen-treated mice the first six sessions took place following the last day of tamoxifen treatment every 3-5 d for 1 mo. The last three sessions occurred during the 3 d before the mice will be sacrificed at −7, 6, 5, 4, 3, 2, and/or 1 mo after treatment.

Mitochondrial activity assays will be performed as described in Kruse. Briefly, mitochondria-enriched extracts will be prepared using Dounce homogenization and differential centrifugation to separate mitochondria from other cell membranes and cytosol. Submitochondrial particles will be produced by sonication for 10 s on ice using a Branson Sonifier 250 at 50% pulse and 30% output. Respiratory complex activity will be determined by recording the change in absorbance of decylubiquinone, NADH in the presence of specific substrates; inhibitors of specific complexes will be added to isolate the contribution of specific complexes. Polarography will be performed using homogenized brain tissue. Complex activities will be measured by monitoring the rate of oxygen consumption with an oxygen electrode. Complex-specific substrates and inhibitors were used to determine the oxygen consumption of complexes I, II, or IV.

Mice at different stages of disease will be anesthesized with an overdose of pentobarbital, perfused with PBS, followed by 4% paraformaldehyde (PFA). Tissue sections were cut and subjected to H&E, Luxol Fast Blue, Gallyas silver, Golgi, X-Gal, or FluoroJade C staining by standard methods. Either 8-μm paraffin sections or 30-μm free-floating sections were used for immunofluorescence with primary antibodies to the following: GFAP, laminin, CNPase, or caspase 3 or 8, phosphorylated AMPK or acetyl-CoA carboxylase, Iba-l-cfos, peripherin, myelin basic protein, calbindin; CD11b or NeuN. Sources of antibodies, dilutions, and visualization details can be found in SI Methods. EM was performed by standard techniques (SI Methods).

Western blots for Ndufs4, cleaved caspase-9, cleaved caspase-8, and GFAP will be performed as described elsewhere (33) and in SI Methods. Protein oxidation was assessed using an Oxyblot detection kit. For Southern blot analysis of the Ndufs4 gene, DNA from cerebellum, brainstem, or fore/hindbrain was digested with BspHI, electropohoresed on 1.0% agarose gels, transferred to nylon membrane, and hybridized with a unique probe that would distinguish Ndufs4+, Ndufs4lox, and NdufsΔ alleles.

Example 8

Drosophila Model of Mitochondrial Disease Treated with Kinetin

Mutations affecting mitochondrial complex I, a multisubunit assembly that couples electron transfer to proton pumping, are the most frequent cause of heritable mitochondrial diseases. Here, a Drosophila model of complex I deficiency caused by a homoplasmic mutation in the mitochondrial-encoded NADH dehydrogenase subunit 2 (ND2) gene is used. ND2 mutants exhibit phenotypes that resemble symptoms of mitochondrial disease, including shortened lifespan, progressive neurodegeneration, diminished neural mitochondrial membrane potential, and lower levels of neural ATP. This ND2 mutant model was used in "bang sensitivity" behavioral analysis to show the effects of kinetin treatment.

Methods

Drosophila Strains and Maintenance

All Drosophila strains were maintained on standard cornmeal/molasses medium at 25° C. with a 12-hour lightdark cycle. The ND2del1 and ND2ins1 stock was obtained from the laboratory of Dr. Patrick O'Farrell (University of California, San Francisco) (Xu et al., 2008). The isogenic w1118 stock was obtained from the Bloomington Drosophila Stock Center at Indiana University. To control for differences in nuclear genetic background, we outcrossed ND2 mutants to the w1118 strain. F1 offspring derived from crossing ND2 mutant females to w1118 males were used as the experimental group, given that they inherit mtDNA from the ND2 mutant strain; F1 offspring derived from crossing ND2 mutant males to w1118 females were used as the control group, given that they inherit mtDNA from the w1118 strain. The homoplasmic status of the ND2de11 mutation from the outcrossed ND2 mutant strain was reconfirmed by PCR and restriction digest analysis.

Mechanical Stress-Induced Paralysis

*Drosophila* strains with mutations affecting mitochondrial function often show an analogous seizure-like paralytic phenotype caused by mechanical-stress, termed "bang sensitivity" (Celotto et al., 2011; Fergestad et al., 2006; Ganetzky and Wu, 1982). Flies were assayed for bang sensitivity using a modification of a previously published protocol (Ganetzky and Wu, 1982). Briefly, flies were vortexed for 10 seconds in inverted glass vials containing cotton stoppers, and the time required for each individual animal to right itself was recorded.

MPP+ Exposure and Drug Treatment

Briefly, ND2 mutant flies were treated with Kinetin throughout their life. After aging 15 days, they were tested for bang sensitive paralysis. The following conditions were set: Control (no DMSO, n=48), DMSO (n=66), Adenine (n=76), and Kinetin (n=68). All conditions were treated with 10 μM of drug with the same volume of DMSO.

Statistics

Unless otherwise stated statistical significance tests were calculated using an unpaired two-tailed Student's t-test.

Results

Figure 4:
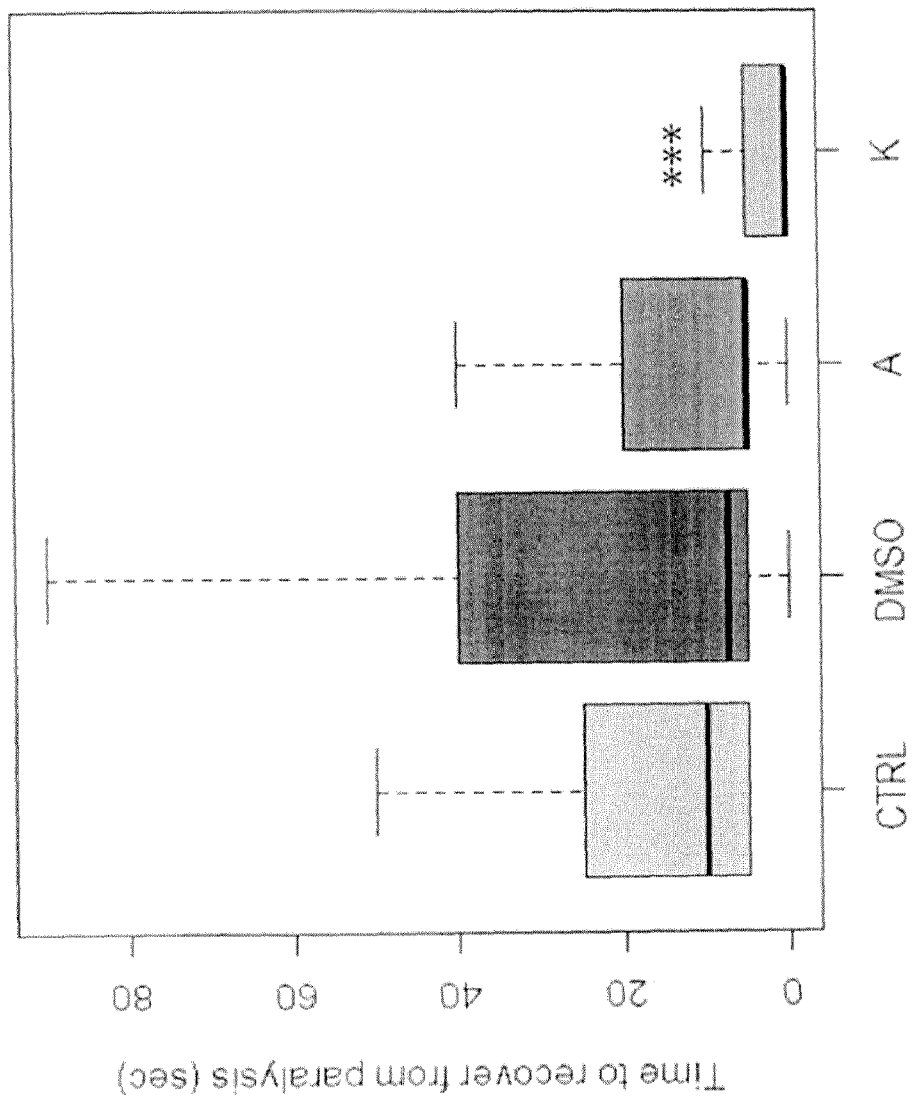
FIG. 4 depicts the effect of kinetin in a bang paralysis test administered to *Drosophila* flies.

FIG. 4 depicts a significant decrease in the time necessary for recovery of kinetin treated flies compared to other conditions. Control mean=approximately 17 seconds. dimethyl sulfoxide (DMSO) mean=approximately 14 seconds. Adenine mean (A)=approximately 9 seconds. Kinetin mean (K)=0.5 seconds.

Example 9

TABLE A

| COMPOUNDS | |
|---|---|
| (5-(2-(6-Methyl-1,2,5,7-tetraza-1H-inden-4-yl)ethyl)-2-furyl)methanol | 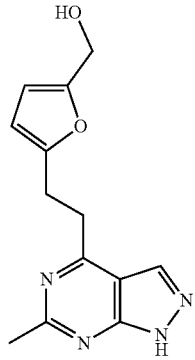 [SMILES: Cc1nc(CCc2ccc(CO)o2)c2cn[nH]c2n1] |
| 5-((6-Methyl-1,2,5,7-tetraza-1H-inden-4-ylamino)methyl)-2-furonitrile | 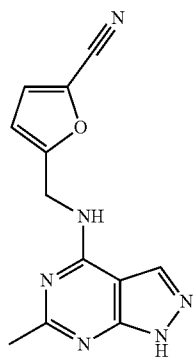 [SMILES: Cc1nc(NCc2ccc(C#N)o2)c2cn[nH]c2n1] |

TABLE A-continued

| COMPOUNDS | |
|---|---|
| 5-(2-(6-Methyl-1,2,5,7-tetraza-1H-inden-4-yl)ethyl)-2-furonitrile | 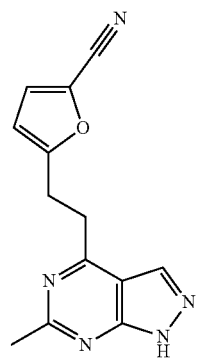 [SMILES: Cc1nc(CCc2ccc(C#N)o2)c2cn[nH]c2n1] |
| ((5-Methyl-2-furyl)methyl)(6-methyl-1,2,5,7-tetraza-1H-inden-4-yl)amine | 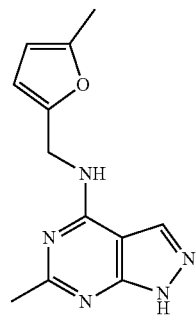 [SMILES: Cc1nc(NCc2ccc(C)o2)c2cn[nH]c2n1] |
| 6-Methyl-4-(2-(5-methyl-2-furyl)ethyl)-1,2,5,7-tetraza-1H-indene | 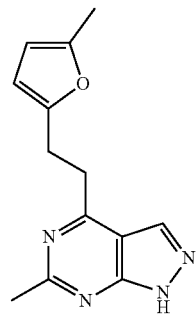 [SMILES: Cc1nc(CCc2ccc(C)o2)c2cn[nH]c2n1] |
| ((2-Pyrazinyl)methyl)(6-methyl-1,2,5,7-tetraza-1H-inden-4-yl)amine | 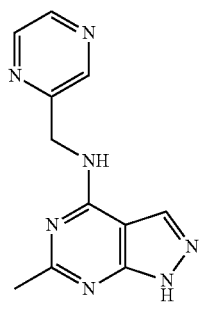 [SMILES: Cc1nc(NCc2cnccn2)c2cn[nH]c2n1] |

TABLE A-continued

| COMPOUNDS | | COMPOUNDS | |
|---|---|---|---|
| 6-Methyl-4-(2-(2-pyrazinyl)ethyl)-1,2,5,7-tetraza-1H-indene | | ((6-Methyl-2-pyrazinyl)methyl)(3-methyl-2.4.8.9-tetrazabicyclo[4.3.0]nona-1,3,5,7-tetraen-5-yl)amine | |
| 3-Methyl-5-(2-(6-methyl-2-pyrazinyl)ethyl)-2.4.8.9-tetrazabicyclo[4.3.0]nona-1,3,5,7-tetraene | | (6-((3-Methyl-2.4.8.9-tetrazabicyclo[4.3.0]nona-1,3,5,7-tetraen-5-ylamino)methyl)-2-pyrazinyl)methanol | |
| (9a-Adenineyl)(6-methyl-2-pyrazinyl)methane | | (6-((2-Methyl-9a-adenineyl)methyl)-2-pyrazinyl)methanol | |
| ((6-Methyl-2-pyrazinyl)methyl)-2.4.8.9-tetrazabicyclo[4.3.0]nona-1,3,5,7-tetraen-5-ylamine | | (6-((9a-Adenineyl)methyl)-2-pyrazinyl)methanol | |
| 2-Methyl-9a-((6-methyl-2-pyrazinyl)methyl)adenine | | (6-((2,4,8,9-Tetrazabicyclo[4.3.0]nona-1,3,5,7-tetraen-5-ylamino)methyl)-2-pyrazinyl)methanol | |

TABLE A-continued

| COMPOUNDS | |
|---|---|
| (6-(2-(3-Methyl-2,4,8,9-tetrazabicyclo[4.3.0]nona-1,3,5,7-tetraen-5-yl)ethyl)-2-pyrazinyl)methanol | |
| 3-Methyl-5-(2-(5-methyl-2-pyrazinyl)ethyl)-2,4,8,9-tetrazabicyclo[4.3.0]nona-1,3,5,7-tetraene | |
| ((5-Methyl-2-pyrazinyl)methyl)(3-methyl-2,4,8,9-tetrazabicyclo[4.3.0]nona-1,3,5,7-tetraen-5-yl)amine | |
| ((5-Methyl-2-pyrazinyl)methyl)-2,4,8,9-tetrazabicyclo[4.3.0]nona-1,3,5,7-tetraen-5-ylamine | |
| (9a-Adenineyl)(5-methyl-2-pyrazinyl)methane | |
| 2-Methyl-9a-((5-methyl-2-pyrazinyl)methyl)adenine | |
| (5-((3-Methyl-2,4,8,9-tetrazabicyclo[4.3.0]nona-1,3,5,7-tetraen-5-ylamino)methyl)-2-pyrazinyl)methanol | |
| (5-((2,4,8,9-tetrazabicyclo[4.3.0]nona-1,3,5,7-tetraen-5-ylamino)methyl)-2-pyrazinyl)methanol | |

TABLE A-continued

| COMPOUNDS | |
|---|---|
| (5-((2-Methyl-9a-adenineyl)methyl)-2-pyrazinyl)methanol | |
| (5-((9a-Adenineyl)methyl)-2-pyrazinyl)methanol | |
| (5-(2-(3-Methyl-2,4,8,9-tetrazbicyclo[4.3.0]nona-1,3,5,7-tetraen-5-yl)ethyl)-2-pyrazinyl)methanol | |
| 3-Methyl-5-(2-(3-methyl-2-pyrazinyl)ethyl)-2,4,8,9-tetrazabicyclo[4.3.0]nona-1,3,5,7-tetraene | |
| ((3-Methyl-2-pyrazinyl)methyl)(3-methyl-2,4,8,9-tetrazabicyclo[4.3.0]nona-1,3,5,7-tetraen-5-yl)amine | |
| 2-Methyl-9a-((3-methyl-2-pyrazinyl)methyl)adenine | |
| (9a-Adenineyl)(3-methyl-2-pyrazinyl)methane | |
| ((3-Methyl-2-pyrazinyl)methyl)-2,4,8,9-tetrazabicyclo[4.3.0]nona-1,3,5,7-tetraen-5-ylamine | |
| (3-(2-(3-Methyl-2,4,8,9-tetrazabicyclo[4.3.0]nona-1,3,5,7-tetraen-5-yl)ethyl)-2-pyrazinyl)methanol | |

TABLE A-continued

COMPOUNDS (3-((3-Methyl-2,4,8,9-tetrazabicyclo[4.3.0]nona-1,3,5,7-tetraen-5-ylamino)methyl)-2-pyrazinyl)methanol (3-((2-Methyl-9a-adenineyl)methyl)-2-pyrazinyl)methanol (3-((9a-Adenineyl)methyl)-2-pyrazinyl)methanol (3-(2-(3-Methyl-2,4,8,9-tetrazabicyclo[4.3.0]nona-1,3,5,7-tetraen-5-yl)ethyl)-2-pyrazinyl)methanol MTK-0048
(1,2a,5,6,8-Pentaza-4,5-dihydro-3H-acenaphthylen-3-yl)(2-furyl)methane MTK-0069
(Furfuryl)-1,7-diazabicyclo[4.3.0]nona-2,4,6,8-tetraen-2-ylamine

---

The invention claimed is:

1. A method of treating a neurodegenerative disease comprising administering to a subject in need thereof an effective amount of a compound having a structure represented by a formula:

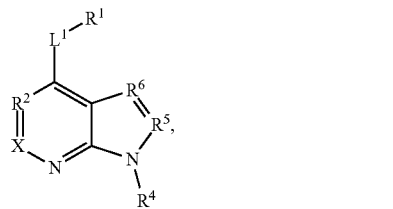

wherein X is selected from C—H, C—CH$_3$, C—CH$_2$CH$_3$, C—CH$_2$CH$_2$CH$_3$, and CR$^3$;

R$^3$ is selected from a substituted or unsubstituted cycloalkyl, a substituted or unsubstituted heterocycloalkyl, a substituted or unsubstituted aryl, and a substituted or unsubstituted heteroaryl;

L$^1$ is a bond, substituted or unsubstituted alkylene, or substituted or unsubstituted heteroalkylene;

R$^1$ is hydrogen, oxo, halogen, —CY$_3$, —CN, —SO$_2$Cl, —SO$_v$R$^{10}$, —SO$_v$NR$^7$R$^8$, —NHNH$_2$, —ONR$^7$R$^8$, NHC═(O)NHNH$_2$, —NHC═(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$R$^{10}$, —N(R$^7$)C═(O)R$^9$, —NR$^7$C(O)—OR$^9$, —NR$^7$OR$^9$, —OCY$_3$, —OCHY$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^2$ is N;

R$^4$ is hydrogen, substituted or unsubstituted cycloalkyl, substituted or unsubstituted heterocycloalkyl, substituted or unsubstituted aryl, or substituted or unsubstituted heteroaryl;

R$^5$ is CH, CCH$_3$, CCF$_3$, or CC$_6$H$_5$;

R$^6$ is N or CH;

R$^7$ and R$^8$ are independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ and R$^{10}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHC(O)—OH, —NHOH, —OCF$_3$, —OCHF$_2$, substituted or unsubstituted alkyl, substituted or unsubstituted heteroalkyl, substituted or unsubstittuted cycloalkyl, substituted or unsubstituted heterocycloalkyl, substituted or unsubstituted aryl, or substituted or unsubstituted heteroaryl;

m and v are independently 1 or 2; and n is independently an integer from 0 to 4, and Y is independently —Cl, —Br, —I, or —F, or a pharmaceutically acceptable salt thereof, provided the compound is not kinetin or cytokinin, and wherein the neurodegenerative disorder is selected from Parkinson's disease, Huntington's disease, amyotrophic lateral sclerosis, and Leigh syndrome.

2. A method of treating a neurodegenerative disease comprising administering to a subject in need thereof an effective amount of a compound having a structure represented by a formula:

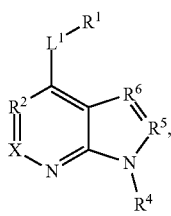

wherein X is selected from a C—H, C—CH₃, C—CH₂CH₃, C—CH₂CH₂CH₃, and CR³;

R³ is selected from a substituted or unsubstituted cycloalkyl, a substituted or unsubstituted heterocycloalkyl, a substituted or unsubstituted aryl, and a substituted or unsubstituted heteroaryl;

L¹ is a bond, substituted or unsubstituted alkylene, or substituted or unsubstituted heteroalkylene;

R¹ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is N;

R⁴ is hydrogen, substituted or unsubstituted cycloalkyl, substituted or unsubstituted heterocycloalkyl, substituted or unsubstituted aryl, or substituted or unsubstituted heteroaryl;

R⁵ is CCH₃, CCF₃, or CC₆H₅; and

R⁶ is N, or a pharmaceutically acceptable salt thereof, provided the compound is not kinetin or cytokinin, and wherein the neurodegenerative disorder is selected from Parkinson's disease, Huntington's disease, amyotrophic lateral sclerosis, and Leigh syndrome.

3. The method of claim 1, wherein the neurodegenerative disease is selected from the group consisting of Parkinson's disease, Huntington's disease, and amyotrophic lateral sclerosis.

4. The method of claim 1, wherein the neurodegenerative disease is Parkinson's disease.

5. The method of claim 3, wherein the neurodegenerative disease is Huntington's disease.

6. The method of claim 3, wherein the neurodegenerative disease is amyotrophic lateral sclerosis.

7. The method of claim 1, wherein the compound has a structure represented by a formula selected from:

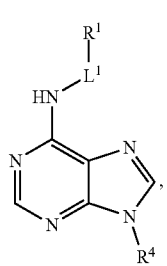

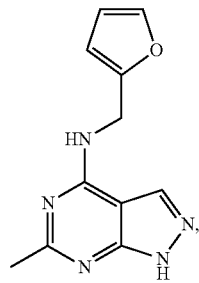

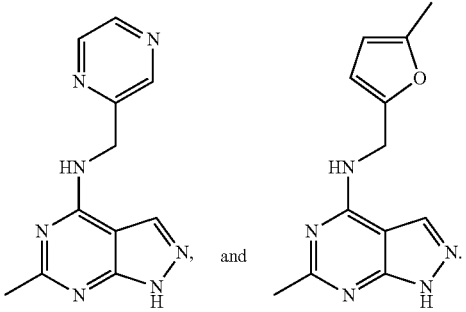

8. The method of claim 1, wherein X is C—H or C—CH₃.

9. The method of claim 1, wherein R² is N; X is C—H or C—CH₃; R⁴ is hydrogen, and wherein R⁶ is N.

10. The method of claim 1, wherein X is CR³, wherein R³ is selected from the group consisting of: H, CH₃, substituted or unsubstituted cycloalkyl, substituted or unsubstituted heterocycloalkyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl, substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, unsubstituted pyrrolidinyl, substituted or unsubstituted 2,5-dihydro-1H-pyrrolyl, substituted or unsubstituted cyclopentyl, substituted or unsubstituted cyclopentenyl, substituted or unsubstituted 1,3-oxathiolanyl, and wherein L¹ is a bond or an amine.

11. The method of claim 1, wherein L¹ is N—H.

12. The method of claim 1, wherein L¹ is N—H, wherein R² is N, wherein R⁴ is hydrogen, wherein R⁶ is N, and wherein R¹ is a substituted or unsubstituted alkyl group or heteroalkyl group.

13. The method of claim 1, wherein L¹ is N—H, wherein R² is N, wherein R⁴ is hydrogen, wherein R⁶ is N, and wherein R¹ is a substituted carbon, propyl, butyl, propylene, or butylene group.

14. The method of claim 1, wherein the compound is

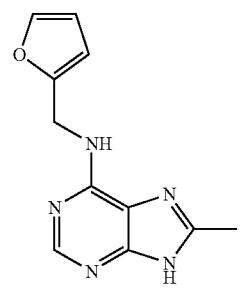

15. The method of claim 1, wherein administering the compound to the subject in need thereof comprises administering a pharmaceutical composition comprising: (i) a therapeutically effective amount of the compound or a pharmaceutically acceptable salt thereof; and (ii) a pharmaceutically acceptable carrier.

16. The method of claim 15, wherein $R^1$ is the substituted or unsubstituted heteroaryl.

17. The method of claim 15, wherein $R^1$ is the substituted or unsubstituted alkyl, and wherein the substituted or unsubstituted alkyl is a substituted or unsubstituted alkenyl.

18. The method of claim 15, wherein the compound is selected from:

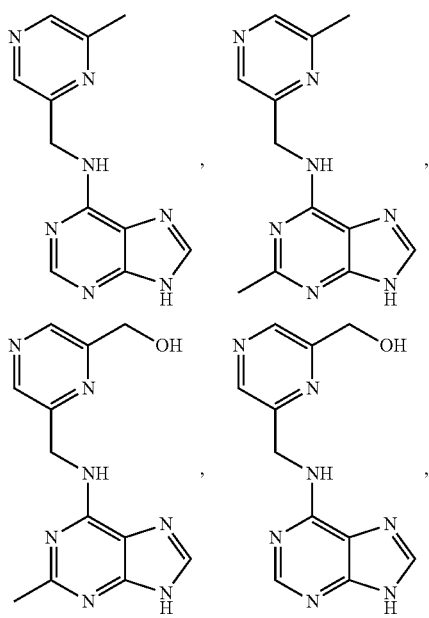

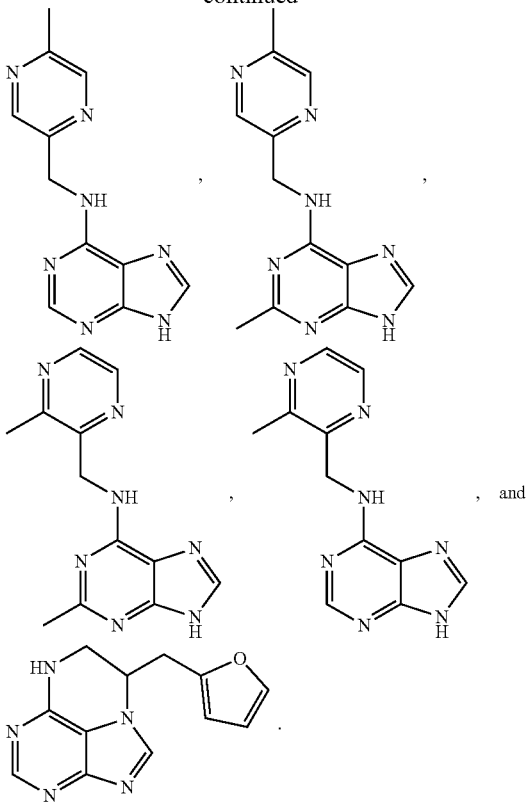

19. The method of claim 1, wherein $R^5$ is $CCF_3$.

20. The method of claim 2, wherein $R^5$ is $CCF_3$.

* * * * *